US010278373B2

(12) United States Patent
Harada et al.

(10) Patent No.: US 10,278,373 B2
(45) Date of Patent: May 7, 2019

(54) HLA CLASS I-EXPRESSING NON-HUMAN ANIMAL

(71) Applicant: TAIHO PHARMACEUTICAL CO., LTD., Tokyo (JP)

(72) Inventors: Naomoto Harada, Ibaraki (JP); Satoshi Fukaya, Ibaraki (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/029,305

(22) PCT Filed: Oct. 17, 2014

(86) PCT No.: PCT/JP2014/077668
§ 371 (c)(1),
(2) Date: Apr. 14, 2016

(87) PCT Pub. No.: WO2015/056774
PCT Pub. Date: Apr. 23, 2015

(65) Prior Publication Data
US 2016/0227750 A1    Aug. 11, 2016

(30) Foreign Application Priority Data
Oct. 18, 2013    (JP) .................................. 2013-217684

(51) Int. Cl.
*A01K 67/027*    (2006.01)
*G01N 33/50*    (2006.01)
*C07K 14/74*    (2006.01)
*C12N 15/90*    (2006.01)

(52) U.S. Cl.
CPC .... *A01K 67/0278* (2013.01); *C07K 14/70539* (2013.01); *C12N 15/907* (2013.01); *G01N 33/505* (2013.01); *G01N 33/5008* (2013.01); *G01N 33/5014* (2013.01); *G01N 33/5023* (2013.01); *G01N 33/5088* (2013.01); *A01K 2207/15* (2013.01); *A01K 2217/072* (2013.01); *A01K 2227/105* (2013.01); *A01K 2267/0387* (2013.01); *C07K 2319/00* (2013.01); *G01N 2333/70539* (2013.01)

(58) Field of Classification Search
CPC .................................................. A01K 67/0278
See application file for complete search history.

(56) References Cited

U.S. PATENT DOCUMENTS

| 6,558,663 B1 * | 5/2003 | Seebach | A61K 39/001 424/93.2 |
| 9,657,311 B2 * | 5/2017 | Bauche | C12N 15/86 |
| 2005/0066375 A1 | 3/2005 | Thiam et al. | |

FOREIGN PATENT DOCUMENTS

WO    WO 2013/063346 A1    5/2013

OTHER PUBLICATIONS

Keefer, PNAS 2015;112:8874-8.*
Polejaeva et al, Nature 2000;407:86-90.*
Wilmut, Cloning Stem Cell 2003;5:99-100.*
Yanagimachi, Mole Cell Endocrinol 2002;187:241-8.*
Mullins, J Clin Invest, 1996;97:1557-60.*
Moreadith et al., J. Mol. Med. 1997;75:208-16.*
Supplementary European Search Report dated Apr. 18, 2017, in EP 14853234.4.
Boucherma et al., "HLA-A*01:03, HLA-A*24:02, HLA-B*08:01, HLA-B*27:05, HLA-B*35:01, HLA-B*44:02, and HLA-C*07:01 Monochain Transgenic/H-2 Class I Null Mice: Novel Versatile Preclinical Models of Human T Cell Responses," The Journal of Immunology, 2013, 191:583-293.
Cheuk et al., "Human MHC Class I Transgenic Mice Deficient for H2 Class I Expression Facilitate Identification and Characterization of New HLA Class I-Restricted Viral T Cell Epitopes," The Journal of Immunology, 2002, 169:5571-5580.
Harada et al., "Generation of a Novel HLA Class I Transgenic Mouse Model Carrying a Knock-in Mutation at the $\beta_2$-Microglobulin Locus," The Journal of Immunology, 2017 (online Nov. 23, 2016), 198:516-527.
International Search Report in PCT/JP2014/077668 dated Jan. 20, 2015.
Apostolopoulos et al., "MHC and MHC-like molecules," Human Vaccines, Nov./Dec. 2008, 4(6):400-409.
Epstein et al., "Expression and function of HLA-A2.1 in transgenic mice," Eur. J. Immunol., Sep. 1989, 19(9):1575-1583.
Koller et al., "Normal Development of Mice Deficient in $\beta_2$M, MHC Class I Proteins, and CD8+ T Cells," Science, Jun. 8, 1990, 248:1227-1230.
Le et al, "Cytotoxic T Cell Responses in HLA-A2.1 Transgenic Mice: Recognition of HLA Alloantigens and Utilization of HLA-A2.1 as a Restriction Element," J. Immunol., Feb. 15, 1989, 142(4):1366-1371.
Mage et al., "A recombinant, soluble, single-chain class I major histocompatibility complex molecule with biological activity," Proc. Natl. Acad. Sci. USA, Nov. 15, 1992, 89(22):10658-10662.
Pascolo et al., "HLA-A2.1-restricted Education and Cytolytic Activity of CD8+ T Lymphocytes from $\beta 2$ Microglobulin ($\beta 2m$) HLA-A2.1 Monochain Transgenic H-2D$^b$ $\beta 2m$ Double Knockout Mice," J. Exp. Med., Jun. 16, 1997, 185(12):2043-2051.

(Continued)

*Primary Examiner* — Scott Long
(74) *Attorney, Agent, or Firm* — Foley & Lardner LLP

(57) ABSTRACT

This invention provides an HLA class I-expressing non-human animal that can be prepared efficiently in a simple manner within a short period of time, in which the transgene copy number to be introduced thereinto and the integration site of transgene are regulated, and in which the expression level of the transgene and the site of expression thereof are regulated. The invention also provides a method for preparing such non-human animal. In such HLA class I gene knock-in non-human animal, an artificial chimeric gene encoding an artificial chimeric protein comprising a protein composed of $\beta 2$ microglobulin, HLA class I $\alpha 1$ and $\alpha 2$ regions, and an MHC class I $\alpha 3$ region of a non-human animal ligated in such order from the N terminus is expressed under the control of a transcription regulatory region of $\beta 2$ microglobulin gene of the non-human animal.

33 Claims, 21 Drawing Sheets

Specification includes a Sequence Listing.

(56) References Cited

OTHER PUBLICATIONS

Shultz et al., "Generation of functional human T-cell subsets with HLA-restricted immune responses in HLA class I expressing NOD/SCID/IL2r$\gamma^{null}$ humanized mice," Proc. Natl. Acad. Sci. USA, Jul. 20, 2010, 107(29):13022-13027.

Ureta-Vidal et al., "Phenotypical and Functional Characterization of the CD8$^+$ T Cell Repertoire of HLA-A2.1 Transgenic, H-2K$^{bo}$D$^{bo}$ Double Knockout Mice," J. Immunol., 1999, 163:2555-2560.

Vitiello et al., "Analysis of the HLA-restricted Influenza-specific Cytotoxic T Lymphocyte Response in Transgenic Mice Carrying a Chimeric Human-Mouse Class I Major Histocompatibility Complex," J. Exp. Med., Apr. 1, 1991, 173(4):1007-1015.

Zijlstra et al., "β2-Microglobulin deficient mice lack CD4$^-$8$^+$ cytolytic T cells," Nature, Apr. 19, 1990, 344(6268):742-746.

Boucherma et al., "HLA-A*01:03, HLA-A*24:02, HLA-B*08:01, HLA-B*27:05, HLA-B*35:01, HLA-B*44:02, and HLA-C*07:01 Monochain Transgenic/H-2 Class I Null Mice: Novel Versatile Preclinical Models of Human T Cell Responses," The Journal of Immunology, 2013, 191:583-593.

\* cited by examiner

SEQUENCE LISTING

```
<160> NUMBER OF SEQ ID NOS: 57

<210> SEQ ID NO 1
<211> LENGTH: 119
<212> TYPE: PRT
<213> ORGANISM: Homo sapiens

<400> SEQUENCE: 1

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 2
<211> LENGTH: 365
<212> TYPE: PRT
<213> ORGANISM: Homo sapiens

<400> SEQUENCE: 2
```

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Ser Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65              70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
        115                 120                 125

Ser Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
            165                 170                 175

Ala Glu Gln Gln Arg Ala Tyr Leu Glu Gly Thr Cys Val Asp Gly Leu
        180                 185                 190

Arg Arg Tyr Leu Glu Asn Gly Lys Glu Thr Leu Gln Arg Thr Asp Pro
    195                 200                 205

Pro Lys Thr His Met Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
        260                 265                 270

Val Pro Ser Gly Glu Glu Gln Arg Tyr Thr Cys His Val Gln His Glu
    275                 280                 285

Gly Leu Pro Lys Pro Leu Thr Leu Arg Trp Glu Pro Ser Ser Gln Pro
290                 295                 300

Thr Val Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Asn Ser
            325                 330                 335

Ser Asp Arg Lys Gly Gly Ser Tyr Ser Gln Ala Ala Ser Ser Asp Ser
        340                 345                 350

Ala Gln Gly Ser Asp Val Ser Leu Thr Ala Cys Lys Val
    355                 360                 365

<210> SEQ ID NO 3
<211> LENGTH: 365
<212> TYPE: PRT
<213> ORGANISM: Homo sapiens

<400> SEQUENCE: 3

Met Ala Val Met Ala Pro Arg Thr Leu Val Leu Leu Leu Ser Gly Ala

Leu Ala Leu Thr Gln Thr Trp Ala Gly Ser His Ser Met Arg Tyr Phe
                20                  25                  30

Ser Thr Ser Val Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala
            50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
                115                 120                 125

Ser Asp Gly Arg Phe Leu Arg Gly Tyr His Gln Tyr Ala Tyr Asp Gly
130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Val Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Asn Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
                355                 360                 365

<210> SEQ ID NO 4
<211> LENGTH: 363
<212> TYPE: PRT
<213> ORGANISM: Homo sapiens

<400> SEQUENCE: 4

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gln Glu Thr Arg Asn Val Lys Ala Gln Ser Gln
                85                  90                  95

Thr Asp Arg Val Asp Leu Gly Thr Leu Arg Gly Tyr Tyr Asn Gln Ser
            100                 105                 110

Glu Ala Gly Ser His Thr Ile Gln Ile Met Tyr Gly Val Gly Ser Asp
        115                 120                 125

Gly Arg Phe Leu Arg Gly Tyr Arg Gln Asp Ala Tyr Asp Gly Lys Asp
    130                 135                 140

Tyr Ile Ala Leu Asn Glu Asp Leu Arg Ser Trp Thr Ala Ala Asp Met
145                 150                 155                 160

Ala Ala Gln Ile Thr Lys Arg Lys Trp Glu Ala Ala His Glu Ala Glu
                165                 170                 175

Gln Leu Arg Ala Tyr Leu Asp Gly Thr Cys Val Glu Trp Leu Arg Arg
            180                 185                 190

Tyr Leu Glu Asn Gly Lys Glu Thr Leu Gln Arg Thr Asp Pro Pro Lys
        195                 200                 205

Thr His Met Thr His His Pro Ile Ser Asp His Glu Ala Thr Leu Arg
    210                 215                 220

Cys Trp Ala Leu Gly Phe Tyr Pro Ala Glu Ile Thr Leu Thr Trp Gln
225                 230                 235                 240

Arg Asp Gly Glu Asp Gln Thr Gln Asp Thr Glu Leu Val Glu Thr Arg
                245                 250                 255

Pro Ala Gly Asp Gly Thr Phe Gln Lys Trp Ala Ala Val Val Val Pro
            260                 265                 270

Ser Gly Glu Glu Gln Arg Tyr Thr Cys His Val Gln His Glu Gly Leu
        275                 280                 285

Pro Lys Pro Leu Thr Leu Arg Trp Glu Leu Ser Ser Gln Pro Thr Ile
    290                 295                 300

Pro Ile Val Gly Ile Ile Ala Gly Leu Val Leu Leu Gly Ala Val Ile
305                 310                 315                 320

Thr Gly Ala Val Val Ala Ala Val Met Trp Arg Arg Lys Ser Ser Asp
                325                 330                 335

Arg Lys Gly Gly Ser Tyr Thr Gln Ala Ala Ser Ser Asp Ser Ala Gln
            340                 345                 350

Gly Ser Asp Val Ser Leu Thr Ala Cys Lys Val
        355                 360

<210> SEQ ID NO 5
<211> LENGTH: 365
<212> TYPE: PRT
<213> ORGANISM: Homo sapiens

<400> SEQUENCE: 5

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
 50                  55                  60

Ala Ser Gln Arg Met Glu Pro Arg Ala Pro Trp Ile Glu Gln Glu Gly
 65                  70                  75                  80

Pro Glu Tyr Trp Asp Gln Glu Thr Arg Asn Val Lys Ala Gln Ser Gln
                 85                  90                  95

Thr Asp Arg Val Asp Leu Gly Thr Leu Arg Gly Tyr Tyr Asn Gln Ser
            100                 105                 110

Glu Ala Gly Ser His Thr Ile Gln Ile Met Tyr Gly Cys Asp Val Gly
            115                 120                 125

Ser Asp Gly Arg Phe Leu Arg Gly Tyr Arg Gln Asp Ala Tyr Asp Gly
            130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Asp Gly Thr Cys Val Glu Trp Leu
            180                 185                 190

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Leu Ser Ser Gln Pro
290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 6
<211> LENGTH: 365
<212> TYPE: PRT
<213> ORGANISM: Homo sapiens

<400> SEQUENCE: 6

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala

```
            35                  40                  45
Val Gly Tyr Val Asp Asp Thr Gln Phe Val Arg Phe Asp Ser Asp Ala
 50                  55                  60

Ala Ser Gln Arg Met Glu Pro Arg Ala Pro Trp Ile Glu Gln Glu Gly
 65                  70                  75                  80

Pro Glu Tyr Trp Asp Gly Glu Thr Arg Lys Val Lys Ala His Ser Gln
                 85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 7
<211> LENGTH: 365
<212> TYPE: PRT
<213> ORGANISM: Homo sapiens

<400> SEQUENCE: 7

Met Ala Val Met Ala Pro Arg Thr Leu Val Leu Leu Leu Ser Gly Ala
 1                   5                  10                  15

Leu Ala Leu Thr Gln Thr Trp Ala Gly Ser His Ser Met Arg Tyr Phe
                 20                  25                  30

Phe Thr Ser Val Ser Arg Pro Gly Arg Gly Glu Pro Arg Phe Ile Ala
             35                  40                  45
```

```
Val Gly Tyr Val Asp Asp Thr Gln Phe Val Arg Phe Asp Ser Asp Ala
 50                  55                  60

Ala Ser Gln Arg Met Glu Pro Arg Ala Pro Trp Ile Glu Gln Glu Gly
 65                  70                  75                  80

Pro Glu Tyr Trp Asp Gly Glu Thr Arg Lys Val Lys Ala His Ser Gln
                 85                  90                  95

Thr His Arg Val Asp Leu Gly Thr Leu Arg Gly Tyr Tyr Asn Gln Ser
                100                 105                 110

Glu Ala Gly Ser His Thr Val Gln Arg Met Tyr Gly Cys Asp Val Gly
            115                 120                 125

Ser Asp Trp Arg Phe Leu Arg Gly Tyr His Gln Tyr Ala Tyr Asp Gly
130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Thr Ala His Glu
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
            210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
            290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 8
<211> LENGTH: 365
<212> TYPE: PRT
<213> ORGANISM: Homo sapiens

<400> SEQUENCE: 8

Met Ala Val Met Ala Pro Arg Thr Leu Leu Leu Leu Leu Leu Gly Ala
 1               5                  10                  15

Leu Ala Leu Thr Gln Thr Trp Ala Gly Ser His Ser Met Arg Tyr Phe
                 20                  25                  30

Thr Thr Ser Val Ser Arg Pro Gly Arg Gly Glu Pro Arg Phe Ile Ala
             35                  40                  45

Val Gly Tyr Val Asp Asp Thr Gln Phe Val Arg Phe Asp Ser Asp Ala
 50                  55                  60
```

```
Ala Ser Gln Arg Met Glu Pro Arg Ala Pro Trp Ile Glu Gln Glu Arg
 65                  70                  75                  80

Pro Glu Tyr Trp Asp Gln Glu Thr Arg Asn Val Lys Ala His Ser Gln
             85                  90                  95

Ile Asp Arg Val Asp Leu Gly Thr Leu Arg Gly Tyr Tyr Asn Gln Ser
            100                 105                 110

Glu Ala Gly Ser His Thr Ile Gln Met Met Tyr Gly Cys Asp Val Gly
        115                 120                 125

Ser Asp Gly Arg Phe Leu Arg Gly Tyr Gln Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Gln Arg Lys Trp Glu Ala Ala Arg Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ser Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Phe Ala Gly Ala Val Val Ala Val Arg Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Met Ser Leu Thr Ala Cys Lys Val
        355                 360                 365

<210> SEQ ID NO 9
<211> LENGTH: 365
<212> TYPE: PRT
<213> ORGANISM: Homo sapiens

<400> SEQUENCE: 9

Met Ala Val Met Ala Pro Arg Thr Leu Leu Leu Leu Leu Leu Gly Ala
  1               5                  10                  15

Leu Ala Leu Thr Gln Thr Trp Ala Gly Ser His Ser Met Arg Tyr Phe
             20                  25                  30

Thr Thr Ser Val Ser Arg Pro Gly Arg Gly Glu Pro Arg Phe Ile Ala
         35                  40                  45

Val Gly Tyr Val Asp Asp Thr Gln Phe Val Arg Phe Asp Ser Asp Ala
     50                  55                  60

Ala Ser Gln Arg Met Glu Pro Arg Ala Pro Trp Ile Glu Gln Glu Arg
```

```
            65                  70                  75                  80
        Pro Glu Tyr Trp Asp Gln Glu Thr Arg Asn Val Lys Ala His Ser Gln
                         85                  90                  95
        Ile Asp Arg Val Asp Leu Gly Thr Leu Arg Gly Tyr Tyr Asn Gln Ser
                        100                 105                 110
        Glu Ala Gly Ser His Thr Ile Gln Ile Met Tyr Gly Cys Asp Val Gly
                        115                 120                 125
        Ser Asp Gly Arg Phe Leu Arg Gly Tyr Arg Gln Asp Ala Tyr Asp Gly
                        130                 135                 140
        Lys Asp Tyr Ile Ala Leu Asn Glu Asp Leu Arg Ser Trp Thr Ala Ala
        145                 150                 155                 160
        Asp Met Ala Ala Gln Ile Thr Gln Arg Lys Trp Glu Ala Ala Arg Val
                        165                 170                 175
        Ala Glu Gln Leu Arg Ala Tyr Leu Glu Gly Thr Cys Val Glu Trp Leu
                        180                 185                 190
        Arg Arg Tyr Leu Glu Asn Gly Lys Glu Thr Leu Gln Arg Thr Asp Pro
                        195                 200                 205
        Pro Lys Thr His Met Thr His His Ala Val Ser Asp His Glu Ala Thr
                        210                 215                 220
        Leu Arg Cys Trp Ala Leu Ser Phe Tyr Pro Ala Glu Ile Thr Leu Thr
        225                 230                 235                 240
        Trp Gln Arg Asp Gly Glu Asp Gln Thr Gln Asp Thr Glu Leu Val Glu
                        245                 250                 255
        Thr Arg Pro Ala Gly Asp Gly Thr Phe Gln Lys Trp Ala Ser Val Val
                        260                 265                 270
        Val Pro Ser Gly Gln Glu Gln Arg Tyr Thr Cys His Val Gln His Glu
                        275                 280                 285
        Gly Leu Pro Lys Pro Leu Thr Leu Arg Trp Glu Pro Ser Ser Gln Pro
                        290                 295                 300
        Thr Ile Pro Ile Val Gly Ile Ile Ala Gly Leu Val Leu Phe Gly Ala
        305                 310                 315                 320
        Val Phe Ala Gly Ala Val Val Ala Ala Val Arg Trp Arg Arg Lys Ser
                        325                 330                 335
        Ser Asp Arg Lys Gly Gly Ser Tyr Ser Gln Ala Ala Ser Ser Asp Ser
                        340                 345                 350
        Ala Gln Gly Ser Asp Met Ser Leu Thr Ala Cys Lys Val
                        355                 360                 365

<210> SEQ ID NO 10
<211> LENGTH: 369
<212> TYPE: PRT
<213> ORGANISM: Mus musculus

<400> SEQUENCE: 10

Met Val Pro Cys Thr Leu Leu Leu Leu Ala Ala Leu Ala Pro
        1               5                   10                  15
        Thr Gln Thr Arg Ala Gly Pro His Ser Leu Arg Tyr Phe Val Thr Ala
                        20                  25                  30
        Val Ser Arg Pro Gly Leu Gly Glu Pro Arg Tyr Met Glu Val Gly Tyr
                        35                  40                  45
        Val Asp Asp Thr Glu Phe Val Arg Phe Asp Ser Asp Ala Glu Asn Pro
                        50                  55                  60
        Arg Tyr Glu Pro Arg Ala Arg Trp Met Glu Gln Glu Gly Pro Glu Tyr
        65                  70                  75                  80
```

```
Trp Glu Arg Glu Thr Gln Lys Ala Lys Gly Asn Glu Gln Ser Phe Arg
                85                  90                  95

Val Asp Leu Arg Thr Leu Leu Gly Tyr Tyr Asn Gln Ser Lys Gly Gly
            100                 105                 110

Ser His Thr Ile Gln Val Ile Ser Gly Cys Glu Val Gly Ser Asp Gly
        115                 120                 125

Arg Leu Leu Arg Gly Tyr Gln Gln Tyr Ala Tyr Asp Gly Cys Asp Tyr
    130                 135                 140

Ile Ala Leu Asn Glu Asp Leu Lys Thr Trp Thr Ala Ala Asp Met Ala
145                 150                 155                 160

Ala Leu Ile Thr Lys His Lys Trp Glu Gln Ala Gly Glu Ala Glu Arg
                165                 170                 175

Leu Arg Ala Tyr Leu Glu Gly Thr Cys Val Glu Trp Leu Arg Arg Tyr
            180                 185                 190

Leu Lys Asn Gly Asn Ala Thr Leu Leu Arg Thr Asp Ser Pro Lys Ala
        195                 200                 205

His Val Thr His His Ser Arg Pro Glu Asp Lys Val Thr Leu Arg Cys
    210                 215                 220

Trp Ala Leu Gly Phe Tyr Pro Ala Asp Ile Thr Leu Thr Trp Gln Leu
225                 230                 235                 240

Asn Gly Glu Glu Leu Ile Gln Asp Met Glu Leu Val Glu Thr Arg Pro
                245                 250                 255

Ala Gly Asp Gly Thr Phe Gln Lys Trp Ala Ser Val Val Pro Leu
            260                 265                 270

Gly Lys Glu Gln Tyr Tyr Thr Cys His Val Tyr His Gln Gly Leu Pro
        275                 280                 285

Glu Pro Leu Thr Leu Arg Trp Glu Pro Pro Ser Thr Val Ser Asn
    290                 295                 300

Met Ala Thr Val Ala Val Leu Val Val Leu Gly Ala Ala Ile Val Thr
305                 310                 315                 320

Gly Ala Val Val Ala Phe Val Met Lys Met Arg Arg Arg Asn Thr Gly
                325                 330                 335

Gly Lys Gly Gly Asp Tyr Ala Leu Ala Pro Gly Ser Gln Thr Ser Asp
            340                 345                 350

Leu Ser Leu Pro Asp Cys Lys Val Met Val His Asp Pro His Ser Leu
        355                 360                 365

Ala

<210> SEQ ID NO 11
<211> LENGTH: 368
<212> TYPE: PRT
<213> ORGANISM: Mus musculus

<400> SEQUENCE: 11

Met Ala Pro Cys Thr Leu Leu Leu Leu Ala Ala Ala Leu Ala Pro
1               5                   10                  15

Thr Gln Thr Arg Ala Gly Pro His Ser Leu Arg Tyr Phe Val Thr Ala
                20                  25                  30

Val Ser Arg Pro Gly Leu Gly Glu Pro Arg Phe Ile Ala Val Gly Tyr
            35                  40                  45

Val Asp Asp Thr Gln Phe Val Arg Phe Asp Ser Asp Ala Asp Asn Pro
        50                  55                  60

Arg Phe Glu Pro Arg Ala Pro Trp Met Glu Gln Glu Gly Pro Glu Tyr
65                  70                  75                  80
```

```
Trp Glu Glu Gln Thr Gln Arg Ala Lys Ser Asp Glu Gln Trp Phe Arg
                85                  90                  95

Val Ser Leu Arg Thr Ala Gln Arg Tyr Tyr Asn Gln Ser Lys Gly Gly
            100                 105                 110

Ser His Thr Phe Gln Arg Met Phe Gly Cys Asp Val Gly Ser Asp Trp
        115                 120                 125

Arg Leu Leu Arg Gly Tyr Gln Gln Phe Ala Tyr Asp Gly Arg Asp Tyr
    130                 135                 140

Ile Ala Leu Asn Glu Asp Leu Lys Thr Trp Thr Ala Ala Asp Thr Ala
145                 150                 155                 160

Ala Leu Ile Thr Arg Arg Lys Trp Glu Gln Ala Gly Asp Ala Glu Tyr
                165                 170                 175

Tyr Arg Ala Tyr Leu Glu Gly Glu Cys Val Glu Trp Leu Arg Arg Tyr
            180                 185                 190

Leu Glu Leu Gly Asn Glu Thr Leu Leu Arg Thr Asp Ser Pro Lys Ala
        195                 200                 205

His Val Thr Tyr His Pro Arg Ser Gln Val Asp Val Thr Leu Arg Cys
    210                 215                 220

Trp Ala Leu Gly Phe Tyr Pro Ala Asp Ile Thr Leu Thr Trp Gln Leu
225                 230                 235                 240

Asn Gly Glu Asp Leu Thr Gln Asp Met Glu Leu Val Glu Thr Arg Pro
                245                 250                 255

Ala Gly Asp Gly Thr Phe Gln Lys Trp Ala Ala Val Val Pro Leu
            260                 265                 270

Gly Lys Glu Gln Asn Tyr Thr Cys His Val His His Lys Gly Leu Pro
        275                 280                 285

Glu Pro Leu Thr Leu Arg Trp Lys Leu Pro Pro Ser Thr Val Ser Asn
    290                 295                 300

Thr Val Ile Ile Ala Val Leu Val Val Leu Gly Ala Ala Ile Val Thr
305                 310                 315                 320

Gly Ala Val Val Ala Phe Val Met Lys Met Arg Arg Asn Thr Gly Gly
                325                 330                 335

Lys Gly Val Asn Tyr Ala Leu Ala Pro Gly Ser Gln Thr Ser Asp Leu
            340                 345                 350

Ser Leu Pro Asp Gly Lys Val Met Val His Asp Pro His Ser Leu Ala
        355                 360                 365

<210> SEQ ID NO 12
<211> LENGTH: 360
<212> TYPE: PRT
<213> ORGANISM: Mus musculus

<400> SEQUENCE: 12

Met Ala Pro Cys Met Leu Leu Leu Leu Ala Ala Leu Ala Pro
1               5                   10                  15

Thr Gln Thr Arg Ala Gly Pro His Ser Leu Arg Tyr Phe His Thr Ala
                20                  25                  30

Val Ser Arg Pro Gly Leu Gly Lys Pro Arg Phe Ile Ser Val Gly Tyr
            35                  40                  45

Val Asp Asp Thr Gln Phe Val Arg Phe Asp Ser Asp Ala Glu Asn Pro
        50                  55                  60

Arg Tyr Glu Pro Arg Val Arg Trp Met Glu Gln Val Glu Pro Glu Tyr
65                  70                  75                  80

Trp Glu Arg Asn Thr Gln Ile Ala Lys Gly Asn Glu Gln Ile Phe Arg
                85                  90                  95
```

Val Asn Leu Arg Thr Ala Leu Arg Tyr Tyr Asn Gln Ser Ala Gly Gly
            100                 105                 110

Ser His Thr Phe Gln Arg Met Tyr Gly Cys Glu Val Gly Ser Asp Trp
            115                 120                 125

Arg Leu Leu Arg Gly Tyr Glu Gln Tyr Ala Tyr Asp Gly Cys Asp Tyr
            130                 135                 140

Ile Ala Leu Asn Glu Asp Leu Lys Thr Trp Thr Ala Ala Asp Met Ala
145                 150                 155                 160

Ala Leu Ile Thr Lys His Lys Trp Glu Gln Ala Gly Asp Ala Glu Arg
                165                 170                 175

Asp Arg Ala Tyr Leu Glu Gly Thr Cys Val Glu Trp Leu Arg Arg Tyr
            180                 185                 190

Leu Gln Leu Gly Asn Ala Thr Leu Pro Arg Thr Asp Ser Pro Lys Ala
            195                 200                 205

His Val Thr Arg His Ser Arg Pro Glu Asp Lys Val Thr Leu Arg Cys
            210                 215                 220

Trp Ala Leu Gly Phe Tyr Pro Ala Asp Ile Thr Leu Thr Trp Gln Leu
225                 230                 235                 240

Asn Gly Glu Glu Leu Thr Gln Asp Met Glu Leu Val Glu Thr Arg Pro
                245                 250                 255

Ala Gly Asp Gly Thr Phe Gln Lys Trp Ala Ser Val Val Val Pro Leu
            260                 265                 270

Gly Lys Glu Gln Tyr Tyr Thr Cys His Val Tyr His Gln Gly Leu Pro
            275                 280                 285

Glu Pro Leu Thr Leu Arg Trp Glu Pro Pro Ser Thr Val Ser Asn
            290                 295                 300

Thr Val Ile Ile Ala Val Leu Val Leu Gly Ala Ala Ile Val Thr
305                 310                 315                 320

Gly Ala Val Val Ala Phe Val Met Lys Met Arg Arg Arg Asn Thr Gly
            325                 330                 335

Gly Lys Gly Gly Asp Tyr Ala Leu Ala Pro Gly Ser Gln Thr Ser Asp
            340                 345                 350

Leu Ser Leu Pro Asp Cys Lys Ala
            355                 360

<210> SEQ ID NO 13
<211> LENGTH: 365
<212> TYPE: PRT
<213> ORGANISM: Mus musculus

<400> SEQUENCE: 13

Met Gly Ala Met Ala Pro Arg Thr Leu Leu Leu Leu Ala Ala Ala
1               5                   10                  15

Leu Gly Pro Thr Gln Thr Arg Ala Gly Ser His Ser Leu Arg Tyr Phe
            20                  25                  30

Val Thr Ala Val Ser Arg Pro Gly Phe Gly Glu Pro Arg Tyr Met Glu
            35                  40                  45

Val Gly Tyr Val Asp Asn Thr Glu Phe Val Arg Phe Asp Ser Asp Ala
        50                  55                  60

Glu Asn Pro Arg Tyr Glu Pro Arg Ala Arg Trp Ile Glu Gln Glu Gly
65                  70                  75                  80

Pro Glu Tyr Trp Glu Arg Glu Thr Arg Arg Ala Lys Gly Asn Glu Gln
                85                  90                  95

Ser Phe Arg Val Asp Leu Arg Thr Ala Leu Arg Tyr Tyr Asn Gln Ser

```
                100                 105                 110
Ala Gly Gly Ser His Thr Leu Gln Trp Met Ala Gly Cys Asp Val Glu
            115                 120                 125

Ser Asp Gly Arg Leu Leu Arg Gly Tyr Trp Gln Phe Ala Tyr Asp Gly
130                 135                 140

Cys Asp Tyr Ile Ala Leu Asn Glu Asp Leu Lys Thr Trp Thr Ala Ala
145                 150                 155                 160

Asp Met Ala Ala Gln Ile Thr Arg Arg Lys Trp Glu Gln Ala Gly Ala
            165                 170                 175

Ala Glu Arg Asp Arg Ala Tyr Leu Glu Gly Glu Cys Val Glu Trp Leu
            180                 185                 190

Arg Arg Tyr Leu Lys Asn Gly Asn Ala Thr Leu Leu Arg Thr Asp Pro
            195                 200                 205

Pro Lys Ala His Val Thr His His Arg Pro Glu Gly Asp Val Thr
210                 215                 220

Leu Arg Cys Trp Ala Leu Gly Phe Tyr Pro Ala Asp Ile Thr Leu Thr
225                 230                 235                 240

Trp Gln Leu Asn Gly Glu Glu Leu Thr Gln Glu Met Glu Leu Val Glu
            245                 250                 255

Thr Arg Pro Ala Gly Asp Gly Thr Phe Gln Lys Trp Ala Ser Val Val
            260                 265                 270

Val Pro Leu Gly Lys Glu Gln Lys Tyr Thr Cys His Val Glu His Glu
            275                 280                 285

Gly Leu Pro Glu Pro Leu Thr Leu Arg Trp Gly Lys Glu Pro Pro
290                 295                 300

Ser Ser Thr Lys Thr Asn Thr Val Ile Ile Ala Val Pro Val Val Leu
305                 310                 315                 320

Gly Ala Val Val Ile Leu Gly Ala Val Met Ala Phe Val Met Lys Arg
            325                 330                 335

Arg Arg Asn Thr Gly Gly Lys Gly Gly Asp Tyr Ala Leu Ala Pro Gly
            340                 345                 350

Ser Gln Ser Ser Asp Met Ser Leu Pro Asp Cys Lys Val
            355                 360                 365

<210> SEQ ID NO 14
<211> LENGTH: 362
<212> TYPE: PRT
<213> ORGANISM: Mus musculus

<400> SEQUENCE: 14

Met Gly Ala Met Ala Pro Arg Thr Leu Leu Leu Leu Ala Ala
1               5                   10                  15

Leu Ala Pro Thr Gln Thr Arg Ala Gly Pro His Ser Met Arg Tyr Phe
                20                  25                  30

Glu Thr Ala Val Ser Arg Pro Gly Leu Glu Glu Pro Arg Tyr Ile Ser
            35                  40                  45

Val Gly Tyr Val Asp Asn Lys Glu Phe Val Arg Phe Asp Ser Asp Ala
        50                  55                  60

Glu Asn Pro Arg Tyr Glu Pro Arg Ala Pro Trp Met Glu Gln Glu Gly
65                  70                  75                  80

Pro Glu Tyr Trp Glu Arg Glu Thr Gln Lys Ala Lys Gly Gln Glu Gln
                85                  90                  95

Trp Phe Arg Val Ser Leu Arg Asn Leu Leu Gly Tyr Tyr Asn Gln Ser
                100                 105                 110
```

Ala Gly Gly Ser His Thr Leu Gln Gln Met Ser Gly Cys Asp Leu Gly
            115                 120                 125

Ser Asp Trp Arg Leu Leu Arg Gly Tyr Leu Gln Phe Ala Tyr Glu Gly
        130                 135                 140

Arg Asp Tyr Ile Ala Leu Asn Glu Asp Leu Lys Thr Trp Thr Ala Ala
145                 150                 155                 160

Asp Met Ala Ala Gln Ile Thr Arg Arg Lys Trp Glu Gln Ser Gly Ala
                165                 170                 175

Ala Glu His Tyr Lys Ala Tyr Leu Glu Gly Cys Val Glu Trp Leu
                180                 185                 190

His Arg Tyr Leu Lys Asn Gly Asn Ala Thr Leu Leu Arg Thr Asp Ser
                195                 200                 205

Pro Lys Ala His Val Thr His His Pro Arg Ser Lys Gly Glu Val Thr
        210                 215                 220

Leu Arg Cys Trp Ala Leu Gly Phe Tyr Pro Ala Asp Ile Thr Leu Thr
225                 230                 235                 240

Trp Gln Leu Asn Gly Glu Glu Leu Thr Gln Asp Met Glu Leu Val Glu
                245                 250                 255

Thr Arg Pro Ala Gly Asp Gly Thr Phe Gln Lys Trp Ala Ser Val Val
            260                 265                 270

Val Pro Leu Gly Lys Glu Gln Asn Tyr Thr Cys Arg Val Tyr His Glu
        275                 280                 285

Gly Leu Pro Glu Pro Leu Thr Leu Arg Trp Glu Pro Pro Ser Thr
            290                 295                 300

Asp Ser Tyr Met Val Ile Val Ala Val Leu Gly Val Leu Gly Ala Met
305                 310                 315                 320

Ala Ile Ile Gly Ala Val Val Ala Phe Val Met Lys Arg Arg Arg Asn
                325                 330                 335

Thr Gly Gly Lys Gly Gly Asp Tyr Ala Leu Ala Pro Gly Ser Gln Ser
            340                 345                 350

Ser Glu Met Ser Leu Arg Asp Cys Lys Ala
            355                 360

<210> SEQ ID NO 15
<211> LENGTH: 358
<212> TYPE: PRT
<213> ORGANISM: Mus musculus

<400> SEQUENCE: 15

Met Ala Pro Arg Thr Leu Leu Leu Leu Ala Ala Ala Trp Pro Asp
1               5                   10                  15

Ser Asp Pro Arg Gly Pro His Ser Met Arg Tyr Phe Glu Thr Ala Val
                20                  25                  30

Ser Arg Pro Gly Leu Gly Glu Pro Arg Tyr Ile Ser Val Gly Tyr Val
            35                  40                  45

Asp Asn Lys Glu Phe Val Arg Phe Asp Ser Asp Ala Glu Asn Pro Arg
        50                  55                  60

Tyr Glu Pro Gln Ala Pro Trp Met Glu Gln Glu Gly Pro Glu Tyr Trp
65                  70                  75                  80

Glu Arg Ile Thr Gln Ile Ala Lys Gly Gln Glu Gln Trp Phe Arg Val
                85                  90                  95

Asn Leu Arg Thr Leu Leu Gly Tyr Tyr Asn Gln Ser Ala Gly Gly Thr
            100                 105                 110

His Thr Leu Gln Trp Met Tyr Gly Cys Asp Val Gly Ser Asp Gly Arg
        115                 120                 125

```
Leu Leu Arg Gly Tyr Glu Gln Phe Ala Tyr Asp Gly Arg Asp Tyr Ile
    130                 135                 140

Ala Leu Asn Glu Asp Leu Lys Thr Trp Thr Ala Asp Met Ala Ala
145                 150                 155                 160

Gln Ile Thr Arg Arg Lys Trp Glu Gln Ala Gly Ala Ala Glu Tyr Tyr
                165                 170                 175

Arg Ala Tyr Leu Glu Gly Glu Cys Val Glu Trp Leu His Arg Tyr Leu
                180                 185                 190

Lys Asn Gly Asn Ala Thr Leu Leu Arg Thr Asp Ser Pro Lys Ala His
            195                 200                 205

Val Thr His His Pro Arg Ser Lys Gly Glu Val Thr Leu Arg Cys Trp
    210                 215                 220

Ala Leu Gly Phe Tyr Pro Ala Asp Ile Thr Leu Thr Trp Gln Leu Asn
225                 230                 235                 240

Gly Glu Glu Leu Thr Gln Asp Met Glu Leu Val Glu Thr Arg Pro Ala
                245                 250                 255

Gly Asp Gly Thr Phe Gln Lys Trp Ala Ser Val Val Pro Leu Gly
                260                 265                 270

Lys Glu Gln Asn Tyr Thr Cys Arg Val Tyr His Glu Gly Leu Pro His
            275                 280                 285

Pro Leu Thr Leu Arg Trp Glu Pro Pro Ser Thr Asp Ser Tyr Met
    290                 295                 300

Val Ile Val Ala Val Leu Gly Val Leu Gly Ala Met Ala Ile Ile Gly
305                 310                 315                 320

Ala Val Val Ala Phe Val Met Lys Arg Arg Arg Asn Thr Gly Gly Lys
                325                 330                 335

Gly Gly Asp Tyr Ala Leu Ala Pro Gly Ser Gln Ser Ser Glu Met Ser
            340                 345                 350

Leu Arg Asp Cys Lys Ala
        355

<210> SEQ ID NO 16
<211> LENGTH: 1431
<212> TYPE: DNA
<213> ORGANISM: Artificial
<220> FEATURE:
<223> OTHER INFORMATION: Synthetic

<400> SEQUENCE: 16
atggccgtca tggcgcccg aaccctcgtc ctgctactct cgggggccct ggccctgacc      60
cagacctggg cgatccagcg tactccaaag attcaggttt actcacgtca tccagcagag     120 aatgaaagt caaatttcct gaattgctat gtgtctgggt ttcatccatc cgacattgaa      180
gttgacttac tgaagaatgg agagagaatt gaaaaagtgg agcattcaga cttgtctttc     240
agcaaggact ggtctttcta tctcttgtac tacactgaat tcacccccac tgaaaaagat     300
gagtatgcct gccgtgtgaa ccatgtgact ttgtcacagc ccaagatagt taagtgggat     360
cgagacatgg gaggtggcgg atccggcgga ggcggctcgg gtggcggcgg ctctggatct     420
cactccatga ggtatttctc tcacatccgt gtcccggccg gccgcgggga gccccgcttc     480
atcgccgtgg gctacgtgga cgacacgcag ttcgtgcggt tcgacagcga cgccgcgagc     540
cagaggatgg agccgcgggc gccgtggata gagcaggagg ggccggagta ttgggacgag     600
gagacaggga aagtgaaggc ccactcacag actgaccgag agaacctgcg gatcgcgctc     660
cgctactaca accagagcga ggccggttct cacacctcc agatgatgtt tggctgcgac     720
```

| | |
|---|---|
| gtggggtcgg acgggcgctt cctccgcggg taccaccagt acgcctacga cggcaaggat | 780 |
| tacatcgccc tgaaagagga cctgcgctct tggaccgcgg cggacatggc ggctcagatc | 840 |
| accaagcgca agtgggaggc ggcccatgtg gcggagcagc agagagccta cctggagggc | 900 |
| acgtgcgtgg acgggctccg cagatacctg gagaacggga aggagacgct gcagcgcacg | 960 |
| gattccccaa aggcacatgt gacccatcac cccagatcta aaggtgaagt caccctgagg | 1020 |
| tgctgggccc tgggcttcta ccctgctgac atcaccctga cctggcagtt gaatggggag | 1080 |
| gagctgaccc aggacatgga gcttgtggag accaggcctg caggggatgg aaccttccag | 1140 |
| aagtgggcat ctgtggtggt gcctcttggg aaggagcaga attacacatg ccgtgtgtac | 1200 |
| catgaggggc tgcctgagcc cctcaccctg agatgggagc tcctccgtc cactgactct | 1260 |
| tacatggtga tcgttgctgt tctgggtgtc cttggagcta tggccatcat tggagctgtg | 1320 |
| gtggcttttg tgatgaagag aaggagaaac acaggtggaa aaggagggga ctatgctctg | 1380 |
| gctccaggct cccagagctc tgaaatgtct ctccgagatt gtaaagcgtg a | 1431 |

<210> SEQ ID NO 17
<211> LENGTH: 1431
<212> TYPE: DNA
<213> ORGANISM: Artificial
<220> FEATURE:
<223> OTHER INFORMATION: Synthetic

<400> SEQUENCE: 17

| | |
|---|---|
| atggccgtca tggcgccccg aaccctcgtc ctgctactct cgggggccct ggccctgacc | 60 |
| cagacctggg cgatccagcg tactccaaag attcaggttt actcacgtca tccagcagag | 120 |
| aatggaaagt caaatttcct gaattgctat gtgtctgggt tcatccatc cgacattgaa | 180 |
| gttgacttac tgaagaatgg agagagaatt gaaaaagtgg agcattcaga cttgtctttc | 240 |
| agcaaggact ggtctttcta tctcttgtac tacactgaat tcacccccac tgaaaaagat | 300 |
| gagtatgcct gccgtgtgaa ccatgtgact ttgtcacagc caagatagt taagtgggat | 360 |
| cgagacatgg gaggtggcgg atccggcgga ggcggctcgg gtggcggcgg ctctggatct | 420 |
| cactccatga ggtatttctt cacatccgtg tccggcccg gccgcgggga gccccgcttc | 480 |
| atcgccgtgg gctacgtgga cgacacgcag ttcgtgcggt tcgacagcga cgccgcgagc | 540 |
| cagaggatgg agccgcgggc gccgtggata gagcaggagg ggccggagta ttgggaccag | 600 |
| gagacacgga atgtgaaggc ccagtcacag actgaccgag tggacctggg gaccctgcgc | 660 |
| ggctactaca accagagcga ggccggttct cacaccatcc agataatgta tggctgcgac | 720 |
| gtggggtcgg acgggcgctt cctccgcggg taccggcagg acgcctacga cggcaaggat | 780 |
| tacatcgccc tgaacgagga cctgcgctct tggaccgcgg cggacatggc ggctcagatc | 840 |
| accaagcgca agtgggaggc ggcccatgag gcggagcagt gagagccta cctggatggc | 900 |
| acgtgcgtgg agtggctccg cagatacctg gagaacggga aggagacgct gcagcgcacg | 960 |
| gattccccaa aggcacatgt gacccatcac cccagatcta aaggtgaagt caccctgagg | 1020 |
| tgctgggccc tgggcttcta ccctgctgac atcaccctga cctggcagtt gaatggggag | 1080 |
| gagctgaccc aggacatgga gcttgtggag accaggcctg caggggatgg aaccttccag | 1140 |
| aagtgggcat ctgtggtggt gcctcttggg aaggagcaga attacacatg ccgtgtgtac | 1200 |
| catgaggggc tgcctgagcc cctcaccctg agatgggagc tcctccgtc cactgactct | 1260 |
| tacatggtga tcgttgctgt tctgggtgtc cttggagcta tggccatcat tggagctgtg | 1320 |

```
gtggcttttg tgatgaagag aaggagaaac acaggtggaa aaggagggga ctatgctctg    1380
gctccaggct cccagagctc tgaaatgtct ctccgagatt gtaaagcgtg a             1431
```

<210> SEQ ID NO 18
<211> LENGTH: 68
<212> TYPE: DNA
<213> ORGANISM: Artificial
<220> FEATURE:
<223> OTHER INFORMATION: Primer

<400> SEQUENCE: 18

```
ggatccggcg gaggcggctc gggtggcggc ggcggctctg gatctcccac tccatgaggt    60
atttctcc                                                             68
```

<210> SEQ ID NO 19
<211> LENGTH: 29
<212> TYPE: DNA
<213> ORGANISM: Artificial
<220> FEATURE:
<223> OTHER INFORMATION: Primer

<400> SEQUENCE: 19

```
agatctacag gcgatcaggt aggcgcccc                                      29
```

<210> SEQ ID NO 20
<211> LENGTH: 94
<212> TYPE: DNA
<213> ORGANISM: Artificial
<220> FEATURE:
<223> OTHER INFORMATION: Primer

<400> SEQUENCE: 20

```
ccatggccgt catggcgccc cgaaccctcg tcctgctact ctcggggcc ctgacccaga     60 cctgggcgat ccagcgtact ccaaagattc aggt                                94
```

<210> SEQ ID NO 21
<211> LENGTH: 40
<212> TYPE: DNA
<213> ORGANISM: Artificial
<220> FEATURE:
<223> OTHER INFORMATION: Primer

<400> SEQUENCE: 21

```
ggatccgcca cctccactgt ctcgatccca cttaactatc                          40
```

<210> SEQ ID NO 22
<211> LENGTH: 30
<212> TYPE: DNA
<213> ORGANISM: Artificial
<220> FEATURE:
<223> OTHER INFORMATION: Primer

<400> SEQUENCE: 22

```
ggatcctgtg tgacatacct gtaccttgtc                                     30
```

<210> SEQ ID NO 23
<211> LENGTH: 38
<212> TYPE: DNA
<213> ORGANISM: Artificial
<220> FEATURE:
<223> OTHER INFORMATION: Primer

<400> SEQUENCE: 23

```
atttaaatct agttgagtct ctgatcttta gccctagg                            38
```

<210> SEQ ID NO 24
<211> LENGTH: 36
<212> TYPE: DNA
<213> ORGANISM: Artificial
<220> FEATURE:
<223> OTHER INFORMATION: Primer

<400> SEQUENCE: 24
gtcgacctgg gtagacactg taggattggg tctctg                              36

<210> SEQ ID NO 25
<211> LENGTH: 30
<212> TYPE: DNA
<213> ORGANISM: Artificial
<220> FEATURE:
<223> OTHER INFORMATION: Primer

<400> SEQUENCE: 25
ccatggtgac gactgaagcg accgcgactg                                     30

<210> SEQ ID NO 26
<211> LENGTH: 35
<212> TYPE: DNA
<213> ORGANISM: Artificial
<220> FEATURE:
<223> OTHER INFORMATION: Primer

<400> SEQUENCE: 26
agcatttcct agtacagttc aacacagtgt ttagt                               35

<210> SEQ ID NO 27
<211> LENGTH: 30
<212> TYPE: DNA
<213> ORGANISM: Artificial
<220> FEATURE:
<223> OTHER INFORMATION: Primer

<400> SEQUENCE: 27
gagtagcagg acgagggttc ggggcgccat                                     30

<210> SEQ ID NO 28
<211> LENGTH: 25
<212> TYPE: DNA
<213> ORGANISM: Artificial
<220> FEATURE:
<223> OTHER INFORMATION: Primer

<400> SEQUENCE: 28
ctagaagcaa ggtcagaaat cctct                                          25

<210> SEQ ID NO 29
<211> LENGTH: 25
<212> TYPE: DNA
<213> ORGANISM: Artificial
<220> FEATURE:
<223> OTHER INFORMATION: Primer

<400> SEQUENCE: 29
ccgtcagcac actcgcaaac aggcg                                          25

<210> SEQ ID NO 30
<211> LENGTH: 30
<212> TYPE: DNA
<213> ORGANISM: Artificial
<220> FEATURE:

<223> OTHER INFORMATION: Primer

<400> SEQUENCE: 30
gagtagcagg acgagggttc ggggcgccat                                30

<210> SEQ ID NO 31
<211> LENGTH: 867
<212> TYPE: DNA
<213> ORGANISM: Artificial
<220> FEATURE:
<223> OTHER INFORMATION: Synthetic

<400> SEQUENCE: 31

```
ggatccggcg gaggcggctc gggtggcggc ggctctggat ctcactccat gaggtatttc    60
ttcacatccg tgtcccggcc cggccgcggg gagccccgct tcatcgccgt gggctacgtg   120
gacgacacgc agttcgtgcg gttcgacagc gacgccgcga gccagaggat ggagccgcgg   180
gcgccgtgga tagagcagga ggggccggag tattgggacc aggagacacg gaatgtgaag   240
gcccagtcac agactgaccg agtggacctg ggaccctgc gcggctacta caaccagagc   300
gaggccggtg agtgaccccg gccggtggcg caggtcagga cccctcatcc cccacggacg   360
ggccaggtcg cccacagtct ccgggtccga gatccacccc gaagccgcgg gaccccgaga   420
cccttgcccc gggagaggcc caggcgcctt tacccggttt cattttcagt ttaggccaaa   480
aatcccccg ggttggtcgg ggctgggcgg ggctcggggg actgggctga ccgcggggtc   540
ggggccaggt tctcacacca tccagataat gtatggctgc gacgtggggt cggacgggcg   600
cttcctccgc gggtaccggc aggacgccta cgacggcaag gattacatcg ccctgaacga   660
ggacctgcgc tcttggaccg cggcggacat ggcggctcag atcaccaagc gcaagtggga   720
ggcggcccat gaggcggagc agttgagagc ctacctggat ggcacgtgcg tggagtggct   780
ccgcagatac ctggagaacg ggaaggagac gctgcagcgc acgggtacca ggggccacgg   840
ggcgcctccc tgatcgcctg tagatct                                       867
```

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Glu Tyr Leu Val Ser Phe Gly Val Trp
1               5

<210> SEQ ID NO 33
<211> LENGTH: 9
<212> TYPE: PRT
<213> ORGANISM: Artificial
<220> FEATURE:
<223> OTHER INFORMATION: Synthetic

<400> SEQUENCE: 33

Ser Phe His Ser Leu His Leu Leu Phe
1               5

<210> SEQ ID NO 34
<211> LENGTH: 10
<212> TYPE: PRT
<213> ORGANISM: Artificial
<220> FEATURE:
<223> OTHER INFORMATION: Synthetic

```
<400> SEQUENCE: 34

Asp Tyr Cys Asn Val Leu Asn Lys Glu Phe
1               5                   10

<210> SEQ ID NO 35
<211> LENGTH: 9
<212> TYPE: PRT
<213> ORGANISM: Artificial
<220> FEATURE:
<223> OTHER INFORMATION: Synthetic

<400> SEQUENCE: 35

Arg Tyr Leu Arg Asp Gln Gln Leu Leu
1               5

<210> SEQ ID NO 36
<211> LENGTH: 9
<212> TYPE: PRT
<213> ORGANISM: Artificial
<220> FEATURE:
<223> OTHER INFORMATION: Synthetic

<400> SEQUENCE: 36

Arg Leu Arg Pro Gly Gly Lys Lys Lys
1               5

<210> SEQ ID NO 37
<211> LENGTH: 10
<212> TYPE: PRT
<213> ORGANISM: Artificial
<220> FEATURE:
<223> OTHER INFORMATION: Synthetic

<400> SEQUENCE: 37

Gln Val Pro Leu Arg Pro Met Thr Tyr Lys
1               5                   10

<210> SEQ ID NO 38
<211> LENGTH: 9
<212> TYPE: PRT
<213> ORGANISM: Artificial
<220> FEATURE:
<223> OTHER INFORMATION: Synthetic

<400> SEQUENCE: 38

Arg Leu Arg Ala Glu Ala Gln Val Lys
1               5

<210> SEQ ID NO 39
<211> LENGTH: 8
<212> TYPE: PRT
<213> ORGANISM: Artificial
<220> FEATURE:
<223> OTHER INFORMATION: Synthetic

<400> SEQUENCE: 39

Ser Ile Ile Pro Gly Pro Leu Lys
1               5

<210> SEQ ID NO 40
<211> LENGTH: 57
<212> TYPE: DNA
<213> ORGANISM: Homo sapiens

<400> SEQUENCE: 40
```

```
atggcgcccc gaaccctcgt cctgctactc tcggggccc tgacccagac ctgggcg      57
```

<210> SEQ ID NO 41
<211> LENGTH: 1431
<212> TYPE: DNA
<213> ORGANISM: Artificial
<220> FEATURE:
<223> OTHER INFORMATION: Synthetic

<400> SEQUENCE: 41

```
atggccgtca tggcgcccg aaccctcgtc ctgctactct cggggccct ggccctgacc      60
cagacctggg cgatccagcg tactccaaag attcaggttt actcacgtca tccagcagag     120
aatggaaagt caaatttcct gaattgctat gtgtctgggt ttcatccatc cgacattgaa     180
gttgacttac tgaagaatgg agagagaatt gaaaaagtgg agcattcaga cttgtctttc     240
agcaaggact ggtcttttcta tctcttgtac tacactgaat tcaccccca ctgaaaaagat     300
gagtatgcct gccgtgtgaa ccatgtgact ttgtcacagc caagatagt taagtgggat     360
cgagacatgg gaggtggcgg atccggcgga ggcggctcgg gtggcggcgg ctctggatct     420
cactccatga ggtatttctt cacatccgtg tcccggcccg gccgcgggga gccccgcttc     480
atcgcagtgg gctacgtgga cgacacgcag ttcgtgcgt tcgacagcga cgccgcgagc     540
cagaggatgg agccgcgggc gccgtggata gagcaggagg gtccggagta ttgggacggg     600
gagacacgga aagtgaaggc ccactcacag actcaccgag tggacctggg gaccctgcgc     660
ggctactaca accagagcga ggccggttct cacaccgtcc agaggatgta tggctgcgac     720
gtggggtcgg actggcgctt cctccgcggg taccaccagt acgcctacga cggcaaggat     780
tacatcgccc tgaaagagga cctgcgctct tggaccgcgg cggacatggc agctcagacc     840
accaagcaca gtgggaggc ggcccatgtg gcggagcagt tgagagccta cctggagggc     900
acgtgcgtgg agtggctccg cagatacctg gagaacggga aggagacgct gcagcgcacg     960
gattccccaa aggcacatgt gacccatcac cccagatcta aaggtgaagt caccctgagg    1020
tgctgggccc tgggcttcta ccctgctgac atcaccctga cctggcagtt gaatggggag    1080
gagctgaccc aggacatgga gcttgtggag accaggcctg caggggatgg aaccttccag    1140
aagtgggcat ctgtggtggt gcctcttggg aaggagcaga attacacatg ccgtgtgtac    1200
catgagggc tgcctgagcc cctcacctg agatgggagc tcctccgtc cactgactct    1260
tacatggtga tcgttgctgt tctgggtgtc cttggagcta tggccatcat tggagctgtg    1320
gtggcttttg tgatgaagag aaggagaaac acaggtggaa aaggagggga ctatgctctg    1380
gctccaggct cccagagctc tgaaatgtct ctccgagatt gtaaagcgtg a              1431
```

<210> SEQ ID NO 42
<211> LENGTH: 1431
<212> TYPE: DNA
<213> ORGANISM: Artificial
<220> FEATURE:
<223> OTHER INFORMATION: Synthetic

<400> SEQUENCE: 42

```
atggccgtca tggcgcccg aaccctcgtc ctgctactct cggggccct ggccctgacc      60
cagacctggg cgatccagcg tactccaaag attcaggttt actcacgtca tccagcagag     120
aatggaaagt caaatttcct gaattgctat gtgtctgggt ttcatccatc cgacattgaa     180
gttgacttac tgaagaatgg agagagaatt gaaaaagtgg agcattcaga cttgtctttc     240
agcaaggact ggtcttttcta tctcttgtac tacactgaat tcaccccca ctgaaaaagat     300
```

```
gagtatgcct gccgtgtgaa ccatgtgact ttgtcacagc ccaagatagt taagtgggat    360
cgagacatgg gaggtggcgg atccggcgga ggcggctcgg gtggcggcgg ctctggatct    420
cactccatga ggtatttcac acatccgtg tcccggcccg ccgcgggga gccccgcttc     480 atcgccgtgg gctacgtgga cgacacgcag ttcgtgcgt tcgacagcga cgccgcgagc    540
cagaggatgg agccgcgggc gccgtggata gagcaggaga ggcctgagta ttgggaccag    600
gagacacgga atgtgaaggc ccactcacag attgaccgag tggacctggg accctgcgc    660 ggctactaca accagagcga ggccggttct cacaccatcc agatgatgta tggctgcgac    720
gtggggtcgg acgggcgctt cctccgcggg taccagcagg acgcctacga cggcaaggat    780
tacatcgcct tgaacgagga cctgcgctct tggaccgcgg cggacatggc ggctcagatc    840
acccagcgca gtgggaggc ggcccgtgtg gcggagcagt tgagagccta cctggagggc    900
acgtgcgtgg agtggctccg cagatacctg gagaacggga aggagacgct gcagcgcacg    960
gattccccaa aggcacatgt gacccatcac cccagatcta aggtgaagt cacccctgagg    1020 tgctgggccc tgggcttcta ccctgctgac atcaccctga cctggcagtt gaatggggag    1080
gagctgaccc aggacatgga gcttgtggag accaggcctg caggggatgg aaccttccag    1140
aagtgggcat ctgtggtggt gcctcttggg aaggagcaga attacacatg ccgtgtgtac    1200 catgagggggc tgcctgagcc cctcaccctg agatgggagc ctcctccgtc cactgactct    1260
tacatggtga tcgttgctgt tctgggtgtc cttggagcta tggccatcat tggagctgtg    1320
gtggcttttg tgatgaagag aaggagaaac acaggtggaa aaggagggga ctatgctctg    1380
gctccaggct cccagagctc tgaaatgtct ctccgagatt gtaaagcgtg a             1431

<210> SEQ ID NO 43
<211> LENGTH: 867
<212> TYPE: DNA
<213> ORGANISM: Artificial
<220> FEATURE:
<223> OTHER INFORMATION: Synthetic

<400> SEQUENCE: 43
ggatccggcg gaggcggctc gggtggcggc ggctctggat ctcactccat gaggtatttc     60
ttcacatccg tgtcccggcc cggccgcggg gagccccgct tcatcgcagt gggctacgtg    120
gacgacacgc agttcgtgcg gttcgacagc gacgccgcga gccagaggat ggagccgcgg    180
gcgccgtgga tagagcagga gggtccggag tattgggacg gggagacacg gaaagtgaag    240
gcccactcac agactcaccg agtggacctg ggaccctgc gcggctacta caaccagagc    300
gaggccggtg agtgaccccg gccggtggcg caggtcagga cccctcatcc cccacggacg    360
ggccaggtcg cccacagtct ccgggtccga gatccacccc gaagccgcgg gaccccgaga    420 ccccttgcccc gggagaggcc caggcgcctt tacccggttt cattttcagt ttaggccaaa    480
aatccccccg ggttggtcgg ggctgggcgg ggctcggggg actgggctga ccgcggggtc    540
ggggccaggt tctcacaccg tccagaggat gtatggctgc gacgtggggt cggactggcg    600
cttcctccgc gggtaccacc agtacgccta cgacggcaag gattacatcg ccctgaaaga    660
ggacctgcgc tcttggaccg cggcggacat ggcagctcag accaccaagc acaagtggga    720
ggcggcccat gtggcggagc agttgagagc ctacctggag ggcacgtgcg tggagtggct    780
ccgcagatac ctggagaacg ggaaggagac gctgcagcgc acgggtacca ggggccacgg    840
ggcgcctccc tgatcgcctg tagatct                                         867
```

<210> SEQ ID NO 44
<211> LENGTH: 867
<212> TYPE: DNA
<213> ORGANISM: Artificial
<220> FEATURE:
<223> OTHER INFORMATION: Synthetic

<400> SEQUENCE: 44

```
ggatccggcg gaggcggctc gggtggcggc ggctctggat ctcactccat gaggtatttc      60
accacatccg tgtcccggcc cggccgcggg gagccccgct tcatcgccgt gggctacgtg     120
gacgacacgc agttcgtgcg gttcgacagc gacgccgcga gccagaggat ggagccgcgg     180
gcgccgtgga tagagcagga gaggcctgag tattgggacc aggagacacg gaatgtgaag     240
gcccactcac agattgaccg agtggacctg gggaccctgc gcggctacta caaccagagc     300
gaggccggtg agtgaccccg gccggtggcg caggtcagga cccctcatcc cccacggacg     360
ggccaggtcg cccacagtct ccgggtccga gatccacccc gaagccgcgg acccccgaga     420
cccttgcccc gggagaggcc caggcgcctt tacccggttt cattttcagt ttaggccaaa     480
aatccccccg ggttggtcgg ggctgggcgg ggctcggggg actgggctga ccgcggggtc     540
ggggccaggt tctcacacca tccagatgat gtatggctgc gacgtggggt cggacgggcg     600
cttcctccgc gggtaccagc aggacgccta cgacggcaag gattacatcg ccttgaacga     660
ggacctgcgc tcttggaccg cggcggacat ggcggctcag atcacccagc gcaagtggga     720
ggcggcccgt gtggcggagc agttgagagc ctacctggag ggcacgtgcg tggagtggct     780
ccgcagatac ctggagaacg ggaaggagac gctgcagcgc acgggtacca ggggccacgg     840
ggcgcctccc tgatcgcctg tagatct                                         867
```

<210> SEQ ID NO 45
<211> LENGTH: 9
<212> TYPE: PRT
<213> ORGANISM: Artificial
<220> FEATURE:
<223> OTHER INFORMATION: Synthetic

<400> SEQUENCE: 45

Cys Leu Gly Gly Leu Leu Thr Met Val
1               5

<210> SEQ ID NO 46
<211> LENGTH: 9
<212> TYPE: PRT
<213> ORGANISM: Artificial
<220> FEATURE:
<223> OTHER INFORMATION: Synthetic

<400> SEQUENCE: 46

Gly Leu Cys Thr Leu Val Ala Met Leu
1               5

<210> SEQ ID NO 47
<211> LENGTH: 9
<212> TYPE: PRT
<213> ORGANISM: Artificial
<220> FEATURE:
<223> OTHER INFORMATION: Synthetic

<400> SEQUENCE: 47

Asn Leu Val Pro Met Val Ala Thr Val
1               5

```
<210> SEQ ID NO 48
<211> LENGTH: 9
<212> TYPE: PRT
<213> ORGANISM: Artificial
<220> FEATURE:
<223> OTHER INFORMATION: Synthetic

<400> SEQUENCE: 48

Val Leu Ala Glu Leu Val Lys Gln Ile
1               5

<210> SEQ ID NO 49
<211> LENGTH: 9
<212> TYPE: PRT
<213> ORGANISM: Artificial
<220> FEATURE:
<223> OTHER INFORMATION: Synthetic

<400> SEQUENCE: 49

Val Leu Ser Asp Phe Lys Thr Trp Leu
1               5

<210> SEQ ID NO 50
<211> LENGTH: 10
<212> TYPE: PRT
<213> ORGANISM: Artificial
<220> FEATURE:
<223> OTHER INFORMATION: Synthetic

<400> SEQUENCE: 50

Phe Leu Pro Ser Asp Phe Phe Pro Ser Val
1               5                   10

<210> SEQ ID NO 51
<211> LENGTH: 9
<212> TYPE: PRT
<213> ORGANISM: Artificial
<220> FEATURE:
<223> OTHER INFORMATION: Synthetic

<400> SEQUENCE: 51

Phe Leu Leu Thr Arg Ile Leu Thr Ile
1               5

<210> SEQ ID NO 52
<211> LENGTH: 9
<212> TYPE: PRT
<213> ORGANISM: Artificial
<220> FEATURE:
<223> OTHER INFORMATION: Synthetic

<400> SEQUENCE: 52

Gly Leu Ser Pro Thr Val Trp Leu Ser
1               5

<210> SEQ ID NO 53
<211> LENGTH: 10
<212> TYPE: PRT
<213> ORGANISM: Artificial
<220> FEATURE:
<223> OTHER INFORMATION: Synthetic

<400> SEQUENCE: 53

Ala Ser Cys Met Gly Leu Ile Tyr Asn Arg
1               5                   10
```

```
<210> SEQ ID NO 54
<211> LENGTH: 10
<212> TYPE: PRT
<213> ORGANISM: Artificial
<220> FEATURE:
<223> OTHER INFORMATION: Synthetic

<400> SEQUENCE: 54

Ser Val Gln Pro Thr Phe Ser Val Gln Arg
1               5                   10

<210> SEQ ID NO 55
<211> LENGTH: 10
<212> TYPE: PRT
<213> ORGANISM: Artificial
<220> FEATURE:
<223> OTHER INFORMATION: Synthetic

<400> SEQUENCE: 55

Lys Phe Leu Pro Asp Leu Tyr Asp Tyr Lys
1               5                   10

<210> SEQ ID NO 56
<211> LENGTH: 10
<212> TYPE: PRT
<213> ORGANISM: Artificial
<220> FEATURE:
<223> OTHER INFORMATION: Synthetic

<400> SEQUENCE: 56

Ser Phe Ser Phe Gly Gly Phe Thr Phe Lys
1               5                   10

<210> SEQ ID NO 57
<211> LENGTH: 10
<212> TYPE: PRT
<213> ORGANISM: Artificial
<220> FEATURE:
<223> OTHER INFORMATION: Synthetic

<400> SEQUENCE: 57

Arg Val Ile Asp Pro Arg Arg Cys Met Lys
1               5                   10
```

HLA CLASS I-EXPRESSING NON-HUMAN ANIMAL

CROSS-REFERENCE TO RELATED APPLICATIONS

This application is a National Stage application of PCT/JP2014/077668, filed Oct. 17, 2014, which claims priority to Japanese application JP 2013-217684, filed Oct. 18, 2013.

TECHNICAL FIELD

The present invention relates to an HLA class I-expressing non-human animal, a method for producing the same, and applications thereof. More particularly, the present invention relates to an HLA class I gene knock-in non-human animal or non-human cell in which an artificial chimeric gene encoding an artificial chimeric protein comprising a protein composed of β2 microglobulin, HLA class I α1 and α2 regions, and an MHC class I α3 region of a non-human animal ligated in such order from the N terminus is expressed under the control of a transcription regulatory region of β2 microglobulin gene of the non-human animal, a derivative thereof, and a method for using the same.

BACKGROUND ART

The major histocompatibility complex (MHC) plays a key role in the defense mechanism of a body induced by T cell immunoresponses by presenting a cancer- or virus-derived antigen peptide. MHC is classified as class I or class II, and class I is expressed in all somatic cells except for germ cells and erythrocytes. MHC class I is composed of an α chain and a β chain, and the α chain is composed of α1 and α2 regions associated with the formation of an antigen peptide-holding groove and an α3 region associated with the binding to a co-receptor CD8 molecule expressed on the cytotoxic T cell (CTL) surface. In contrast, the β chain of MHC class I is encoded by β2 microglobulin gene (Non-Patent Document 1).

The cytotoxic T cell (CTL) is known to be activated by recognizing a complex of an MHC class I molecule and an antigen peptide existing on the antigen presenting cell (APC) surface with the aid of a T cell receptor and it is known to specifically damage cancer cells or virus-infected cells expressing the same complexes. With the use of such cell-mediated immune mechanism, the development of vaccines used for cancer immunotherapy or treatment of infections has been attempted.

MHC class I (H-2 class I) of mice that are commonly used as experimental animals is different from MHC class I (HLA class I) of humans. Thus, mice cannot be used as in vivo evaluation models for the development of human vaccines. Thus, human HLA genes containing a promoter region or recombinant genes comprising the HLA genes inserted into sites downstream of a mouse H2 promoter region have been injected into fertilized mouse eggs, so as to prepare various transgenic mice expressing human HLA class I molecules (Non-Patent Documents 2 and 3). However, such transgenic mice were not capable of sufficiently recognizing the α3 region of human HLA class I with the use of mouse CD8. Thus, HLA-restricted CTL induction was limited. In order to overcome such problems, a chimeric gene comprising HLA class I α1/α2 fused to mouse H-2 class I α3 was inserted into a site downstream of SV 40 promoter to construct transgenic mice (Non-Patent Document 4), and in vivo evaluation of HLA-restricted CTL induction became feasible for the first time.

In such transgenic mice, however, endogenous mouse H-2 class I is expressed. When mouse CTL recognizes an antigen, it preferentially uses the H-2 class I molecule. Thus, HLA class I-restricted CTL induction was incomplete. In order to overcome this problem, double knockout mice for mouse H-2 class I α molecules (H-2$K^b$ and H-2$D^b$) were subjected to crossing with transgenic mice comprising HLA class I chimeric genes, so as to construct combined mutant mice and improve HLA class I-restricted CTL induction (Non-Patent Document 5).

The β2 microglobulin gene constituting the MHC class I β chain is essential for the MHC class I molecule to function. Thus, functions of mouse MHC class I are lost in β2 microglobulin gene-deficient mice (Non-Patent Documents 6 and 7). In addition, a single-chain fusion gene resulting from the binding between the C terminus of β2 microglobulin and the N terminus of MHC class I with the aid of a peptide linker consisting of 15 amino acids is known to function normally in cells (Non-Patent Document 8).

An artificial MHC class I gene comprising β2 microglobulin, HLA class I α1 and α2 domains, and the mouse H-2 class I α3 domain fused to each other was inserted into a site downstream of HLA class I gene promoter, so as to construct transgenic mice. The resulting transgenic mice were subjected to crossing with the β2 microglobulin gene knockout mice, so as to construct combined mutant mice (Non-Patent Document 9). In such mice, H-2 class I expression was substantially lost and HLA class I-restricted CTL induction reaction was observed. Accordingly, such mice are considered to be the most preferable MHC class I humanized mouse at present.

In recent years, the MHC class I humanized mouse was subjected to crossing with more severely immunodeficient animals (i.e., NOD/SCID/gamma-c-null (NOG) mice), and human blood stem cells were implanted into the resulting multiple mutant mice. Thus, human-adaptive immune systems having complete HLA-restricted T cells can be reconstructed (Non-Patent Document 10). By subjecting the MHC class I humanized mouse to crossing with other mutant lines, the resulting mice may become useful for the production of superior animal models of human immune systems.

However, transgene expression in artificial MHC class I gene transgenic mice that have been constructed in the past is considered to be influenced by various factors such as copy number, site of insertion in the genome, or epigenetic modification. This required the selection of mouse lines showing optimal expression levels from among constructed transgenic mouse lines. For the same reasons, it has been difficult to compare the capacity of CTL induction among transgenic mouse lines expressing different MHC class I genes.

In order to enhance human MHC class I-restricted CTL induction, it has been necessary to subject the selected mouse lines to crossing with the β2 microglobulin gene deficient mice. Accordingly, additional time and labor has been required, after selection of transgenic mouse lines showing the optimal expression levels.

While the MHC class I humanized mouse has been very useful, the transgenic mouse lines thereof that have been heretofore constructed have been limited to A1, A2, A24, A11, B44, and B7 for the reasons described above. The production of combined mutant mice via crossing of the MHC class I humanized mouse and the β2 microglobulin gene knockout mice has been further limited.

PRIOR ART DOCUMENTS

Non-Patent Documents

Non-Patent Document 1: Human Vaccines 4: 6, 400-409; November/December 2008
Non-Patent Document 2: Eur. J. Immunol., September, 1989; 19 (9): 1575-83
Non-Patent Document 3: J. Immunol., Feb. 15, 1989; 142 (4): 1366-71
Non-Patent Document 4: J. Exp. Med., Apr. 1, 1991; 173 (4): 1007-15
Non-Patent Document 5: J. Immunol., 1999, 163: 2555-60
Non-Patent Document 6: Nature, Apr. 19, 1990; 344 (6268): 742-6
Non-Patent Document 7: Science, Vol. 248, Jun. 8, 1990: 1227-30
Non-Patent Document 8: Proc. Natl., Acad. Sci., U.S.A., Nov. 15, 1992; 89 (22): 10658-62
Non-Patent Document 9: J. Exp. Med., Jun. 16, 1997; 185 (12): 2043-51
Non-Patent Document 10: Proc. Natl. Acad. Sci., U.S.A., Jul. 20, 2010; 107 (29): 13022-7

SUMMARY OF THE INVENTION

Problems to be Solved by the Invention

It is an object of the present invention to provide an HLA class I-expressing non-human animal that resolves the problems described above and a method for preparing the same.
Specifically, the present invention provides an HLA class I-expressing non-human animal, which can be prepared efficiently and readily within a short period of time, and in which the copy number of transgenes, the positions of gene introduction, the gene expression levels, and the sites of gene expression are regulated, and a method for preparing the same.

Means for Solving the Problem

The present inventors have conducted concentrated studies in order to solve the above problem, and, as a result, they discovered the following. That is, an artificial chimeric gene that encodes an artificial chimeric protein comprising a protein composed of β2 microglobulin, HLA class I α1 and α2 regions, and an MHC class I α3 region of a non-human animal ligated in such order from the N terminus may be allowed to express under the control of a transcription regulatory region of β2 microglobulin gene of the non-human animal, so that an HLA class I gene knock-in non-human animal can be prepared efficiently and readily within a short period of time. In addition, the copy number of artificial chimeric genes to be introduced and the positions at which genes are introduced into the HLA class I gene knock-in non-human animal prepared by such method can be regulated, and the gene expression levels and the sites of gene expression can be regulated. This has led to the completion of the present invention.
Specifically, the present invention includes the following.
[1] An HLA class I gene knock-in non-human animal in which an artificial chimeric gene encoding an artificial chimeric protein comprising a protein composed of β2 microglobulin, HLA class I α1 and α2 regions, and an MHC class I α3 region of the non-human animal ligated in such order from the N terminus is expressed under the control of a transcription regulatory region of β2 microglobulin gene of the non-human animal.
[2] The HLA class I gene knock-in non-human animal according to [1], wherein the artificial chimeric gene is expressed under the control of the transcription regulatory region of β2 microglobulin gene in one locus of a pair of β2 microglobulin loci of the non-human animal.
[3] The HLA class I gene knock-in non-human animal according to [1] or [2], wherein the HLA class I α1 and α2 regions are derived from HLA-A.
[4] The HLA class I gene knock-in non-human animal according to [3], wherein the HLA-A is HLA-A24, HLA-A3, HLA-A2, or HLA-A31.
[5] The HLA class I gene knock-in non-human animal according to [3], wherein the HLA-A is HLA-A2402, HLA-A0301, HLA-A0201, or HLA-A3101.
[6] The HLA class I gene knock-in non-human animal according to [1], wherein the first artificial chimeric gene encoding the first artificial chimeric protein comprising a protein composed of β2 microglobulin, HLA class I α1 and α2 regions, and an MHC class I α3 region of the non-human animal ligated in such order from the N terminus is expressed under the control of the transcription regulatory region of β2 microglobulin gene in the first gene locus of the pair of β2 microglobulin loci of the non-human animal;
and the second artificial chimeric gene encoding the second artificial chimeric protein comprising a protein composed of β2 microglobulin, HLA class I α1 and 02 regions, and an MHC class I α3 region of the non-human animal ligated in such order from the N terminus is expressed under the control of the transcription regulatory region of β2 microglobulin gene in the other gene locus, which is the second gene locus of the pair of β2 microglobulin loci of the non-human animal.
[7] The HLA class I gene knock-in non-human animal according to [6], wherein the HLA class I α1 and α2 regions of the first artificial chimeric protein and the HLA class I α1 and α2 regions of the second artificial chimeric protein are derived from HLA of the same genotype.
[8] The HLA class I gene knock-in non-human animal according to [6], wherein the HLA class I α1 and α2 regions of the first artificial chimeric protein and the HLA class I α1 and α2 regions of the second artificial chimeric protein are derived from HLA of different genotypes.
[9] The HLA class I gene knock-in non-human animal according to any of [6] to [8], wherein the HLA class I α1 and α2 regions of the first artificial chimeric protein and the HLA class I α1 and α2 regions of the second artificial chimeric protein are derived from HLA-A.
[10] The HLA class I gene knock-in non-human animal according to [9], wherein the HLA class I α1 and α2 regions of the first artificial chimeric protein and the HLA class I α1 and α2 regions of the second artificial chimeric protein, the same or different, are derived from HLA-A24, HLA-A3, HLA-A2, or HLA-A31.
[11] The HLA class I gene knock-in non-human animal according to [9], wherein the HLA class I α1 and α2 regions of the first artificial chimeric protein and the HLA class I α1 and α2 regions of the second artificial chimeric protein, the same or different, are derived from HLA-A2402, HLA-A0301, HLA-A0201, or HLA-A3101.
[12] The HLA class I gene knock-in non-human animal according to any of [1] to [11], wherein the MHC class I α3 region of the non-human animal is derived from H-2 class I.

[13] The HLA class I gene knock-in non-human animal according to [12], wherein the MHC class I α3 region of the non-human animal is derived from H-2D$^b$.

[14] The HLA class I gene knock-in non-human animal according to any of [1] to [13], wherein the β2 microglobulin is human β2 microglobulin.

[15] The HLA class I gene knock-in non-human animal according to any of [1] to [14], wherein the non-human animal is a mouse.

[16] The HLA class I gene knock-in non-human animal according to [15], which has a genotype represented as B2m$^{+/(HLA/H-2/B2M)}$ or B2m$^{(HLA/H-2/B2M)/(HLA/H-2/B2M)}$.

[17] A method for preparing an HLA class I gene knock-in non-human animal, which comprises a step of introducing an artificial chimeric gene encoding an artificial chimeric protein comprising a protein composed of β2 microglobulin, HLA class I α1 and α2 regions, and an MHC class I α3 region of the non-human animal ligated in such order from the N terminus into a site under the control of a transcription regulatory region of β2 microglobulin loci of the non-human animal.

[18] The method according to [17] comprising the following steps:

(1) preparing a targeting vector comprising the artificial chimeric gene encoding the artificial chimeric protein comprising of a protein composed of β2 microglobulin, HLA class I α1 and α2 regions, and an MHC class I α3 region of the non-human animal ligated in such order from the N terminus; and (2) allowing the targeting vector to react with a pluripotent stem cell of the non-human animal, so as to introduce the targeting vector into a site under the control of the transcription regulatory region of β2 microglobulin gene of the pluripotent stem cell.

[19] The method according to [18], wherein the pluripotent stem cell is an ES cell, GS cell, or iPS cell.

[20] The method according to [18] or [19], wherein the artificial chimeric gene is introduced into the site under the control of the transcription regulatory region of β2 microglobulin gene of the pluripotent stem cell via homologous recombination.

[21] The method according to any of [17] to [20], wherein the β2 microglobulin is human β2 microglobulin.

[22] A cell that expresses an artificial chimeric gene encoding an artificial chimeric protein comprising a protein composed of β2 microglobulin, HLA class I α1 and α2 regions, and an MHC class I α3 region of a non-human animal ligated in such order from the N terminus under the control of a transcription regulatory region of β2 microglobulin gene of the non-human animal.

[23] The cell according to [22], which is an ES cell, GS cell, or iPS cell.

[24] An isolated tissue, isolated organ, isolated cell, primary cell culture, or established cell line that is obtained from the HLA class I gene knock-in non-human animal according to any of [1] to [16].

[25] A method for screening of a test-substance-specific CTL inducer, which comprises the following steps (1) and (2):

(1) allowing a test substance to react with the HLA class I gene knock-in non-human animal according to any of [1] to [16], the cell according to [22] or [23], or the isolated tissue, isolated organ, isolated cell, primary cell culture, or established cell line according to [24]; and (2) determining whether or not test-substance-specific CTL is induced.

[26] A method for determining the presence or absence of an HLA class I-restricted antigen, which comprises the following steps (1) and (2):

(1) allowing a test substance to react with the HLA class I gene knock-in non-human animal according to any of [1] to [16], the cell according to [22] or [23], or the isolated tissue, isolated organ, isolated cell, primary cell culture, or established cell line according to [24]; and (2) determining whether or not test-substance-specific CTL is induced.

[27] A method for screening of a therapeutic or preventive agent of a disease, which comprises the following steps (1) and (2):

(1) allowing a test substance to react with the HLA class I gene knock-in non-human animal according to any of [1] to [16], the cell according to [22] or [23], or the isolated tissue, isolated organ, isolated cell, primary cell culture, or established cell line according to [24]; and (2) determining whether or not test-substance-specific CTL is induced.

[28] The method according to [27], wherein the disease is a cancer or infection.

[29] A method for comparing the HLA-restricted specificity of CTL reactions induced by test substances, which comprises the following steps (1) and (2):

(1) administering test substances to a plurality of different strains of the HLA class I gene knock-in non-human animals according to any of [1] to [16] that express different HLA class I genes and assaying the CTL reactions induced in the non-human animals; and (2) comparing the CTL reactions assayed in the non-human animals and evaluating the HLA-restriction of test substances inducing CTL reactions.

[30] A method for evaluating effectiveness of CTL reactions induced by test substances, which comprises the following steps (1) and (2):

(1) administering test substances to a plurality of different strains of the HLA class I gene knock-in non-human animals according to any of [1] to [16] that express different HLA class I genes and assaying the CTL reactions induced in the non-human animals; and (2) comparing the CTL reactions assayed in the non-human animals and evaluating the HLA-restriction of test substances inducing CTL reactions.

[31] A method for evaluating the safety of a test substance, which comprises the following steps (1) and (2):

(1) allowing a test substance to react with the HLA class I gene knock-in non-human animal according to any of [1] to [16]; and (2) analyzing unfavorable reactions occurring in the non-human animal.

[32] The method according to [31], wherein the unfavorable reactions are autoimmune reactions.

[33] The method according to any of [25] to [32], wherein the test substances are one or more of peptides, one or more of polypeptide, one or more of oligonucleotides, one or more of polynucleotides, or one or more of proteins.

This description includes part or all of the content as disclosed in the description and/or drawings of Japanese Patent Application No. 2013-217684, which is a priority application of the present application.

Effects of the Invention

The present invention enables the following.

The present invention provides a non-human animal having genetic modification at β2 microglobulin loci.

More specifically, the present invention provides an HLA class I gene knock-in non-human animal or non-human cell in which an artificial chimeric gene encoding an artificial chimeric protein comprising a protein composed of β2 microglobulin, HLA class I α1 and α2 regions, and an MHC class I α3 region of a non-human animal ligated in such order from the N terminus (hereafter, referred to as an "artificial chimeric gene" or "the artificial chimeric gene") is expressed under the control of a transcription regulatory region of β2 microglobulin gene of such non-human animal, a derivative thereof, and a method for using the same.

The present invention is characterized in that the artificial chimeric gene is expressed under the control of the transcription regulatory region of β2 microglobulin gene of a non-human animal. Thus, problems of conventional HLA gene-introduced transgenic mice or conventional combined mutant mice (i.e., combined mutant mice prepared by first preparing transgenic mice via introduction of an artificial MHC class I gene encoding a protein comprising β2 microglobulin, HLA class I α1 and α2 domains, and a mouse H-2 class I α3 domain fused to each other into a site downstream of HLA class I gene promoter and then subjecting the resulting transgenic mice to crossing with β2 microglobulin gene knockout mice (Non-Patent Document 9), hereafter referred to as "conventional combined mutant mice") can be resolved.

More particularly, the present invention has excellent advantages, as described below.

(1) Reduced Time for Preparation, Efficiency Promotion, and Simplification.

When preparing conventional combined mutant mice, it has been necessary to prepare transgenic mice by introducing the artificial MHC class I gene into a site downstream of HLA class I gene promoter, select a strain exhibiting the optimal expression level of the introduced genes, and subject the selected strain to crossing with β2 microglobulin gene knockout mice. This required a duration of at least a year and a half to two years to obtain combined mutant mice.

In contrast, steps of strain selection and crossing are not necessary to prepare the non-human animals according to the present invention. When non-human animals are mice, such mice can then be prepared within a short period of time (e.g., approximately 7 to 8 months).

In short, according to the present invention, the target HLA class I gene knock-in non-human animal can be prepared within a shorter period of time in a more efficient and simple manner, compared with conventional combined mutant mice.

(2) Realization of Gene Expression at Physiological Levels (Gene Expression Level).

In the case of conventional combined mutant mice, various factors such as the copy number of the introduced artificial MHC class I genes, the positions of gene introduction into the genome, and epigenetic modification, influence the artificial chimeric gene expression levels and the sites of gene expression. It has thus been difficult to regulate the expression levels and the sites of gene expression. In addition, whether or not the functional artificial MHC class I genes are expressed is influenced by such factors. Accordingly, expression of such functional artificial MHC class I gene often occurred by accident.

As opposed to the above, in the non-human animal according to the present invention, the artificial chimeric gene is allowed to express under the control of a transcription regulatory region of β2 microglobulin gene in either locus or both loci of a pair of the β2 microglobulin loci of the non-human animal. Unlike conventional combined mutant mice, accordingly, the copy number of the introduced artificial chimeric genes and the sites of gene introduction can be regulated in the non-human animal according to the present invention.

In short, in the non-human animal according to the present invention, the copy number of the artificial chimeric genes introduced into the β2 microglobulin loci is 1 or 2. This realizes gene expression at more physiological levels, unlike the case of conventional combined mutant mice.

(3) Realization of Comparison Among Strains.

In the non-human animals according to the present invention, the artificial chimeric gene expression levels are constant among different strains because of the characteristic described above. A comparison among strains can be made when, for example, screening for a test-substance-specific CTL inducer, determining the presence or absence of HLA class I-restricted antigen, screening for a therapeutic or preventive agent of a disease, comparing HLA-restricted specificity of CTL reactions induced by test substances, evaluating effectiveness of the CTL reactions induced by test substances, or evaluating the safety of the test substances.

(4) Facilitation of Heterozygote Preparation.

According to an embodiment of the non-human animal according to the present invention, a non-human animal can comprise a copy of the artificial chimeric gene containing the HLA class I gene into each site under the control of the transcription regulatory region of the β2 microglobulin gene in the β2 microglobulin loci. The HLA class I genes contained in the artificial chimeric genes differ from one another at each sites. This embodiment of the present invention can be readily prepared via crossing of the non-human animals according to the present invention. According to this embodiment of the present invention, a non-human animal that expresses the HLA class I genes of different genotypes at equal levels can be prepared. When preparation of such non-human animal is intended in accordance with a method for preparing conventional combined mutant mice, it is necessary to prepare transgenic animals expressing HLA class I genes of different genotypes, select the strain expressing such genes of different genotypes at equal levels, and subject the selected strain to crossing. However, the strain expressing such genes of different genotypes at equal levels is not readily selected. In the case of the non-human animal according to the present invention, in contrast, it is apparent that the copy number of the artificial chimeric genes is 1 or 2, and the artificial chimeric gene is located under the control of the transcription regulatory region of the β2 microglobulin gene in the β2 microglobulin loci. Thus, a non-human animal comprising a copy of the artificial chimeric genes (i.e., HLA class I genes of different genotypes) in each of the β2 microglobulin loci can be obtained via crossing, and such HLA class I genes of different genotypes are considered to be expressed at physiological levels. It is known that HLA class I genes of different genotypes are often expressed in humans (i.e., the HLA class I genes are more likely to be heterozygotes than homozygotes). According to an embodiment of the non-human animal according to the present invention, HLA class I genes of different genotypes are expressed at physiological levels. When investigating, for example, the HLA-restricted CTL reactions induced by test substances, accordingly, such evaluation model is considered to be more extrapolatable to humans.

(5) Realization of Gene Expression at Physiological Levels (Site of Gene Expression).

In the non-human animal according to the present invention, the artificial chimeric gene expression is under the control of a transcription regulatory region of β2 microglobulin gene in β2 microglobulin loci. Thus, unlike the case of conventional combined mutant mice, the artificial chimeric gene expression is regulated by a transcription regulatory region, such as a β2 microglobulin promoter of the non-human animal. Accordingly, the expression level of the artificial chimeric gene is expected to be equal to that of the β2 microglobulin gene endogenous to the non-human animal, and the site of expression (e.g., a cell or tissue) is expected to be the same as that of the original MHC class I gene. Accordingly, gene expression can be realized at a more physiological level.

(6) Facilitation of Combined Mutant Animal Preparation.

In the non-human animal according to the present invention, the artificial chimeric gene is knocked in into β2 microglobulin loci of such non-human animal, and it thus becomes a transgenic animal of a single strain. Conventional combined mutant mice (i.e., combined mutant mice prepared via crossing of transgenic mice comprising the artificial MHC class I gene introduced into a site downstream of HLA class I gene promoter with β2 microglobulin gene knockout mice) are human HLA-expressing animals prepared via crossing of transgenic animals of two different strains. Accordingly, in the non-human animal according to the present invention, the β2 microglobulin locus and the artificial chimeric gene locus are not segregated into different gametes, and combined mutant animal preparation via crossing with another strain is advantageously easy. Examples of animals of different strains include immunodeficient animals or cancer model animals.

(7) Improvement and Diversification of Epitope Recognition Capacity.

Test substances that did not induce CTL in conventional HLA gene-introduced transgenic mice may be capable of CTL induction in the non-human animal according to the present invention.

(8) Prevention of Reduced HLA Class I Expression and Reduced HLA Class I-Restricted CTL Response Caused by H-2 Class I.

It is known that β2 microglobulin molecules constitute MHC class I, H-2 class I expression is lost in β2 microglobulin homozygous-knockout mice, and the population of $CD4^-CD8^+T$ cells is significantly decreased (Nature 1990, 344: 742-746).

In general, it is necessary for conventional combined mutant mice to have homozygous-knockout of β2 microglobulin genes. Thus, the artificial MHC class I genes are expressed while H-2 class I gene expression is lost, and such combined mutant mice are subjected to various types of experiments for the following reasons. When the β2 microglobulin genes are subjected to heterozygous knockout, the endogenous H-2 class I genes and the introduced artificial MHC class I gene are co-expressed, the artificial MHC class I gene expression level is reduced to a level equal to that of wild-type non-transgenic mice, and the artificial MHC class I gene expression level is not sufficient (J. Immunol., Jun. 17, 2013; 191: 583-593). While the $CD4^-CD8^+T$ cell content in conventional combined mutant mice from which the β2 microglobulin genes have been heterozygously knocked out is equal to that of wild-type non-transgenic mice, HLA class I-restricted CTL induction could not be investigated with the use of such combined mutant mice despite the favorable properties thereof.

In the case of the non-human animal according to the present invention, the expression levels of the artificial chimeric genes introduced (knocked in) into either one locus (i.e., heterozygous) and both loci (i.e., homozygous) of the pair of β2 microglobulin loci of the non-human animal were within the range that could be predicted on the basis of the number of gene copies introduced. The expression level of the heterozygously introduced artificial chimeric genes was not reduced to a level equal to that of wild-type non-transgenic mice (FIG. 9-1, FIG. 9-2). In addition, the $CD4^-CD8^+T$ cell content was maintained at a level equal to that in wild-type non-transgenic mice (FIG. 16). Accordingly, the non-human animal according to the present invention can be used for the investigation of HLA class I-restricted CTL induction reaction when the artificial chimeric gene is knocked in into either one locus (i.e., heterozygous) of the pair of β2 microglobulin loci of the non-human animal.

When the β2 microglobulin gene is of a wild type, it is known that HLA class I-restricted CTL induction is significantly lowered in conventional HLA gene-introduced transgenic mice, compared with a case when the β2 microglobulin gene is homozygously knocked out (Vaccine 2004 22: 1728-1731, International Immunol., 2002, 14: 925-934). When the β2 microglobulin gene is of a wild type, for example, the introduced HLA class I genes are co-expressed with the endogenous H-2 class I genes. During the education and the maintenance of the HLA class I-restricted $CD8^+$ cells, the H-2 class I compete with the HLA class I. It is assumed to be due to the fact that the population of $CD8^+$ cells educated in an HLA class I-restricted manner is decreased.

On the other hand, in the case of the non-human animal according to the present invention, the degree of CTL induction by the HLA class I-restricted epitope when the artificial chimeric genes were knocked in into either one locus (i.e., heterozygous) of the pair of the β2 microglobulin loci of the non-human animal was equal to that when such genes were knocked in into both loci (i.e., homozygous) of such pair (FIGS. 11, 12, 14, and 15). Accordingly, HLA class I-restricted CTL induction reaction can be investigated in the non-human animal according to the present invention, when the artificial chimeric gene is knocked in into either one locus (i.e., heterozygous) of the pair of β2 microglobulin loci of the non-human animal.

BRIEF DESCRIPTION OF THE DRAWINGS

FIG. 7-1 shows the results of analysis of HLA-A24 expression levels in blood cells and spleen cells of knock-in mice via flow cytometry.

FIG. 7-2 shows the results of analysis of HLA-A3 expression levels in blood cells and spleen cells of knock-in mice via flow cytometry.

FIG. 8-1 shows the results of analysis of H-2K$^b$ expression levels in blood cells of knock-in mice via flow cytometry.

FIG. 8-2 shows the results of analysis of H-2K$^b$ expression levels in blood cells of knock-in mice via flow cytometry.

FIG. 9-1 shows the results of analysis of artificial chimeric protein (including HLA-A2 and human β2 microglobulin) expression levels in blood cells of knock-in mice via flow cytometry.

FIG. 9-2 shows the results of analysis of artificial chimeric protein (including human β2 microglobulin) expression levels in blood cells of knock-in mice via flow cytometry.

FIG. 10-1 shows the results of analysis of H-2K$^b$/H-2D$^b$ expression levels in blood cells of knock-in mice via flow cytometry.

FIG. 10-2 shows the results of analysis of H-2K$^b$/H-2D$^b$ expression levels in blood cells of knock-in mice via flow cytometry.

FIG. 16-1 shows the results of analysis of CD4$^-$CD8$^+$T cell content in blood cells of wild-type mice, heterozygous knock-in mice carrying an artificial chimeric gene (including HLA-A3, HLA-A24, HLA-A2, and HLA-A31), homozygous knock-in mice carrying artificial chimeric genes (including HLA-A3, HLA-A24, HLA-A2, and HLA-A31), and double knock-in mice carrying the first artificial chimeric gene (including HLA-A24) and the second artificial chimeric gene (including HLA-A3) via flow cytometry.

FIG. 16-2 (continued from FIG. 16-1)

MODE FOR CARRYING OUT THE INVENTION

Figure 1:
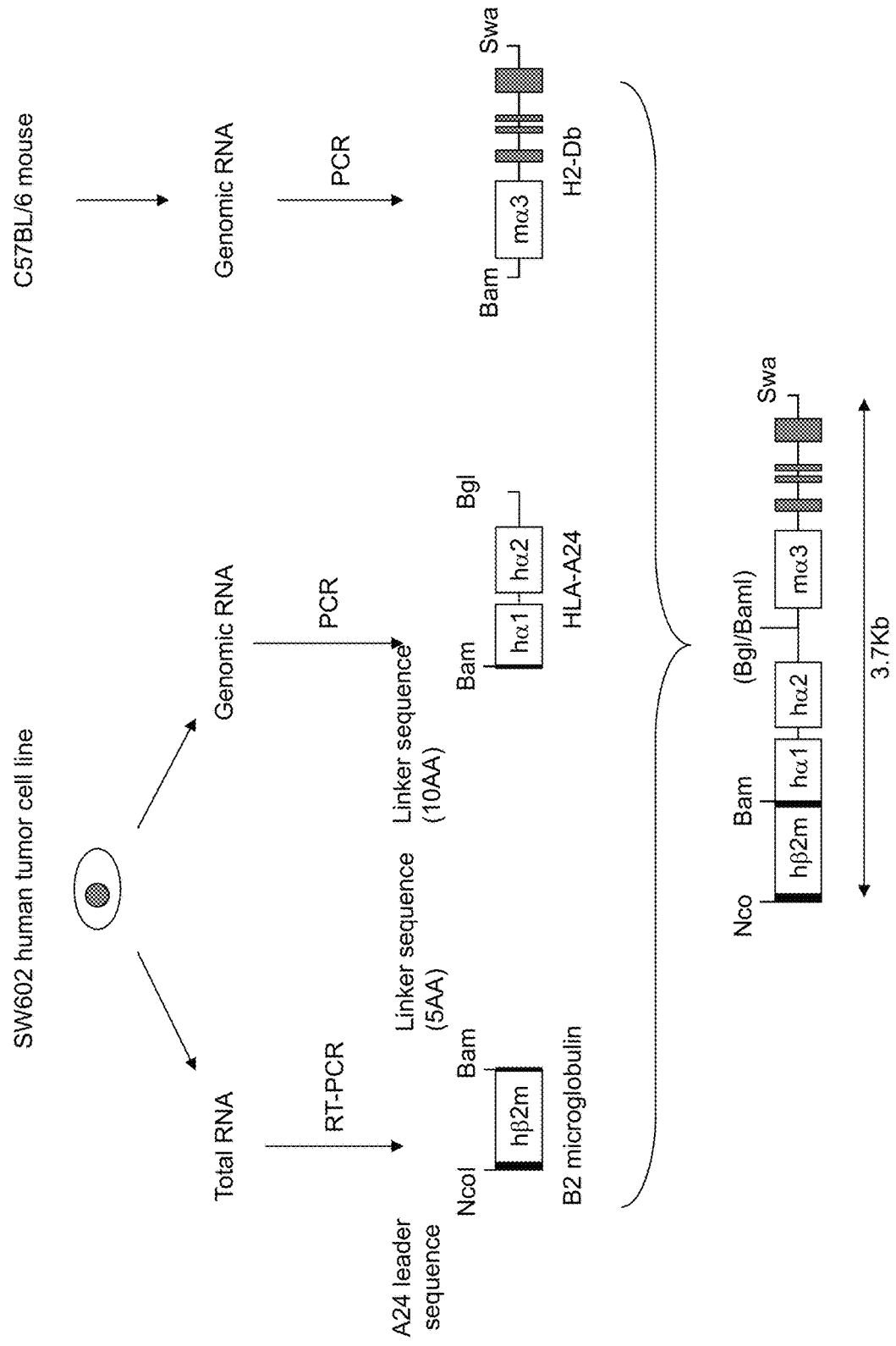
FIG. 1 schematically shows a method for preparing an artificial chimeric gene encoding an artificial chimeric protein comprising human β2 microglobulin, HLA class I α1 and α2 regions, and an MHC class I α3 region of a non-human animal.

Hereafter, the present invention is described in detail.

The term "artificial chimeric protein" used herein refers to a fusion protein comprising β2 microglobulin, HLA class I α1 and α2 regions, and an MHC class I α3 region of a non-human animal ligated in such order from the N terminus.

When adjacent protein domains are "ligated" to each other in the present invention, such adjacent protein domains may be directly bound to each other. Alternatively, adjacent protein domains may be indirectly bound to each other with the aid of an amino acid sequence serving as an adequate spacer therebetween. A conventionally known peptide linker can be used as a spacer, and the number and the type of amino acids constituting such peptide linker are not limited.

The term "artificial chimeric gene" used herein refers to a gene encoding the artificial chimeric protein described above. More particularly, the term refers to an artificial fusion gene comprising a gene encoding β2 microglobulin, a gene encoding HLA class I α1 and α2 regions, and a gene encoding an MHC class I α3 region of a non-human animal ligated in such order from the N terminus. The genes may be directly bound to each other, or adjacent genes may be indirectly bound to each other with the aid of a nucleotide sequence encoding an amino acid sequence serving as the spacer. For example, a nucleotide sequence encoding a conventionally known peptide linker can be used as a nucleotide sequence encoding an amino acid sequence serving as such spacer. The nucleotide sequence encoding an amino acid sequence serving as the spacer can comprise a restriction enzyme recognition sequence, according to need.

The aforementioned artificial chimeric gene preferably encodes an artificial chimeric protein comprising a protein composed of HLA class I α1 and α2 regions, and a region from MHC class I α3 region of a non-human animal to an intracellular domain bound through its N terminus to β2 microglobulin through its C terminus with the aid of a peptide linker. (While the number and the type of amino acids are not limited, the number of amino acids is preferably about 1 to 100, more preferably about 5 to 50, and particularly preferably about 10 to 30.) Such artificial chimeric gene may comprise HLA class I α1 and α2 regions, and a region from MHC class I α3 region of a non-human animal to an intracellular domain without particular limitation.

The term "β2 microglobulin" used herein refers to a protein constituting MHC class I β chain. The term "β2 microglobulin gene" used herein refers to a gene of β2 microglobulin constituting MHC class I β chain.

The term "β2 microglobulin gene" used herein may refer to an exogenous β2 microglobulin gene that is not derived from a non-human host animal or an endogenous β2 microglobulin gene that is derived from a non-human host animal. Accordingly, in the "artificial chimeric gene" of the present invention, the β2 microglobulin gene may be an exogenous β2 microglobulin gene that is not derived from a non-human host animal or an endogenous β2 microglobulin gene that is derived from a non-human animal.

The term "non-human animal" used herein refers to a mammalian animal, such as a mouse, rat, hamster, guinea pig, rabbit, pig, cow, sheep, cat, or dog, or a bird, reptile, amphibian, or fish. The "non-human animal" according to the present invention is not particularly limited, provided that such animal comprises the β2 microglobulin loci and a foreign gene can be introduced thereinto. Rodents are preferable, mice or rats are more preferable, and mice are particularly preferable from the viewpoint of breeding and handling.

In the present invention, the "β2 microglobulin gene" is preferably a human β2 microglobulin gene.

An example of a human β2 microglobulin gene is a gene encoding human β2 microglobulin consisting of the amino acid sequence as shown in SEQ ID NO: 1. For example, a gene consisting of the nucleotide sequence registered at GenBank under Accession Number: NM_004048.2 can be used.

In addition, a polypeptide consisting of an amino acid sequence having deletion, substitution, addition, or insertion of 1 to 10, and preferably 1 to 5 amino acids in the amino acid sequence as shown in SEQ ID NO: 1 and capable of forming a complex with an MHC class I molecule, so as to present the MHC-class-I-specific antigen and a polypeptide consisting of an amino acid sequence having 80% or higher, more preferably 90% or higher, further preferably 95% or higher, and most preferably 99% or higher sequence identity to the amino acid sequence as shown in SEQ ID NO: 1 and capable of forming a complex with an MHC class I molecule, so as to present the MHC-class-I-specific antigen, are within the scope of the human β2 microglobulin according to the present invention. Amino acid sequence comparison can be performed in accordance with a conventional technique. For example, amino acid sequence comparison can be performed with the use of BLAST (i.e., the basic local alignment search tool at the National Center for Biotechnology Information, U.S.A.) using the default settings.

The term "gene" used herein refers to DNA, RNA, or a DNA/RNA hybrid. The form of the gene is not particularly limited, provided that it encodes a protein or polypeptide of interest.

The term "HLA class I" used herein refers to human MHC class I, and examples thereof include HLA-A, HLA-B, and HLA-C. The term "HLA class I gene" used herein refers to a human MHC class I gene, and examples thereof include genes encoding HLA-A, HLA-B, and HLA-C. HLA class I is preferably HLA-A, and more preferably HLA-A24, HLA-A3, HLA-A2, or HLA-A31.

Examples of HLA-A24 include HLA-A2402 consisting of the amino acid sequence as shown in SEQ ID NO: 2 and HLA-A2403 comprising the amino acid sequence as shown in SEQ ID NO: 3. For example, the genes consisting of the nucleotide sequences registered with GenBank under Accession Numbers M64740 and M64741 can be used as genes encoding HLA-A2402 and HLA-A2403, respectively. HLA-A24 is preferably HLA-A2402.

Examples of HLA-A3 include HLA-A0301 consisting of the amino acid sequence as shown in SEQ ID NO: 4 and HLA-A0302 consisting of the amino acid sequence as shown in SEQ ID NO: 5. For example, the genes consisting of the nucleotide sequences registered with GenBank under Accession Numbers L77702.1 and AF217561.1 can be used as genes encoding HLA-A0301 and HLA-A0302, respectively. HLA-A3 is preferably HLA-A0301.

Examples of HLA-A2 include HLA-A0201 consisting of the amino acid sequence as shown in SEQ ID NO: 6 and HLA-A0203 consisting of the amino acid sequence as shown in SEQ ID NO: 7. For example, the genes consisting of the nucleotide sequences registered with GenBank under Accession Numbers AY365426.1 and U03863.1 can be used as genes encoding HLA-A0201 and HLA-A0203, respectively. HLA-A2 is preferably HLA-A0201.

Examples of HLA-A31 include HLA-A3101 consisting of the amino acid sequence as shown in SEQ ID NO: 8 and HLA-A3104 consisting of the amino acid sequence as shown in SEQ ID NO: 9. For example, the genes consisting of the nucleotide sequences registered with GenBank under Accession Numbers M84375.1 and AF148863.1 can be used as genes encoding HLA-A3101 and HLA-A3104, respectively. HLA-A31 is preferably HLA-A3101.

In addition, a polypeptide consisting of an amino acid sequence having deletion, substitution, addition, or insertion of 1 to 10, and preferably 1 to 5 amino acids in the amino acid sequence as shown in any of SEQ ID NOs: 2 to 9 and capable of binding to an antigen peptide at the same or an equivalent level as a polypeptide consisting of the original amino acid sequence and a polypeptide consisting of an amino acid sequence having 80% or higher, more preferably 90% or higher, further preferably 95% or higher, and most preferably 99% or higher sequence identity to the amino acid sequence as shown in any of SEQ ID NOs: 2 to 9 and capable of binding to an antigen peptide at the same or an equivalent level as a polypeptide consisting of the original amino acid sequence are within the scope of the "HLA class I" in the present invention.

The term "HLA class I α1 and α2 regions" used herein refers to α1 and α2 regions that are involved in the formation of an antigen peptide-holding groove among the α1, α2, and α3 regions of the HLA class I molecule. The amino acid sequence of the HLA class I α1 and α2 regions and nucleotide sequences encoding the same can be determined on the basis of the HLA class I sequence information registered in a known database, such as the GenBank database described above.

The term "MHC class I of a non-human animal" used herein refers to MHC class I of an animal other than a human. The term "MHC class I gene of a non-human animal" used herein refers to a gene encoding an MHC class I of an animal other than a human.

Examples of "MHC class I of a non-human animal" include mouse H-2, rat RT1, rabbit RLA, and chicken B-locus.

Mouse H-2 class I includes H-2K, H-2D, and H-2L. Examples of H-2K include H-2K$^b$ consisting of the amino acid sequence as shown in SEQ ID NO: 10, H-2K$^d$ consisting of the amino acid sequence as shown in SEQ ID NO: 11, and H-2K$^k$ consisting of the amino acid sequence as shown in SEQ ID NO: 12. For example, genes consisting of the nucleotide sequences registered with GenBank under Accession Numbers U47328.1, U47329.1, and U47330.1 can be used as genes encoding H-2K$^b$, H-2K$^d$, and H-2K$^k$, respectively. Examples of H-2D include H-2D$^d$ consisting of the amino acid sequence as shown in SEQ ID NO: 13 and H-2D$^b$ consisting of the amino acid sequence as shown in SEQ ID NO: 14. For example, genes comprising the nucleotide sequences registered with GenBank under Accession Numbers U47326.1 and U47325.1 can be used as genes encoding H-2D$^d$ and H-2D$^b$, respectively. An example of H-2L is H-2L$^d$ consisting of the amino acid sequence as shown in SEQ ID NO: 15. For example, a gene consisting of the nucleotide sequence registered with GenBank under Accession Number NM_001267808.1 can be used as a gene encoding H-2L$^d$.

MHC class I of a non-human animal is preferably mouse H-2 class I, with H-2D$^b$ or H-2K$^d$ being particularly preferable.

In addition, a polypeptide comprising an amino acid sequence having deletion, substitution, addition, or insertion of 1 to 10, and preferably 1 to 5, amino acids in the amino acid sequence as shown in any of SEQ ID NOs: 10 to 15 and capable of binding to a CD8 molecule at the same or an equivalent level as the polypeptide consisting of the original amino acid sequence and a polypeptide consisting of an amino acid sequence having 80% or higher, more preferably 90% or higher, further preferably 95% or higher, and most preferably 99% or higher sequence identity to the amino acid sequence as shown in any of SEQ ID NOs: 10 to 15 and capable of binding to a CD8 molecule at the same or an equivalent level as the polypeptide consisting of the original amino acid sequence are within the scope of the "MHC class I of a non-human animal" in the present invention.

The term "an MHC class I α3 region of a non-human animal" used herein refers to an α3 region that is involved in the binding to a co-receptor CD8 molecule expressed on a CTL surface among the α1, α2, and α3 regions of the MHC class I molecule of a non-human animal and an intracellular domain of the MHC class I at the C terminus of such α3 region. When the term "MHC class I α3 region of a non-human animal" appears in this description without any particular limitation, the term refers to a region from the α3 region to the intracellular domain. The amino acid sequence of the MHC class I α3 region of a non-human animal and the nucleotide sequence encoding the same can be determined on the basis of sequence information concerning the MHC class I of a non-human animal registered in a known database, such as the GenBank database described above.

In order for CTL of the non-human animal according to the present invention to effectively recognize an HLA-antigen complex, the "MHC class I α3 region of a non-human animal" is preferably substituted with the same MHC region of a non-human animal into which the artificial chimeric gene is to be introduced (Eur. J. Immunol., 26: 97, 1996; J. Immunol., 159: 4753, 1997).

In the "artificial chimeric protein" of the present invention, genotype combinations of HLA class I α1 and α2 regions, and an MHC class I α3 region of a non-human animal are not particularly limited, provided that the "artificial chimeric protein" can express and function. When the HLA class I α1 and α2 regions are derived from HLA-A2, the MHC class I α3 region of a non-human animal is preferably derived from mouse H-2D$^b$. When the α1 and α2 regions are derived from HLA-A24, the mouse α3 region is preferably derived from H-2D$^b$. When the HLA class I at and α2 regions are derived from HLA-A3, the MHC class I α3 region of a non-human animal is preferably derived from mouse H-2D$^b$. When the HLA class I α1 and α2 regions are derived from HLA-A31, the MHC class I α3 region of a non-human animal is preferably derived from mouse H-2D$^b$.

The "artificial chimeric gene" of the present invention comprises the gene encoding β2 microglobulin, the gene encoding HLA class I α1 and α2 regions, and the gene encoding the MHC class I α3 region of a non-human animal. In addition, such "artificial chimeric gene" can comprise any nucleotide sequence that enables regulation of expression and translation of the artificial chimeric gene. Examples of such nucleotide sequences include a leader sequence of the HLA class I gene (HLA-A24 gene, in particular) (SEQ ID NO: 40; ATGGCGCCCCGAACCCTCGTCCTGC-TACTCTCGGGGGCCCTGACCCAGACCTGGGCG).

Such leader sequence is located upstream of the α1 region of the HLA class I gene, and it is involved in localization of proteins expressed by the HLA class I gene on a cell membrane (J. Immunol., 134: 2727, 1985). The leader sequence can be added to the N terminus of the nucleotide sequence encoding β2 microglobulin.

In the present invention, for example: (i) an artificial chimeric gene encoding an artificial chimeric protein comprising a protein composed of human β2 microglobulin, human HLA-A2402 α1 and α2 regions, and a mouse H-2D$^b$ α3 region ligated in such order from the N terminus (consisting of the nucleotide sequence as shown in SEQ ID NO: 16); (ii) an artificial chimeric gene encoding an artificial chimeric protein comprising a protein composed of human β2 microglobulin, human HLA-A0301 α1 and α2 regions, and a mouse H-2D$^b$ α3 region ligated in such order from the N terminus (consisting of the nucleotide sequence as shown in SEQ ID NO: 17); (iii) an artificial chimeric gene encoding an artificial chimeric protein comprising a protein composed of human β2 microglobulin, human HLA-A0201 α1 and α2 regions, and a mouse H-2D$^b$ α3 region ligated in such order from the N terminus (consisting of the nucleotide sequence as shown in SEQ ID NO: 41); and/or (iv) an artificial chimeric gene encoding an artificial chimeric protein comprising a protein composed of human β2 microglobulin, human HLA-A3101 α1 and α2 regions, and a mouse H-2D$^b$ α3 region ligated in such order from the N terminus (consisting of the nucleotide sequence as shown in SEQ ID NO: 42) can be used as such "artificial chimeric gene."

When "the artificial chimeric gene is expressed under the control of a transcription regulatory region of β2 microglobulin gene of the non-human animal" herein, an artificial chimeric gene is ligated to a region that regulates expression (transcription) of the endogenous β2 microglobulin gene in the non-human animal in an operable manner. Thus, the artificial chimeric gene expression is regulated by the transcription regulatory region of the β2 microglobulin gene of such non-human animal. The transcription regulatory region comprises a promoter region and an enhancer region of the β2 microglobulin gene of the non-human animal.

When the "artificial chimeric gene is ligated in an operable manner," such artificial chimeric gene may be ligated and positioned in any manner, provided that the gene expression is induced under the control of the transcription regulatory region of the β2 microglobulin gene of the non-human animal. When an artificial chimeric gene uses an endogenous β2 microglobulin gene derived from a non-human host animal as the "β2 microglobulin gene," for example, a gene encoding HLA class I α1 and α2 regions, and a gene encoding an MHC class I α3 region of a non-human animal may be ligated in such order to the 3' terminus of the endogenous β2 microglobulin gene (excluding the termination codon). Thus, such artificial chimeric gene may be inserted (knocked in) and positioned.

When an artificial chimeric gene uses an exogenous β2 microglobulin gene that is not derived from a non-human host animal as the "β2 microglobulin gene," in contrast, an artificial chimeric gene encoding an artificial chimeric protein comprising a protein composed of human β2 microglobulin, HLA class I α1 and α2 regions, and an MHC class I α3 region of a non-human animal ligated in such order from the N terminus may be inserted into a position downstream of the first methionine of the endogenous β2 microglobulin gene of the non-human animal. Thus, the artificial chimeric gene may be knocked in and positioned in the β2 microglobulin locus of the non-human animal.

When a gene is "knocked in" or "knocked in into the β2 microglobulin locus" in the present invention, a gene of interest is introduced via homologous recombination, so that the artificial chimeric gene is positioned under the control of the transcription regulatory region of the β2 microglobulin gene of a non-human animal, and the artificial chimeric protein is then expressed. When an artificial chimeric gene uses an endogenous β2 microglobulin gene derived from a non-human host animal as the "β2 microglobulin gene," specifically, a gene encoding HLA class I α1 and α2 regions, and a gene encoding an MHC class I α3 region of a non-human animal are ligated in such order to the 3' terminus of the endogenous β2 microglobulin gene (excluding the termination codon), so as to construct the artificial chimeric gene. When an artificial chimeric gene uses an exogenous β2 microglobulin gene that is not derived from a non-human host animal (preferably the human β2 microglobulin gene) as the "β2 microglobulin gene," an artificial chimeric gene encoding an artificial chimeric protein comprising a protein composed of human β2 microglobulin, HLA class I α1 and α2 regions, and an MHC class I α3 region of a non-human animal ligated in such order from the N terminus is inserted into and positioned downstream of the first methionine of the endogenous β2 microglobulin gene of a non-human animal.

In the present invention, the artificial chimeric gene may be knocked in into either locus or both loci of a pair of β2 microglobulin loci of the non-human animal.

When the artificial chimeric gene is knocked in into one of the β2 microglobulin loci, the non-human animal comprises a copy of the artificial chimeric gene in the β2 microglobulin locus.

When the artificial chimeric genes are knocked in into both loci of the β2 microglobulin loci, the non-human animal occasionally comprises 2 copies of the artificial chimeric genes of the same genotype in the β2 microglobulin loci, or the non-human animal occasionally comprises a copy of the artificial chimeric genes of different genotypes in each β2 microglobulin locus.

The artificial chimeric gene is occasionally knocked in into one of the β2 microglobulin loci of the non-human animal, and an artificial chimeric protein encoded by the artificial chimeric gene comprises HLA class I α1 and α2 regions. In such a case, HLA class I is preferably HLA-A, more preferably HLA-A24, HLA-A3, HLA-A2, or HLA-A31, and further preferably HLA-A2402, HLA-A0301, HLA-A0201, or HLA-A3101.

The artificial chimeric genes are occasionally knocked in into both loci of the β2 microglobulin loci of the non-human animal, and artificial chimeric proteins encoded by the both artificial chimeric genes each comprise HLA class I α1 and α2 regions. In the case of the same HLA class I genotype, HLA class I is preferably HLA-A, more preferably HLA-A24, HLA-A3, HLA-A2, or HLA-A31, and further preferably HLA-A2402, HLA-A0301, HLA-A0201, or HLA-A3101.

The artificial chimeric genes are occasionally knocked in into both loci of the β2 microglobulin loci of the non-human animal, and artificial chimeric proteins encoded by the both artificial chimeric genes each comprise HLA class I α1 and α2 regions. In the case of different HLA class I genotypes, HLA class I genes are preferably different HLA-A, more preferably two types of HLA-A selected from the group consisting of HLA-A24, HLA-A3, HLA-A2, and HLA-A31, further preferably two types of HLA-A selected from the group consisting of HLA-A2402, HLA-A0301, HLA-A0201, and HLA-A3101, and still further preferably HLA-A2402 or HLA-A0301.

The HLA class I gene knock-in non-human animal according to the present invention may comprise other genetic mutations, in addition to the artificial chimeric genes. Examples of other genetic mutations include mutations of immunologically relevant genes, such as Il2rg, Prkdc, Foxn1, and Rag1, cancer genes, such as Ras, Src, and Myc, and cancer suppressor genes, such as p53 and Apc.

When a non-human animal is a mouse, in the present invention, an HLA class I-expressing non-human animal is an HLA class I-expressing mouse. A genotype of such mouse is preferably $B2m^{+/(HLA-H-2/B2M)}$ or $B2m^{(HLA-H-2/B2M)(HLA/H-2/B2M)}$, more preferably $B2m^{(HLA-A24/H-2/B2M)(HLA-A24/H-2/B2M)}$, $B2m^{+/(HLA-A24/H-2/B2M)}$, $B2m^{(HLA-A3/H-2/B2M)/(HLA-A3/H-2/B2M)}$, $B2m^{+/(HLA-A3/H-2/B2M)}$, $B2m^{(HLA-A2/H-2/B2M)/(HLA-A2/H-2/B2M)}$, $B2m^{+/(HLA-A2/H-2/B2M)}$, $B2m^{(HLA-A31/H-2/B2M)/(HLA-A31/H-2/B2M)}$, $B2m^{+/(HLA-A31/H-2/B2M)}$, $B2m^{(HLA-A24/H-2/B2M)/(HLA-A3/H-2/B2M)}$, $B2m^{(HLA-A24/H-2/B2M)/(HLA-A2/H-2/B2M)}$, $B2m^{(HLA-A24/H-2/B2M)/(HLA-A31/H-2/B2M)}$, $B2m^{(HLA-A3/H-2/B2M)/(HLA-A2/H-2/B2M)}$, $B2m^{(HLA-A3/H-2/B2M)/(HLA-A31/H-2/B2M)}$, or $B2m^{(HLA-A2/H-2/B2M)/(HLA-A31/H-2/B2M)}$ and further preferably $B2m^{(HLA-A2402/H-2/B2M)/(HLA-A2402/H-2/B2M)}$, $B2m^{+/(HLA-A2402/H-2/B2M)}$, $B2m^{(HLA-A0301/H-2/B2M)/(HLA-A0301/H-2/B2M)}$, $B2m^{(HLA-A0301/H-2/B2M)}$, $B2m^{(HLA-A0201/H-2/B2M)/(HLA-A0201/H-2/B2M)}$, $B2m^{(HLA-A0201/H-2/B2M)}$, $B2m^{(HLA-A3101/H-2/B2M)/(HLA-A3101/H-2/B2M)}$, $B2m^{+/(HLA-A3101/H-2/B2M)}$, $B2m^{(HLA-A2402/H-2/B2M)/(HLA-A0301/H-2/B2M)}$, $B2m^{(HLA-A2402/H-2/B2M)/(HLA-A0201/H-2/B2M)}$, $B2m^{(HLA-A2402/H-2/B2M)/(HLA-A3101/H-2/B2M)}$, $B2m^{(HLA-A0301/H-2/B2M)/(HLA-A0201/H-2/B2M)}$, $B2m^{(HLA-A0301/H-2/B2M)/(HLA-A3101/H-2/B2M)}$, or $B2m^{(HLA-0201/H-2/B2M)/(HLA-A3101/H-2/B2M)}$.

Such genotype is still further preferably $B2m^{+/(HLA/H-2D/B2M)}$ or $B2m^{(HLA/H-2D/B2M)/(HLA/H-2D/B2M)}$, furthermore preferably $B2m^{(HLA-A24/H-2D/B2M)/(HLA-A24/H-2D/B2M)}$, $B2m^{+/(HLA-A24/H-2D/B2M)}$, $B2m^{(HLA-A3/H-2D/B2M)/(HLA-A3/H-2D/B2M)}$, $B2m^{+/(HLA-A3/H-2D/B2M)}$, $B2m^{(HLA-A2/H-2D/B2M)/(HLA-A2/H-2D/B2M)}$, $B2m^{+/(HLA-A2/H-2D/B2M)}$, $B2m^{(HLA-A31/H-2D/B2M)/(HLA-A31/H-2D/B2M)}$, $B2m^{+/(HLA-A31/H-2D/B2M)}$, $B2m^{(HLA-A24/H-2D/B2M)/(HLA-A3/H-2D/B2M)}$, $B2m^{(HLA-A24/H-2D/B2M)/(HLA-A2/H-2D/B2M)}$, $B2m^{(HLA-A24/H-2D/B2M)/(HLA-A31/H-2D/B2M)}$, $B2m^{(HLA-A3/H-2D/B2M)/(HLA-A2/H-2D/B2M)}$, $B2m^{(HLA-A3/H-2D/B2M)/(HLA-A31/H-2D/B2M)}$, or $B2m^{(HLA-A2/H-2D/B2M)/(HLA-A31/H-2D/B2M)}$, and still furthermore preferably $B2m^{(HLA-A2402/H-2d/B2M)/(HLA-A2402/H-2D/B2M)}$, $B2m^{+/(HLA-A2402/H-2D/B2M)}$, $B2m^{(HLA-A0301/H-2D/B2M)/(HLA-A0301/H-2D/B2M)}$, $B2m^{(HLA-A0301/H-2D/B2M)}$, $B2m^{(HLA-A0201/H-2D/B2M)/(HLA-A0201/H-2D/B2M)}$, $B2m^{+/(HLA-A0201/H-2D/B2M)}$, B2m$^{(HLA\text{-}A3101/H\text{-}2D/B2M)/(HLA\text{-}A3101/H\text{-}2D/B2M)}$,
B2m$^{(HLA\text{-}A3101/H\text{-}2D/B2M)}$,
B2m$^{(HLA\text{-}A2402/H\text{-}2D/B2M)/(HLA\text{-}A0301/H\text{-}2D\ B2M)}$,
B2m$^{(HLA\text{-}A2402/H\text{-}2D/B2M)/(HLA\text{-}A0201/H\text{-}2D/B2M)}$,
B2m$^{(HLA\text{-}A2402/H\text{-}2D/B2M)/(HLA\text{-}A3101/H\text{-}2D/B2M)}$,
B2m$^{(HLA\text{-}A0301/H\text{-}2D/B2M)/(HLA\text{-}A0201/H\text{-}2D/B2M)}$,
B2m$^{(HLA\text{-}A0301/H\text{-}2D/B2M)/(HLA\text{-}A3101/H\text{-}2D/B2M)}$,
B2m$^{(HLA\text{-}A0201/H\text{-}2D/B2M)/(HLA\text{-}A3101/H\text{-}2D/B2M)}$ or
B2m$^{(HLA\text{-}A0201/H\text{-}2D/B2M)/(HLA\text{-}A3101/H\text{-}2D/B2M)}$.

It is particularly preferable that such genotype be B2m$^{+/(HLA/H\text{-}2Db/B2M)}$, or B2m$^{(HLA/H\text{-}2Db/B2M)/(HLA/H\text{-}2Db/B2M)}$, and more preferably B2m$^{(HLA\text{-}A24/H\text{-}2Db/B2M)/(HLA\text{-}A24/H\text{-}2Db/B2M)}$,
B2m$^{+/(HLA\text{-}A24/H\text{-}2Db/B2M)}$,
B2m$^{(HLA\text{-}A3/H\text{-}2Db/B2M)/(HLA\text{-}A3/H\text{-}2Db/B2M)}$,
B2m$^{+/(HLA\text{-}A3/H\text{-}2Db/B2M)}$,
B2m$^{(HLA\text{-}A2/H\text{-}2Db/B2M)/(HLA\text{-}A2/H\text{-}2Db/B2M)}$,
B2m$^{+/(HLA\text{-}A\text{-}2/H\text{-}2Db/B2M)}$,
B2m$^{(HLA\text{-}A31/H\text{-}2Db/B2M)/(HLA\text{-}A31/H\text{-}2Db/B2M)}$,
B2m$^{+/(HLA\text{-}A31/H\text{-}2Db/B2M)}$,
B2m$^{(HLA\text{-}A24/H\text{-}2Db/B2M)/(HLA\text{-}A3/H\text{-}2Db/B2M)}$,
B2m$^{(HLA\text{-}A24/H\text{-}2Db/B2M)/(HLA\text{-}A2/H\text{-}2Db/B2M)}$,
B2m$^{(HLA\text{-}A24/H\text{-}2Db/B2M)/(HLA\text{-}A31/H\text{-}2Db/B2M)}$,
B2m$^{(HLA\text{-}A3/H\text{-}2Db/B2M)/(HLA\text{-}A2/H\text{-}2Db/B2M)}$,
B2m$^{(HLA\text{-}A3/H\text{-}2Db/B2M)/(HLA\text{-}A31/H\text{-}2Db/B2M)}$, or
B2m$^{(HLA\text{-}A2/H\text{-}2Db/B2M)/(HLA\text{-}A31/H\text{-}2Db/B2M)}$. It is particularly preferable that such genotype be B2m$^{(HLA\text{-}A2402/H\text{-}2Db/B2M)/(HLA\text{-}A2402/H\text{-}2Db/B2M)}$,
B2m$^{+/(HLA\text{-}A2402/H\text{-}2Db/B2M)}$,
B2m$^{(HLA\text{-}A0301/H\text{-}2Db/B2M)/(HLA\text{-}A0301/H\text{-}2Db/B2M)}$,
B2m$^{+/(HLA\text{-}A0301/H\text{-}2Db/B2M)}$,
B2m$^{(HLA\text{-}A0201/H\text{-}2Db/B2M)/(HLA\text{-}A0201/H\text{-}2Db/B2M)}$,
B2m$^{+/(HLA\text{-}A0201/H\text{-}2Db/B2M)}$,
B2m$^{(HLA\text{-}A3101/H\text{-}2Db/B2M)/(HLA\text{-}A3101/H\text{-}2Db/B2M)}$,
B2m$^{+/(HLA\text{-}A3101/H\text{-}2Db/B2M)}$,
B2m$^{(HLA\text{-}A2402/H\text{-}2Db/B2M)/(HLA\text{-}A0301/H\text{-}2Db/B2M)}$,
B2m$^{(HLA\text{-}A2402/H\text{-}2Db/B2M)/(HLA\text{-}A0201/H\text{-}2Db/B2M)}$,
B2m$^{(HLA\text{-}A2402/H\text{-}2Db/B2M)/(HLA\text{-}A3101/H\text{-}2Db/B2M)}$,
B2m$^{(HLA\text{-}A0301/H\text{-}2Db/B2M)/(HLA\text{-}A0201/H\text{-}2Db/B2M)}$,
B2m$^{(HLA\text{-}A0301/H\text{-}2Db/B2M)/(HLA\text{-}A3101/H\text{-}2Db/B2M)}$, or
B2m$^{(HLA\text{-}A0201/H\text{-}2Db/B2M)/(HLA\text{-}A3101/H\text{-}2Db/B2M)}$.

The HLA class I gene knock-in non-human animal of the present invention can be prepared by, for example, the method described below, although the method of preparation is not limited thereto. A person skilled in the art can adequately modify a technique of genetic engineering, such as gene recombination, that is generally employed in the art.

The HLA class I gene knock-in non-human animal of the present invention occasionally uses an exogenous β2 microglobulin gene that is not derived from a non-human host animal as the "β2 microglobulin gene" (hereafter, this method is referred to as "Method I"). In such a case, an artificial chimeric gene encoding an artificial chimeric protein comprising a protein composed of β2 microglobulin, HLA class I α1 and α2 regions, and an MHC class I α3 region of a non-human animal ligated in such order from the N terminus can be knocked in into β2 microglobulin loci of such non-human animal.

More specifically, the HLA class I gene knock-in non-human animal of the present invention can be prepared by a method comprising the following steps:

(1) preparing a targeting vector comprising an artificial chimeric gene encoding an artificial chimeric protein comprising a protein composed of β2 microglobulin, HLA class I α1 and α2 regions, and an MHC class I α3 region of a non-human animal ligated in such order from the N terminus; and (2) allowing the targeting vector to act on a pluripotent stem cell of the non-human animal, so as to introduce the artificial chimeric gene into β2 microglobulin locus in the pluripotent stem cell.

The term "pluripotent stem cell" used herein refers to a cell that is capable of differentiating into a plurality of cell lines (i.e., pluripotency) and is also capable of maintaining pluripotency through successive cell divisions (i.e., auto-reproducibility). Examples thereof include embryonic stem (ES) cells, germline stem (GS) cells, and induced pluripotent stem (iPS) cells.

The HLA class I gene knock-in non-human animal of the present invention occasionally uses an endogenous β2 microglobulin gene that is derived from a non-human host animal as the "β2 microglobulin gene" (hereafter, this method is referred to as "Method II"). In such a case, a transgene encoding a protein comprising HLA class I α1 and α2 regions, and an MHC class I α3 region of a non-human animal ligated in such order from the N terminus may be knocked in into the 3' terminus of the endogenous β2 microglobulin gene (excluding the termination codon) of the non-human animal.

More specifically, the HLA class I gene knock-in non-human animal of the present invention can be prepared by a method comprising the following steps:

(1') preparing a targeting vector comprising a transgene encoding a protein comprising HLA class I α1 and α2 regions, and an MHC class I α3 region of a non-human animal ligated in such order from the N terminus; and (2') allowing the targeting vector to act on a pluripotent stem cell of the non-human animal, and introducing the transgene into the 3' terminus of the β2 microglobulin gene of the pluripotent stem cell (excluding the termination codon), so as to construct the artificial chimeric gene with the endogenous β2 microglobulin gene.

The artificial chimeric gene or the transgene can be introduced into a pluripotent stem cell in accordance with, for example, a method known in the art. For example, a method of gene introduction via homologous recombination can be employed. Specifically, the method described in Gene Targeting (Sedivy, J. M. and Joyner, A. L., 1992) or a method involving the use of artificial nucleases, such as zinc finger nucleases (ZFNs), transcription activator-like effector nucleases (TALEN), or CRISPR/Cas systems can be employed.

When the method described in Gene Targeting (Sedivy J. M. and Joyner, A. L., 1992) is employed, for example, the non-human animal according to the present invention can be prepared in the manner described below. Methods for preparing the non-human animal according to the present invention are not limited thereto.

In accordance with Method I, the artificial chimeric gene is prepared via cloning of gene fragments each encoding human β2 microglobulin, HLA class I α1 and α2 regions, and an MHC class I α3 region of a non-human animal. A gene fragment can be a DNA fragment. A method of cloning is not particularly limited, as long as a target gene fragment can be obtained. For example, PCR can be employed. As a template, any cell or DNA library that carries a target gene may be used. For example, total RNA or genomic DNA prepared from a human cell can be used. As a human cell line, for example, a human tumor cell line (e.g., SW620 or HepG2) can be used. As described in the examples, the full-length gene sequence can be artificially synthesized.

With the use of three types of DNA fragments obtained above, an artificial chimeric gene encoding an artificial chimeric protein comprising a protein composed of β2 microglobulin, HLA class I α1 and α2 regions, and an MHC class I α3 region of a non-human animal ligated in such order from the N terminus is prepared.

A method of preparing such artificial chimeric gene is not particularly limited, provided that an artificial chimeric gene encoding an artificial chimeric protein comprising a protein composed of β2 microglobulin, HLA class I α1 and α2 regions, and an MHC class I α3 region of a non-human animal ligated in such order from the N terminus is constructed at the end. According to need, a restriction enzyme recognition sequence can be provided at the 5' terminus or 3' terminus of a gene fragment encoding β2 microglobulin, a gene fragment encoding HLA class I α1 and α2 regions, and a gene fragment encoding an MHC class I α3 region of a non-human animal.

For example, a gene fragment comprising a sequence encoding human β2 microglobulin comprising a restriction enzyme (e.g., NcoI) recognition sequence at the 5' terminus and a restriction enzyme (e.g., BamHI) recognition sequence at the 3' terminus is ligated to a gene fragment comprising a sequence encoding an MHC class I α3 region of a non-human animal comprising a restriction enzyme (e.g., BamHI) recognition sequence at the 5' terminus and a restriction enzyme (e.g., SwaI) recognition sequence at the 3' terminus with the aid of the restriction enzyme (e.g., BamHI) recognition sequence. The resultant is then cloned into an adequate vector, such as pBluescript, that has been modified to carry a restriction enzyme (e.g., NcoI) recognition sequence and a restriction enzyme (e.g., SwaI) recognition sequence. The resulting vector is digested with a restriction enzyme (e.g., BamHI), and a gene fragment comprising sequences encoding HLA class I α1 and α2 regions to which a restriction enzyme (e.g., BamHI) recognition sequence and a restriction enzyme (e.g., BglII) recognition sequence are added to the 5' terminus and the 3' terminus, respectively, is inserted. In such a case, a target product can be obtained by selecting a clone comprising a restriction enzyme (e.g., BamHI) recognition sequence of a gene fragment comprising a sequence encoding human β2 microglobulin ligated to a restriction enzyme (e.g., BamHI) recognition sequence of a gene fragment comprising a sequence encoding HLA class I α1 and α2 regions and a restriction enzyme (e.g., BamHI) recognition sequence of a gene fragment comprising a sequence encoding an MHC class I α3 region of a non-human animal ligated to a restriction enzyme (e.g., BglII) recognition sequence of a gene fragment comprising a sequence encoding HLA class I α1 and α2 regions.

Subsequently, a genome fragment comprising upstream and downstream regions of the first methionine of the β2 microglobulin gene of a non-human animal is cloned. Such genome fragment can be derived from a non-human animal into which an artificial chimeric gene is to be introduced. The non-human animal can be a mouse. The method of cloning is not particularly limited, as long as a target genome fragment can be obtained. For example, PCR can be employed. As a template, any cell or DNA library that carries a target sequence may be used. For example, a BAC clone comprising a target sequence, genomic DNA prepared from a cell, or a genomic DNA library can be used. A BAC clone, genomic DNA prepared from a cell, or a genomic DNA library may be derived from a mouse.

The genome fragment is not particularly limited, provided that it is long enough to cause homologous recombination in a pluripotent stem cell, such as an ES cell. It is preferable that a sequence be designed to have a disruption of a functional mouse β2 microglobulin gene as a result of homologous recombination and that artificial chimeric gene expression be controlled by a mouse β2 microglobulin gene promoter/enhancer.

The mouse DNA fragment obtained above, the artificial chimeric gene, a positive selection marker, and a negative selection marker are ligated to each other, so as to construct a targeting vector (hereafter, it is referred to as "Targeting Vector I"). Examples of positive selection markers that can be used include a neomycin resistant gene, a hygromycin resistant gene, and a puromycin resistant gene. Examples of negative selection markers that can be used include a diphteria toxin A fragment and a thymidine kinase gene of the simple herpes virus.

A nucleotide sequence encoding a peptide linker and/or a restriction enzyme recognition sequence that are suitable for ligation can be adequately prepared, so as to ligate fragments.

In accordance with Method II, gene fragments each encoding HLA class I α1 and α2 regions, and an MHC class I α3 region of a non-human animal are cloned in the same manner as in Method I in order to prepare a transgene.

A transgene encoding a protein comprising HLA class I α1 and α2 regions, and an MHC class I α3 region of a non-human animal ligated in such order from the N terminus is prepared using the resulting DNA fragment. A transgene can be prepared in accordance with the method for preparing an artificial chimeric gene of Method I.

Subsequently, a genome fragment comprising the 3' terminus of the β2 microglobulin gene of a non-human animal (excluding a termination codon) and a region downstream thereof is cloned in accordance with Method I.

The genome fragment is not particularly limited, provided that it is long enough to cause homologous recombination in a pluripotent stem cell, such as an ES cell. It is preferable that a sequence be designed to constitute an artificial chimeric gene comprising a gene encoding HLA class I α1 and α2 regions, and a gene encoding an MHC class I α3 region of a non-human animal ligated in such order from the 3' terminus of a mouse endogenous β2 microglobulin gene (excluding a termination codon) as a result of homologous recombination. In addition, it is preferable that artificial chimeric gene expression be controlled by a mouse β2 microglobulin gene promoter/enhancer.

The mouse DNA fragment obtained above, the transgene, the positive selection marker, and the negative selection marker are ligated to each other, so as to construct a targeting vector (hereafter, it is referred to as "Targeting Vector II").

Subsequently, Targeting Vector I comprising the artificial chimeric gene or Targeting Vector II comprising the transgene is introduced into a non-human animal cell. A non-human animal cell can be a pluripotent stem cell of a non-human animal. A pluripotent stem cell of a non-human animal can be, for example, a mouse ES cell. Examples of mouse ES cells include ES cells derived from the mouse line 129 and those derived from the mouse line C57BL/6, with ES cells derived from the mouse line 129 being preferable.

Targeting Vector I or II can be introduced into a non-human animal in accordance with various techniques, provided that a gene can be introduced into a cell. For example, electroporation, calcium phosphate co-precipitation, or lipofection can be employed. Such a technique can be employed in combination with a method involving the use of artificial nucleases such as zinc finger nucleases (ZFNs) or transcription activator-like effector nucleases (TALEN) that are designed to be knocked in into a target gene locus. Thus, a gene of interest can be knocked in with high efficiency.

Pluripotent stem cells, such as ES cells, into which the targeting vector has been introduced are sowed on feeder cells exhibiting resistance to specific antibiotics, and culture is conducted in the presence of such specific antibiotics. Resistant colonies surviving 6 to 8 days after the initiation of selection culture are selected, some of the selected colonies are subjected to subculture, and remaining cells are analyzed via PCR to determine whether or not homologous recombination took place. The PCR-positive clones are subjected to Southern hybridization to detect random integration, and clones in which random integration is not detected are subjected to the following process.

Blastocyst-stage embryos are extracted from a pregnant mouse exhibiting a hair color different from that of the ES cells used, and about 10 homologously recombined ES cells described above are injected into the segmentation cavity via micromanipulation. Alternatively, ES cells may be implanted into the 8-cell-stage embryos by the aggregation method. The embryos are implanted into the uterus of the pseudopregnant female mouse, and the mouse is induced to become pregnant and give birth. Thus, a chimeric mouse can be prepared.

When the resulting chimeric male mouse is subjected to crossing with a female mouse exhibiting a hair color different from that of the ES cells used and the resulting offspring exhibits a hair color derived from the ES cells, transfer of the ES cells into the germ lines can be confirmed in addition, an offspring genotype may be analyzed via PCR, and heterozygous knock-in mice carrying an artificial chimeric gene in the β2 microglobulin loci (i.e., mice comprising an artificial chimeric gene knocked in into one of the pair of the mouse β2 microglobulin genes under the control of the transcription regulatory region) can be identified.

The resulting heterozygous mice are subjected to crossing with each other, so that homozygous knock-in mice carrying artificial chimeric genes (i.e., mice comprising artificial chimeric genes knocked in into both loci of the pair of the mouse β2 microglobulin genes under the control of the transcription regulatory region) can be identified.

Two different knock-in mouse lines carrying artificial chimeric genes that contain different HLA class I genes are subjected to crossing with each other such that heterozygous humanized mice can be prepared. The heterozygous humanized mice would comprise a copy of the artificial chimeric gene containing the HLA class I gene inserted into each site of the pair of the β2 microglobulin loci. The HLA class I genes contained in the artificial chimeric genes differ from one another at each sites.

Whether or not artificial chimeric genes are expressed on the cell surface in the prepared knock-in mice can be investigated by, for example, recovering blood cells or spleen cells from knock-in mice and analyzing the recovered blood cells or spleen cells via flow cytometry. Since heterozygous mice retain the wild-type β2 microglobulin loci, mouse H-2 class I genes are also expressed. In contrast, homozygous mice can be identified as MHC class I humanized mouse in which mouse H-2 class I gene expression is lost and expression of the introduced artificial chimeric genes is selectively observed.

Whether or not the non-human animals of the present invention can be used as human models can be examined by any technique known in the art. For example, antigens restricted by HLA class I contained in the introduced artificial chimeric genes are allowed to act on the HLA class I gene knock-in non-human animals of the present invention, and the induction of antigen-specific CTL is inspected. An example of a representative method for inspection when non-human animals are mice is described below.

For example, the known HLA class I-restricted antigen peptides that have been introduced are mixed with the Freund's incomplete adjuvant in accordance with a conventional technique, so as to prepare an emulsion. The emulsion is administered subcutaneously to the HLA class I gene knock-in mice of the present invention at a site in the vicinity of the tail head. Alternatively, the emulsion may be administered subcutaneously into the back or intraperitoneally. Lymph nodes are extracted from the groin of the mouse 1 week after the final administration, and lymph node cells are prepared in accordance with a conventional technique. Cells prepared from other tissues such as spleen cells can also be used.

The prepared cells are cultured for about a week in the presence of antigen peptides and cytokines (e.g., interleukins 2, 15, or 21), and the release of cytokines such as interleukin 2 or interferon γ from T cells is analyzed via ELISPOT assays based on the Sandwich ELISA principles or other techniques. Thus, CTL induction can be investigated. In this case, spleen cells obtained from un-immunized knock-in mice may be irradiated with X-rays and can be used as antigen-presenting cells, and cultured in the presence of lymph node cells. For example, a significant increase in the amounts of various cytokines produced by CTL induced upon antigen stimulation, in comparison with the case of negative control administration, is confirmed. Thus, whether or not the non-human animals of the present invention can be used as human models can be confirmed.

In such case, target cells that express the same HLA class I genes as the non-human animal according to the present invention are further added, and cytotoxic activity on the target cells is evaluated. Thus, whether or not the non-human animals of the present invention can be used as human models can be determined. Examples of target cells that can be used include cells isolated from the non-human animal according to the present invention, cells into which the artificial chimeric genes have been introduced, and cells that naturally express the HLA class I gene. In such a case, $^{51}$Cr-release assays (Int. J. Cancer, 58: 317, 1994) or other techniques can be employed. Specifically, the target cells are labeled with $^{51}$Cr, the labeled target cells are pulsed with the target antigens, samples derived from the non-human animal according to the present invention (e.g., spleen cells) are added thereto, and the amount of $^{51}$Cr released when the target cells are damaged by CTL is assayed. If antigen-specific CTL induction is observed as a result of such assays, it can be determined that the non-human animal according to the present invention can be used as a human model.

The present invention also provides an isolated tissue, isolated organ, isolated cell, primary cultured cell, or established cell line obtained from the HLA class I gene knock-in non-human animal according to the present invention. Tissues or organs are preferably the thymic gland, the spleen, the bone marrow, hematopoietic tissue, or lymph tissue. Preferable cells are antigen presenting cells, T cells, B cells, or hematopoietic stem cells.

The present invention also provides a cell that expresses an artificial chimeric gene encoding an artificial chimeric protein comprising a protein composed of β2 microglobulin, HLA class I α1 and α2 regions, and an MHC class I α3 region of a non-human animal ligated in such order from the N terminus under the control of a transcription regulatory region of β2 microglobulin gene of the non-human animal. In artificial chimeric genes expressed in such cell, the β2 microglobulin gene may be an exogenous β2 microglobulin gene that is not derived from a non-human host animal cell or an endogenous β2 microglobulin gene that is derived from a non-human animal cell. Such cell can be prepared by introducing Targeting Vector I or II into a non-human animal cell in accordance with the technique described above. A non-human animal cell is preferably a pluripotent stem cell derived from a non-human animal, and more preferably an ES cell or iPS cell derived from a non-human animal. Such cell may be isolated or induced from an HLA class I gene knock-in non-human animal.

Hereafter, methods of the use of the HLA class I gene knock-in non-human animal of the present invention, derivatives thereof (e.g., cells and organs), cells that express the artificial chimeric gene of the present invention, and derivatives thereof (e.g., organs prepared from iPS cells when cells that express artificial chimeric genes are iPS cells) are described, although methods are not limited thereto.

The HLA class I gene knock-in non-human animal of the present invention, derivatives thereof (e.g., cells and organs), cells that express the artificial chimeric gene of the present invention, and derivatives thereof (e.g., organs prepared from iPS cells when cells that express artificial chimeric genes are iPS cells) can be used for screening for a test-substance-specific CTL inducer, determination of the presence or absence of the HLA class I-restricted antigen, screening for a therapeutic or preventive agent for a disease (e.g., cancer), comparison of HLA-restricted specificity of CTL reactions induced by a test substance, evaluation of effectiveness of CTL reactions induced by a test substance, evaluation of the safety of a test substance (e.g., the risk that test substance poses for induction of an autoimmune reaction), or other purposes.

More specifically, for example, a test substance is administered to the HLA class I gene knock-in non-human animal of the present invention, and the capacity of the test substance for CTL induction is assayed and evaluated. Thus, a CTL inducer can be screened for, the presence or absence of the HLA class I-restricted antigen can be determined, and/or a therapeutic or preventive agent for a disease can be screened for. Examples of "test substances" include known tumor antigen proteins, partial peptides thereof, viruses, virus-derived antigen proteins, partial peptides thereof, bacteria-derived antigen proteins, antigen peptides thereof, proteins and peptides with unknown activity, and polynucleotides or oligonucleotides encoding such substances. The capacity for CTL induction can be assayed and evaluated in accordance with the above-mentioned method of evaluation used for the HLA class I gene knock-in non-human animal (e.g., $^{51}$Cr-release assays (Int. J. Cancer, 58: 317, 1994)). When the test substance is found to be capable of CTL induction, it becomes apparent that such test substance contains an HLA class I-restricted antigen and that the test substance is capable of serving as a CTL inducer. The CTL inducer thus obtained can be used as a therapeutic and/or preventive agent for a tumor or a virus or bacteria infection. Through administration of a test substance to the HLA class I gene knock-in non-human animal of the present invention and assays and evaluation of the capacity of the test substance for CTL induction, the effects of CTL reactions induced by a test substance and safety thereof (e.g., the risk that test substance poses for induction of an autoimmune disease) can be evaluated.

In addition, the copy number of artificial chimeric genes and the sites of gene introduction are regulated in the HLA class I gene knock-in non-human animal of the present invention. Thus, the expression levels of such artificial chimeric genes can be maintained at equivalent levels between different mouse lines expressing different HLA class I genes. The test substances are administered to a plurality of different HLA class I gene knock-in non-human animals in the same manner, and the capacity of the non-human animals for CTL induction in response to the test substances is assayed, compared, and then evaluated. Thus, the specificity and the effectiveness of CTL reactions induced by test substances can be evaluated.

According to the present invention, CTL cells prepared from the HLA class I gene knock-in non-human animals of the present invention that have been immunized with peptide vaccines may be implanted into the immunodeficient non-human animals resulting from xenografting of human-cancer-derived cell lines. Thus, anti-tumor effects of such peptide vaccines can be evaluated.

EXAMPLES

Hereafter, the present invention is described in greater detail with reference to the examples; however, these examples are provided for illustrative purposes only, and the present invention is not limited to these examples.

Example 1: Cloning of Partial Sequence of HLA-A2402 Gene

In order to prepare artificial chimeric genes, at the outset, a gene fragment containing α1 and α2 regions was cloned via PCR using genomic DNA of the SW620 human tumor cell line as a template on the basis of the sequence information for HLA-A2402 (GenBank Accession No. L47206.1). In such a case, a sequence encoding a peptide of 10 amino acids including a BamHI recognition sequence was added to the N terminus, and the BglII recognition sequence was added to the intron 3 sequence at the C terminus, so as to bind the gene fragment to human β2 microglobulin gene and mouse H-2 α3 region. Specifically, PCR was carried out using the primers shown below, and a 867-bp DNA fragment modified as described above was obtained.

```
Bam-10AA-A24-F1:
                                    (SEQ ID NO: 18)
5'-GGATCCGGCGGAGGCGGCTCGGGTGGCGGCGGCGGCTCTGGATCTCC

CACTCCATGAGGTATTTCTCC-3'

Bgl-A24-R1:
                                    (SEQ ID NO: 19)
5'-AGATCTACAGGCGATCAGGTAGGCGCCCC-3'
```

Example 2: Cloning of cDNA of Human β2 Microglobulin

Subsequently, cDNA of human β2 microglobulin was cloned via RT-PCR using total RNA prepared from the HepG2 human tumor cell line as a template on the basis of the sequence information for cDNA of human β2 microglobulin (GenBank Accession No. NM_004048.2). In such a case, a sequence encoding a peptide of 5 amino acids including a BamHI recognition sequence was added to the C terminus, so as to bind the cDNA fragment to HLA α1 and α2 regions. In order to knock-in the artificial chimeric gene into a site corresponding to the first methionine of mouse β2 microglobulin and express the artificial chimeric gene on a cell membrane upon normal processing, a leader sequence of HLA-A24 comprising an NcoI recognition sequence was added to the N terminus. Specifically, PCR was carried out using the primers shown below, and a 386-bp DNA fragment modified as described above was obtained.

```
Nco-A24L-hB2m-F1:
                                        (SEQ ID NO: 20)
5'-CCATGGCCGTCATGGCGCCCCGAACCCTCGTCCTGCTACTCTCGGGG

GCCCTGACCCAGACCTGGGCGATCCAGCGTACTCCAAAGATTCAGGT-3'

Bam-5AA-hB2m-R1:
                                        (SEQ ID NO: 21)
5'-GGATCCGCCACCTCCACTGTCTCGATCCCACTTAACTATC-3'
```

Example 3: Cloning of Partial Sequence of Mouse H-2D$^b$ Gene

On the basis of sequence information for mouse H-2D$^b$ (GenBank Accession No. M37681.1), regions downstream of α3 region including the intracellular domain (i.e., exons 4 to 8 and introns 3 to 7) were cloned via PCR using genomic DNA of the C57BL6/N mouse as a template. In order to bind the sequence to the HLA α1 and α2 regions and to facilitate vector construction, the BamHI recognition sequence was added to intron 3 at the N terminus and, for example, the SwaI recognition sequence was added to the C terminus. Specifically, PCR was carried out using the primers shown below, and a 2494-bp DNA fragment modified as described above was obtained.

```
Bam-H2Db-F1:
                                        (SEQ ID NO: 22)
5'-GGATCCTGTGTGACATACCTGTACCTTGTC-3'

Swa-H2Db-R1:
                                        (SEQ ID NO: 23)
5'-ATTTAAATCTAGTTGAGTCTCTGATCTTTAGCCCTAGG-3'
```

Example 4: Construction of Artificial Chimeric Gene (HHD-A2402)

The cDNA fragment of human β2 microglobulin, the human HLA-A2402 genome fragment, and the mouse H-2D$^b$ genome fragment obtained in the manner described above were ligated to each other, so as to construct an artificial chimeric gene of interest (full length: 3,735 bp, HHD-A2402) (FIG. 1).

Example 5: Preparation of Targeting Vector

Figure 2:
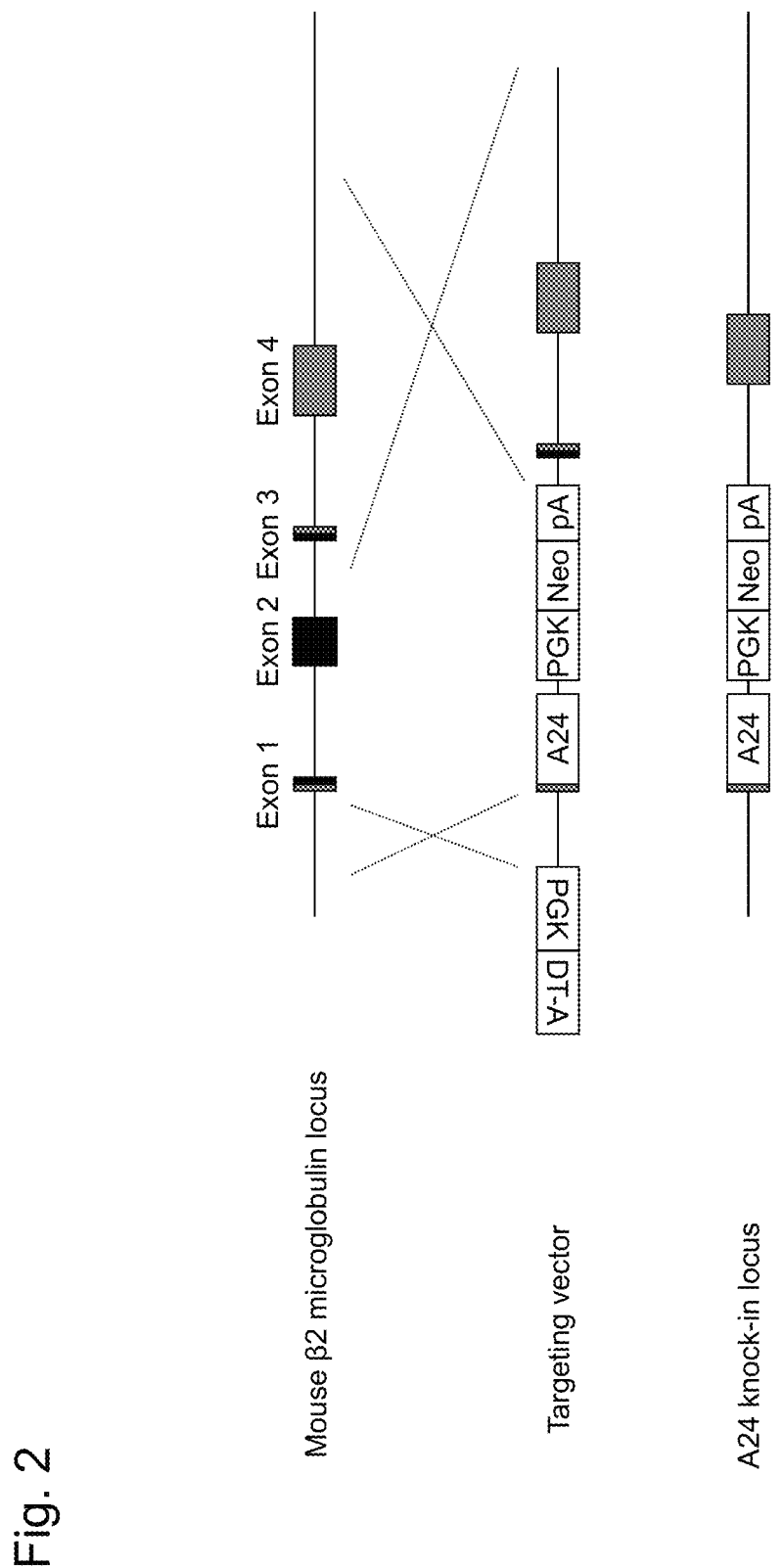
FIG. 2 schematically shows a method for knocking in the artificial chimeric gene into β2 microglobulin loci via homologous recombination.

Subsequently, a targeting vector used to knock-in the artificial chimeric gene (HHD-A2402) prepared above into mouse β2 microglobulin gene as shown in FIG. 2 was prepared.

On the basis of the sequence information for mouse β2 microglobulin cDNA (GenBank Accession No. NM_009735.3), at the outset, a genome sequence necessary for homologous recombination in an ES cell was cloned from the genome region including the mouse β2 microglobulin gene (GenBank Accession No. NC_000068.7). Specifically, PCR was carried out with the use of genomic DNA of the C57BL6/N mouse as a template, so as to clone a region of about 1.2 kb upstream of the first methionine of the mouse β2 microglobulin gene. In order to bind the fragment to the artificial chimeric gene (HHD-A2402) and to facilitate vector construction, the SalI recognition sequence and the NcoI recognition sequence were added to the 5' terminus and the 3' terminus, respectively. Specifically, PCR was carried out using the primers shown below, and a 1,198-bp DNA fragment modified as described above was obtained.

```
B2m-SHA-F1:
                                        (SEQ ID NO: 24)
5'-GTCGACCTGGGTAGACACTGTAGGATTGGGTCTCTG-3'

B2m-SHA-R1:
                                        (SEQ ID NO: 25)
5'-CCATGGTGACGACTGAAGCGACCGCGACTG-3'
```

Subsequently, a full-length 8,462-bp genome fragment from the NheI recognition sequence of intron 2 to the SacII recognition sequence of intron 4 was cloned from the BAC clone (RP23-34E24) comprising the genomic DNA sequence of the mouse β2 microglobulin gene.

Figure 3:
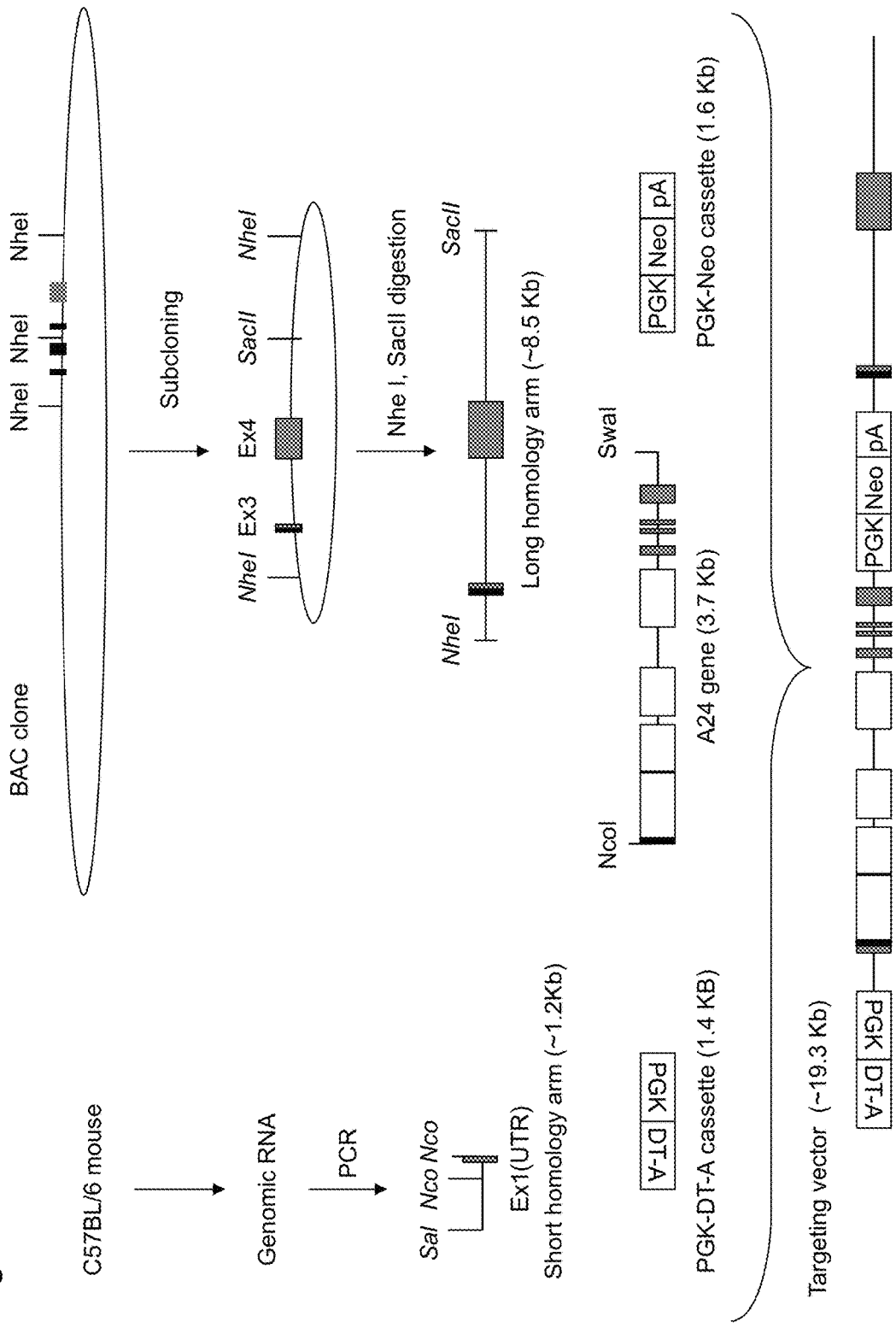
FIG. 3 schematically shows a structure of a targeting vector used for preparing an HLA class I gene knock-in mouse (HLA-A24).

The genome fragment of the mouse β2 microglobulin gene obtained in the manner described above and the artificial chimeric gene (HHD-A2402) were cloned into the pBluescript II KS+ plasmid together with the PGK-DT-A cassette and the PGK-neo-bpA cassette. Thus, a targeting vector of interest (full length: about 19.2 kb) was prepared (FIG. 3).

Example 6: Introduction of Targeting Vector into ES Cell

Subsequently, the targeting vector prepared in Example 5 was introduced into ES cells.

CMTI-1 cells purchased from Millipore (Passage 11) were used as ES cells. The cells described in the examples below were cultured with the use of the Dulbecco's modified Eagle's medium (DMEM) (Life Technologies) supplemented with 20% FBS (ES cell-qualified fetal bovine serum) (Life Technologies) and 10$^3$ units/ml of leukocyte inhibitory factors (LIF) (Millipore) in an incubator at 37° C. in the presence of 5% CO$_2$.

The targeting vector prepared in Example 5 (50 µg) was cleaved with NotI, dissolved in 0.2 ml of an electroporation buffer for ES cells (Millipore), and mixed with 2×10$^7$ CMTI-1 cells suspended in 0.3 ml of an electroporation buffer in an electroporation cuvette (Bio-Rad). Thereafter, electric pulses were applied using the Gene Pulser II (Bio-Rad) at 250 V and 500 µF, and the resultant was added in amounts of 0.1 ml/dish to five 10-cm dishes in which neomycin resistant feeder cells (DS Pharma) had been sowed in advance. G418 (titer: 250 µg/ml, Nacalai Tesque) was added thereto 12 to 18 hours thereafter, and culture was conducted for 1 week.

Example 7: Selection and Confirmation of Homologously Recombined ES Cell

ES cell colonies (384 colonies) developed as a result of culture for 1 week after the addition of G418 in Example 6 were sampled. The colonies were divided into two, and one of them was continuously cultured. The other was washed with PBS, treated with proteinase K, and subjected to PCR using the primers shown below. Three homologously recombined clones were selected.

HHD-HRES-F1:
(SEQ ID NO: 26)
5'-AGCATTTCCTAGTACAGTTCAACACAGTGTTTAGT-3'

HHD-HRES-R1:
(SEQ ID NO: 27)
5'-GAGTAGCAGGACGAGGGTTCGGGGCGCCAT-3'

A PCR cycle of 94° C. for 30 seconds, 60° C. for 1 minute, and 72° C. for 2 minutes was repeated 35 times. The PCR product was subjected to 1% agarose gel electrophoresis, so as to detect a PCR product (about 1.4 kb) that was deduced to develop upon proper homologous recombination. It was determined that clones in which such PCR product was detected were positive clones.

In order to confirm homologous recombination with higher accuracy, genomic DNA was extracted from the ES cell clones determined to be the positive clones above and analyzed via Southern blotting in the manner described below.

Figure 4:
FIG. 4 shows a photograph demonstrating the results of analysis of genotypes of homologously recombined ES cells via Southern blotting.

Genomic DNA (10 μg) was cleaved with the EcoRI restriction enzyme, subjected to 1% agarose gel electrophoresis, and then transferred onto a nylon membrane (Hybond-N+, Pharmacia) with the use of a 10×SSC solution by the capillary method. Further, a DNA fragment of about 0.5 kb in a 5'-upstream region of the 1,198-bp DNA fragment cloned in Example 5 was prepared. Southern hybridization was carried out using the DNA fragment labeled with [α-$^{32}$P]-dCTP (Perkin Elmer) as a probe. As a result, a band of about 2.1 kb resulting from proper homologous recombination and a 2.5-kb band derived from a wild type were detected at 1:1 (FIG. 4).

Example 8: Preparation of Artificial Chimeric Gene (HHD-A2402) Knock-In Transgenic Animal Homologously recombined ES cells were separately dispersed via trypsin treatment. A male mouse of the C57BL/6 strain was subjected to crossing with a female mouse of the same strain, the blastocysts were took out from the female mouse, and about 10 ES cells described above were injected into the segmentation cavity per blastocyst using a microinjection apparatus (Narishige). The resultants were transplanted into the uterus of the pseudopregnant female mouse, and fetal development was continued. Thus, a chimeric mouse was obtained.

The male chimeric mouse was subjected to crossing with a female mouse of the C57BL/6 strain, those exhibiting the color of the wild type (agouti) were selected from among the resulting offspring mice, and parts of the tails were cut to prepare samples. Genomic DNA was extracted from the samples and subjected to PCR using the primers shown below.

HHD-F1:
(SEQ ID NO: 28)
5'-CTAGAAGCAAGGTCAGAAATCCTCT-3'

HHD-WT-R3:
(SEQ ID NO: 29)
5'-CCGTCAGCACACTCGCAAACAGGCG-3'

HHD-HRES-R1:
(SEQ ID NO: 30)
5'-GAGTAGCAGGACGAGGGTTCGGGGCGCCAT-3'

A PCR cycle of 94° C. for 30 seconds, 60° C. for 1 minute, and 72° C. for 1 minute was repeated 35 times, and the PCR product was analyzed via 1% agarose gel electrophoresis. When a 510-bp PCR product deduced to develop upon proper homologous recombination was detected in addition to the 804-bp PCR product derived from the wild-type gene locus, it was determined that the examined mice were heterozygous knock-in mice.

Heterozygous knock-in mice were subjected to crossing with each other, genomic DNA was extracted from the samples obtained by cutting parts of the tails from the offspring mice, and genotypes thereof were analyzed via PCR described above. When a 804-bp PCR product derived from the wild-type gene locus was not detected and only a 510-bp PCR product deduced to develop upon proper homologous recombination was detected, it was determined that the examined mice were homozygous knock-in mice.

Figure 5:
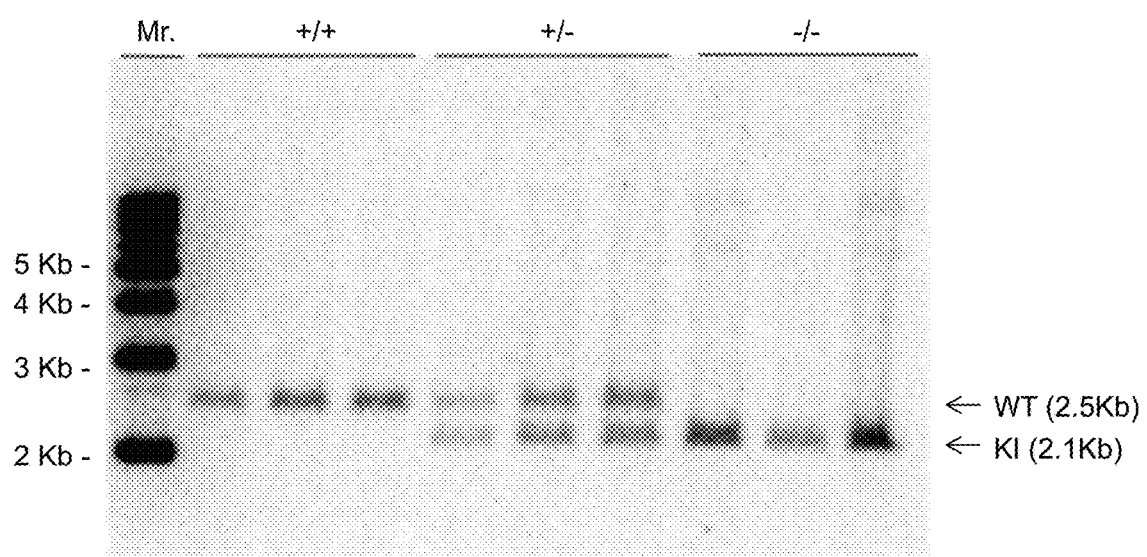
FIG. 5 shows a photograph demonstrating the results of analysis of genotypes of wild-type mice, heterozygous knock-in mice carrying an artificial chimeric gene, and homozygous knock-in mice carrying artificial chimeric genes via Southern blotting.

Genomic DNAs prepared from parts of the tails of homozygous mice, heterozygous mice, and wild-type mice (3 individuals each) identified via PCR were analyzed via Southern hybridization described in Example 7. As a result, a band of about 2.1 kb alone, bands of about 2.1 kb and about 2.5 kb, and a band of about 2.5 bp alone were detected for homozygous mice, heterozygous mice, and wild-type mice, respectively (FIG. 5).

Figure 6:
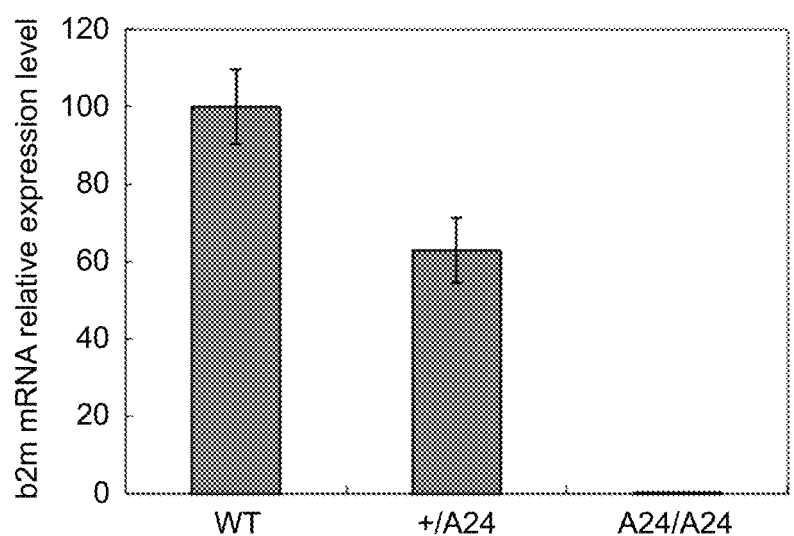
FIG. 6 shows the results of analysis of mouse β2 microglobulin mRNA expression levels in the livers of wild-type mice, heterozygous knock-in mice carrying an artificial chimeric gene, and homozygous knock-in mice carrying artificial chimeric genes via quantitative RT-PCR.

Homozygous mice, heterozygous mice, and wild-type mice (3 individuals each) were euthanized, total RNAs were prepared from the livers using Isogen (Wako Pure Chemical Industries, Ltd.) and the RNeasy kit (QIAGEN), followed by treatment with DNaseI, and cDNAs were then synthesized using the SuperScript III First-Strand Synthesized System (Life Technologies). After the addition of the TaqMan Assay Mix (Applied Biosystems) and the 2× TaqMan Universal Master Mix (Applied Biosystems) for the detection of mouse β2 microglobulin and ribosomal RNA, quantitative RT-PCR was carried out using the PRISM 7900 HT Sequence Detection System (Applied Biosystems). The results of analysis demonstrate that expression of mouse β2 microglobulin mRNA was substantially completely lost in homozygous mice and such expression in the heterozygous mice was decreased to a level that was about a half the expression level observed in wild-type mice (FIG. 6).

Example 9: Preparation of Artificial Chimeric Gene (HHD-A0301) Knock-In Transgenic Animal On the basis of the sequence information for human HLA-A0301 (GenBank Accession No. AJ748743.1), a gene fragment comprising the α1 and α2 regions was fully synthesized. Specifically, a sequence encoding a peptide of 10 amino acids including the BamHI recognition sequence was added to the N terminus, and the BglII recognition sequence was added within the intron 3 sequence on the C terminus side, so as to synthesize the 867-bp DNA fragment described below.

(SEQ ID NO: 31)
5'-ggatccggcggaggcggctcgggtggcggcggctctgGATCTCACTC

CATGAGGTATTTCTTCACATCCGTGTCCCGGCCCGGCCGCGGGGAGCCCC

GCTTCATCGCCGTGGGCTACGTGGACGACACGCAGTTCGTGCGGTTCGAC

AGCGACGCCGCGAGCCAGAGGATGGAGCCGCGGGCGCCGTGGATAGAGCA

GGAGGGGCCGGAGTATTGGGACCAGGAGACACGGAATGTGAAGGCCCAGT

CACAGACTGACCGAGTGGACCTGGGGACCCTGCGCGGCTACTACAACCAG

AGCGAGGCCGgtgagtgaccccggccggtggcgcaggtcaggacccctca

-continued
```
tccccacggacgggccaggtcgcccacagtctccgggtccgagatccac cccgaagccgcgggaccccgagacccttgccccgggagaggcccaggcgc ctttacccggtttcattttcagtttaggccaaaaatcccccgggttggt cggggctgggcgggctcgggggactgggctgaccgcgggtcggggcca gGTTCTCACACCATCCAGATAATGTATGGCTGCGACGTGGGGTCGGACGG

GCGCTTCCTCCGCGGGTACCGGCAGGACGCCTACGACGGCAAGGATTACA

TCGCCCTGAACGAGGACCTGCGCTCTTGGACCGCGGCGGACATGGCGGCT

CAGATCACCAAGCGCAAGTGGGAGGCGGCCCATGAGGCGGAGCAGTTGAG

AGCCTACCTGGATGGCACGTGCGTGGAGTGGCTCCGCAGATACCTGGAGA

ACGGGAAGGAGACGCTGCAGCGCACGGgtaccaggggccacggggcgcct ccctgatcgcctgtagatct-3'
(uppercase letters indicate exon regions and
lowercase letters indicate intron regions)
```

In accordance with the methods described in Examples 2 to 8, HHD-A0301 heterozygous knock-in mice and HHD-A0301 homozygous knock-in mice were prepared.

Example 10: Preparation of Artificial Chimeric Gene (HHD-A0201) Knock-In Transgenic Animal On the basis of the sequence information for human HLA-A0201 (GenBank Accession No. AY365426.1), a gene fragment comprising the α1 and α2 regions was fully synthesized. Specifically, a sequence encoding a peptide of 10 amino acids including the BamHI recognition sequence was added to the N terminus, and the BglII recognition sequence was added within the intron 3 sequence on the C terminus side, so as to synthesize the 867-bp DNA fragment described below.

```
                                           (SEQ ID NO: 43)
5'-ggatccggcggaggcggctcgggtggcggcggctctgGATCTCACTC

CATGAGGTATTTCTTCACATCCGTGTCCCGGCCCGGCCGCGGGGAGCCCC

GCTTCATCGCAGTGGGCTACGTGGACGACACGCAGTTCGTGCGGTTCGAC

AGCGACGCCGCGAGCCAGAGGATGGAGCCGCGGGCGCCGTGGATAGAGCA

GGAGGGTCCGGAGTATTGGGACGGGGAGACACGGAAAGTGAAGGCCCACT

CACAGACTCACCGAGTGGACCTGGGGACCCTGCGCGGCTACTACAACCAG

AGCGAGGCCGgtgagtgaccccggccggtggcgcaggtcaggaccectca tccccacggacgggccaggtcgcccacagtctccgggtccgagatccac cccgaagccgcgggaccccgagacccttgccccgggagaggcccaggcgc ctttcccggtttcattttcagtttaggccaaaaatcccccgggttggtc ggggctgggcgggctcgggggactgggctgaccgcgggtcggggccag

GTTCTCACACCGTCCAGAGGATGTATGGCTGCGACGTGGGGTCGGACTGG

CGCTTCCTCCGCGGGTACCACCAGTACGCCTACGACGGCAAGGATTACAT

CGCCCTGAAAGAGGACCTGCGCTCTTGGACCGCGGCGGACATGGCAGCTC

AGACCACCAAGCACAAGTGGGAGGCGGCCCATGTGGCGGAGCAGTTGAGA
```

```
GCCTACCTGGAGGGCACGTGCGTGGAGTGGCTCCGCAGATACCTGGAGAA

CGGGAAGGAGACGCTGCAGCGCACGGgtaccaggggccacggggcgcctc cctgatcgcctgtagatct-3'
(uppercase letters indicate exon regions and
lowercase letters indicate intron regions)
```

In accordance with the methods described in Examples 2 to 8, HHD-A0201 heterozygous knock-in mice and HHD-A0201 homozygous knock-in mice were prepared.

Example 11: Preparation of Artificial Chimeric Gene (HHD-A3101) Knock-In Transgenic Animal On the basis of the sequence information for human HLA-A3101 (GenBank Accession No. M84375.1), a gene fragment comprising the α1 and α2 regions was fully synthesized. Specifically, a sequence encoding a peptide of 10 amino acids including the BamHI recognition sequence was added to the N terminus, and the BglII recognition sequence was added within the intron 3 sequence on the C terminus side, so as to synthesize the 867-bp DNA fragment described below.

```
                                           (SEQ ID NO: 44)
5'-ggatccggcggaggcggctcgggtggcggcggctctgGATCTCACTC

CATGAGGTATTTCACCACATCCGTGTCCCGGCCCGGCCGCGGGGAGCCCC

GCTTCATCGCCGTGGGCTACGTGGACGACACGCAGTTCGTGCGGTTCGAC

AGCGACGCCGCGAGCCAGAGGATGGAGCCGCGGGCGCCGTGGATAGAGCA

GGAGAGGCCTGAGTATTGGGACCAGGAGACACGGAATGTGAAGGCCCACT

CACAGATTGACCGAGTGGACCTGGGGACCCTGCGCGGCTACTACAACCAG

AGCGAGGCCGgtgagtgaccccggccggtggcgcaggtcaggaccectca tccccacggacgggccaggtcgcccacagtctccgggtcgagatccac cccgaagccgcgggaccccgagacccttgccccgggagaggcccaggcgc ctttacccggtttcattttcagtttaggccaaaaatcccccgggttggt cggggctgggcgggctcgggggactgggctgaccgcgggtcggggcca gGTTCTCACACCATCGAGATGATGTATGGCTGCGACGTGGGGTCGGACGG

GCGCTTCCTCCGCGGGTACCAGCAGGACGCCTACGACGGCAAGGATTACA

TCGCCTTGAACGAGGACCTGCGCTCTTGGACCGCGGCGGACATGGCGGCT

CAGATCACCCAGCGCAAGTGGGAGGCGGCCCGTGTGGCGGAGCAGTTGAG

AGCCTACCTGGAGGGCACGTGCGTGGAGTGGCTCCGCAGATACCTGGAGA

ACGGGAAGGAGACGCTGCAGCGCACGGgtaccaggggccacggggcgcct ccctgatcgcctgtagatct-3'
(uppercase letters indicate exon regions and
lowercase letters indicate intron regions)
```

In accordance with the methods described in Examples 2 to 8, HHD-A3101 heterozygous knock-in mice and HHD-A3101 homozygous knock-in mice were prepared.

Example 12: Preparation of HHD-A2402 and HHD-A0301 Knock-In Transgenic Animal

HHD-A2402 homozygous knock-in mice were subjected to crossing with HHD-A0301 homozygous knock-in mice to prepare double knock-in mice carrying one copy each of the HHD-A2402 and the HHD-A0301 genes.

Example 13: Confirmation of Human and Mouse MHC Class I Gene Expression in Knock-In Mice HHD-A2402 homozygous knock-in mice, HHD-A0301 homozygous knock-in mice, HHD-A2402 heterozygous knock-in mice, HHD-A0301 heterozygous knock-in mice, wild-type mice as control littermates, and HHD-A2402/HHD-A0301 double knock-in mice were euthanized, and human MHC class I gene expression on the surface of blood cells or spleen cells collected from the extracted spleens was analyzed via flow cytometry. Specifically, $1 \times 10^6$ spleen cells or blood cells were stained with monoclonal PE-labeled anti-HLA antibody 17A10 (MBL) or the biotinylated antibody 4i153 (Abeam) as the primary antibody and the PE-labeled anti-biotin antibody Bio3-18E7 (Miltenyi Biotec) as the secondary antibody.

Figures 1, 7:
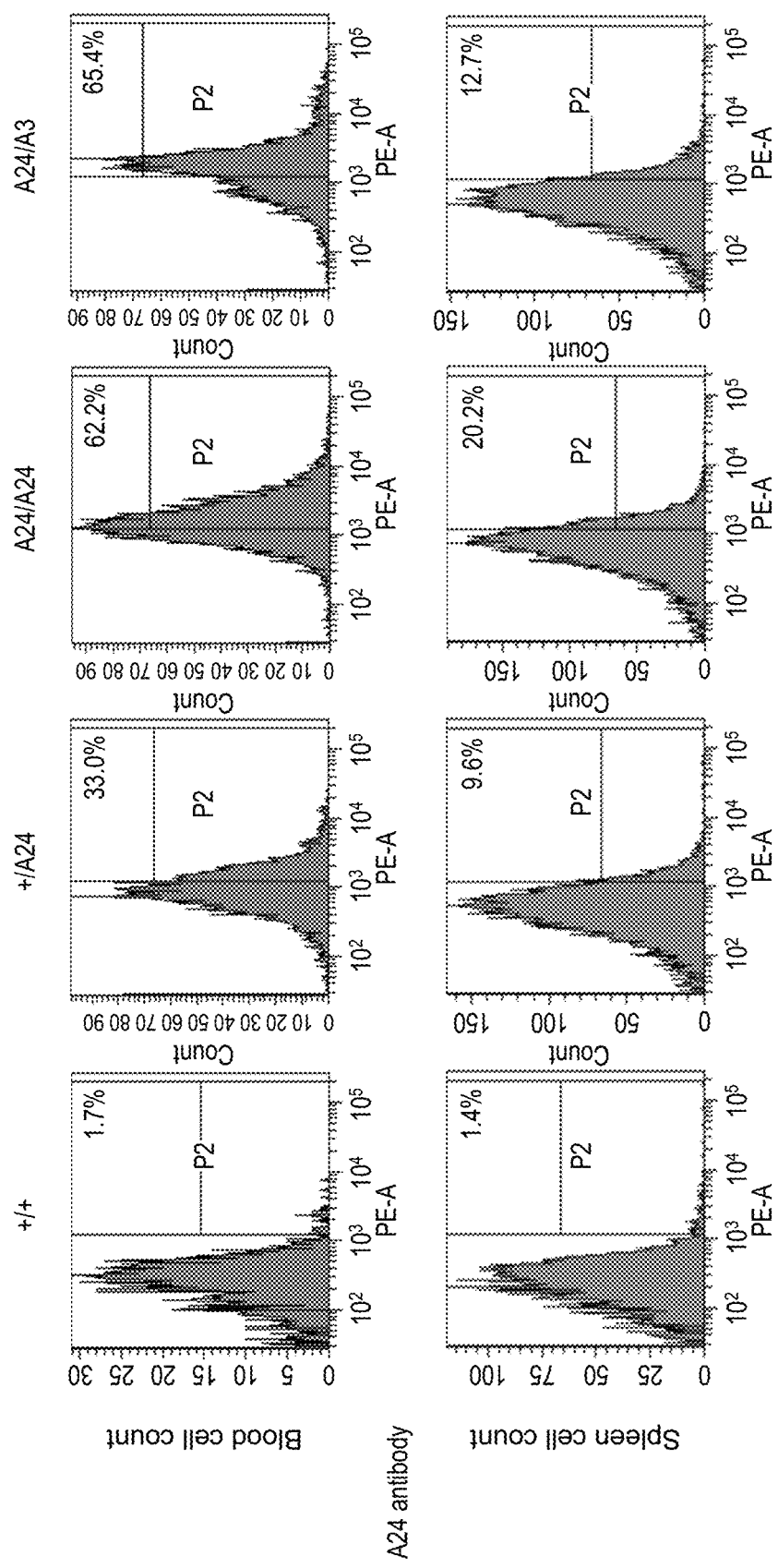
Figures 2, 7:
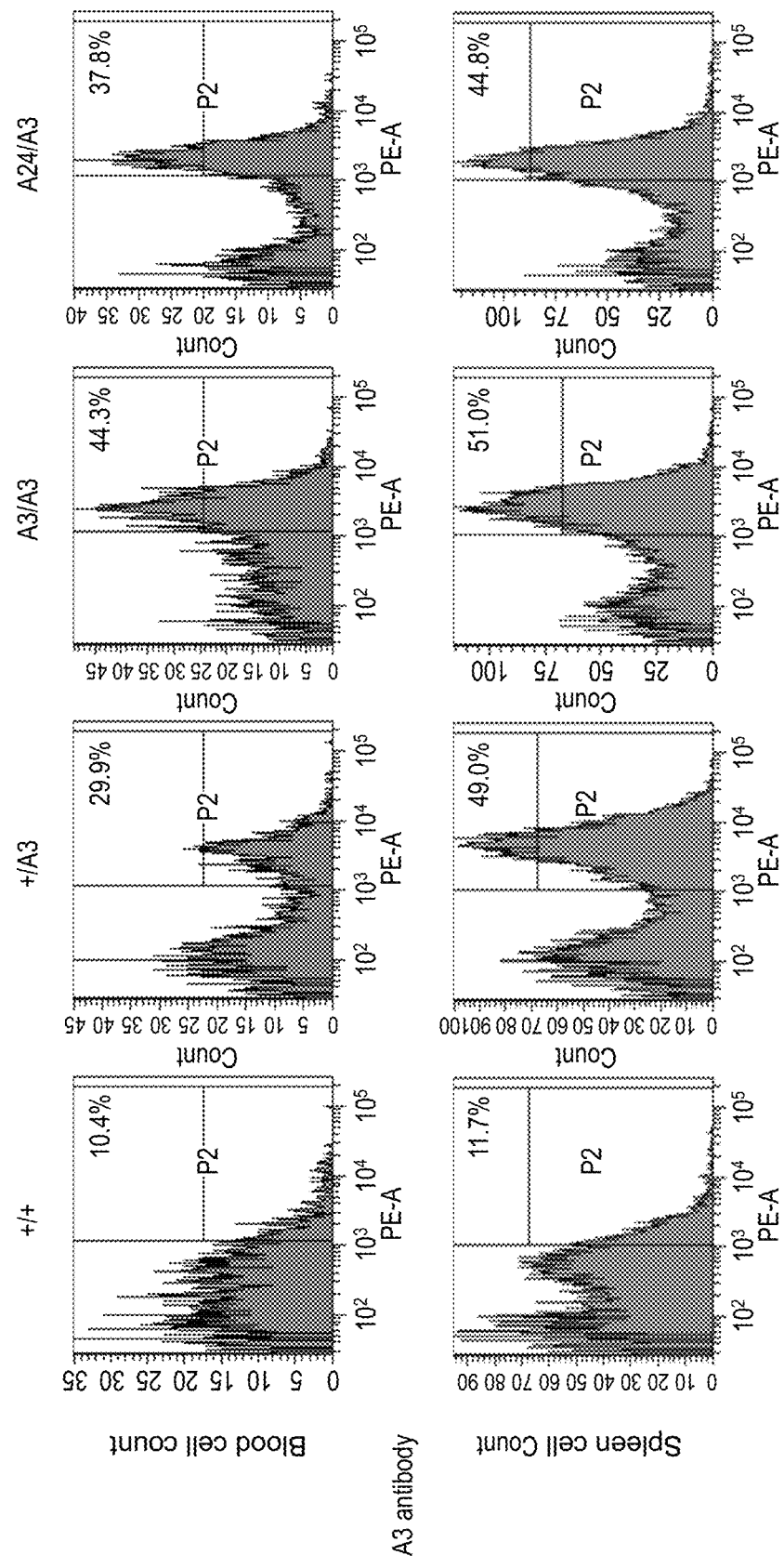

As a result, HLA-A24 expression was detected in HHD-A2402 homozygous knock-in mice and HHD-A2402 heterozygous knock-in mice, and HLA-A3 expression was detected in HHD-A0301 homozygous knock-in mice and HHD-A0301 heterozygous knock-in mice. In addition, expression of both HLA-A24 and HLA-A3 was detected in HHD-A2402/HHD-A0301 double knock-in mice (FIG. 7-1 and FIG. 7-2).

Figures 1, 8:
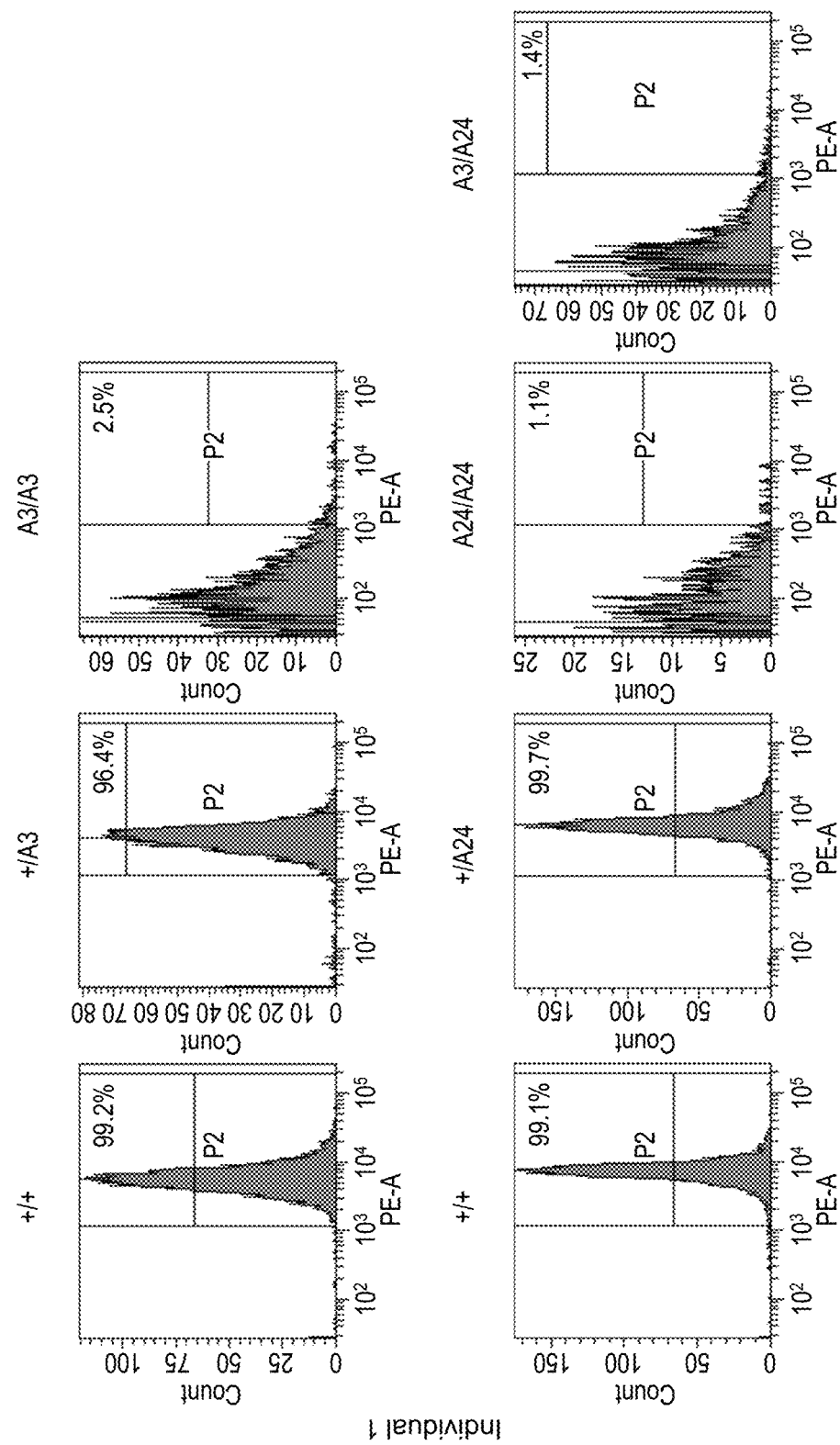
Figures 2, 8:
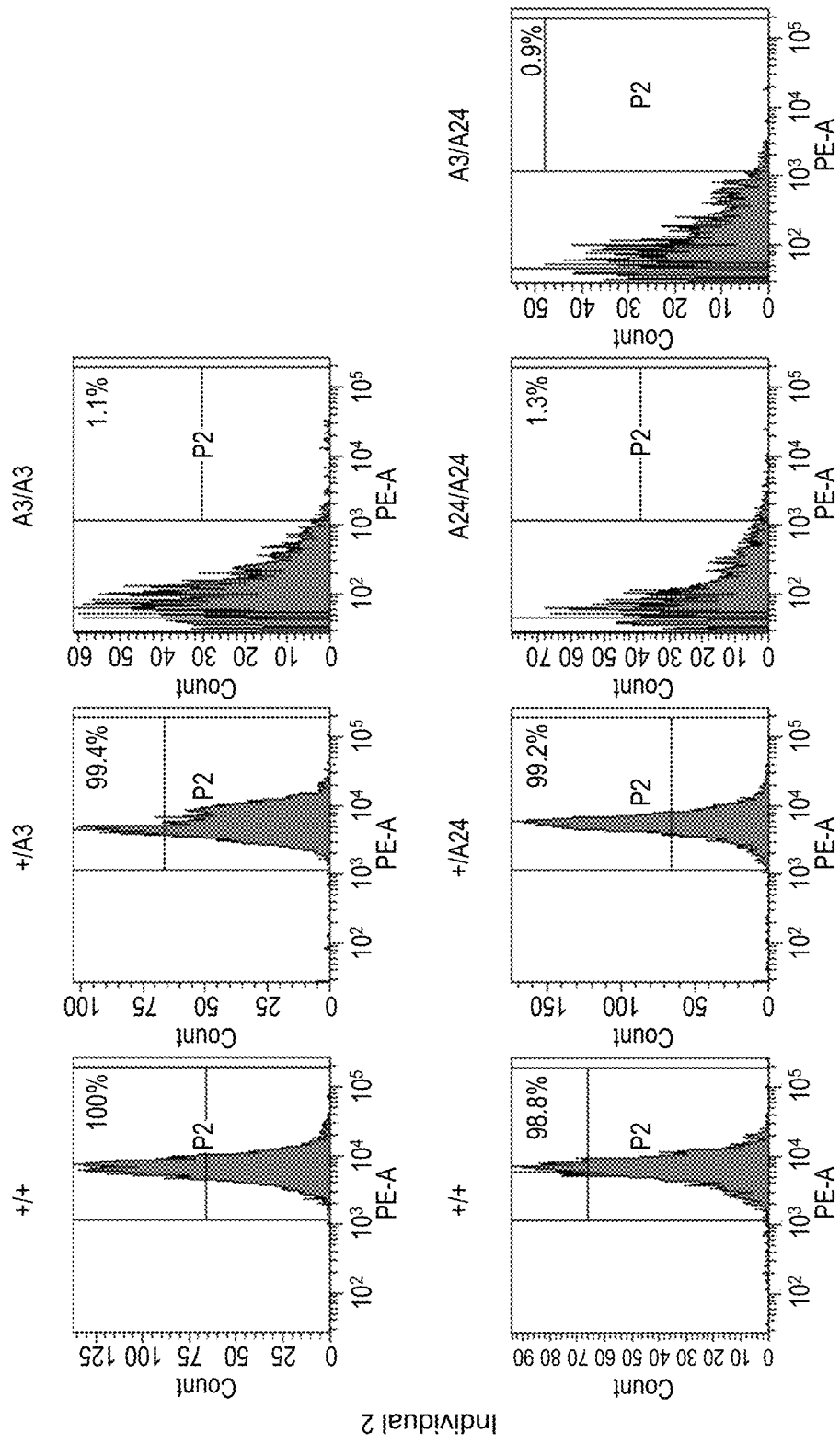

Further, endogenous mouse MHC class I gene expression on the spleen cell surface was analyzed using the PE-labeled anti-H-2K$^b$ antibody AF6-88.5 (BD Bioscience). As a result, H-2K$^b$ expression was detected in wild-type mice, HHD-A2402 heterozygous knock-in mice, and HHD-A0301 heterozygous knock-in mice. In contrast, H-2K$^b$ expression was almost completely lost in HHD-A2402 homozygous knock-in mice, HHD-A0301 homozygous knock-in mice, and HHD-A2402/HHD-A0301 double knock-in mice (FIG. 8-1 and FIG. 8-2).

With the use of the monoclonal PE-labeled anti-HLA-A2 antibody BB7.2 (MBL) and the monoclonal FITC-labeled anti-human β2 microglobulin antibody TU99 (BD Bioscience), HLA-A2 and human β2 microglobulin expression on the blood cell surface of HHD-A0201 homozygous knock-in mice, HHD-A0201 heterozygous knock-in mice, and wild-type mice as control littermates was inspected in the same manner. Also, human β2 microglobulin expression on the blood cell surface of HHD-A3101 homozygous knock-in mice, HHD-A3101 heterozygous knock-in mice, and wild-type mice as control littermates was inspected with the use of the monoclonal FITC-labeled anti-human β2 microglobulin antibody TU99.

Figures 1, 9:
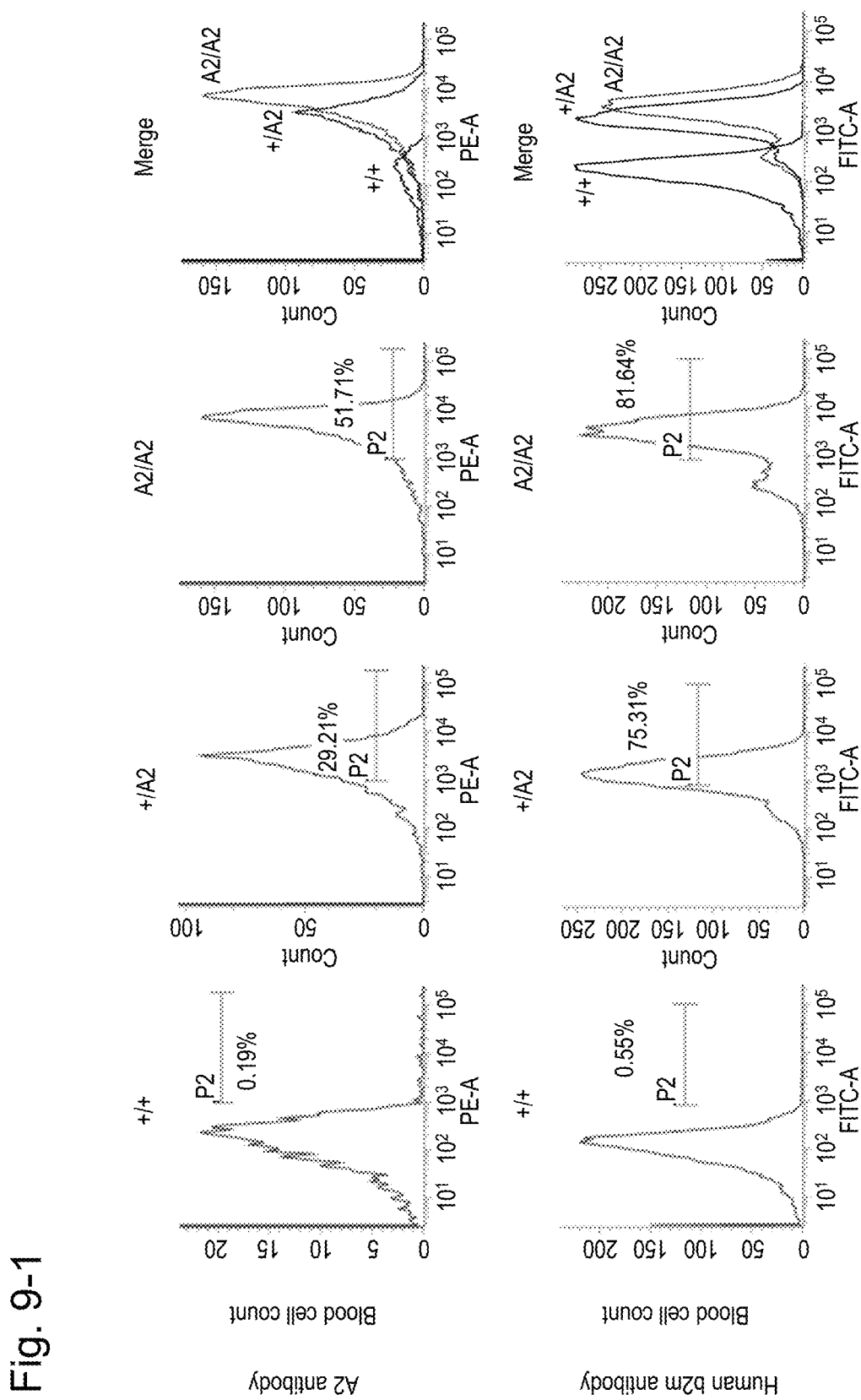
Figures 2, 9:
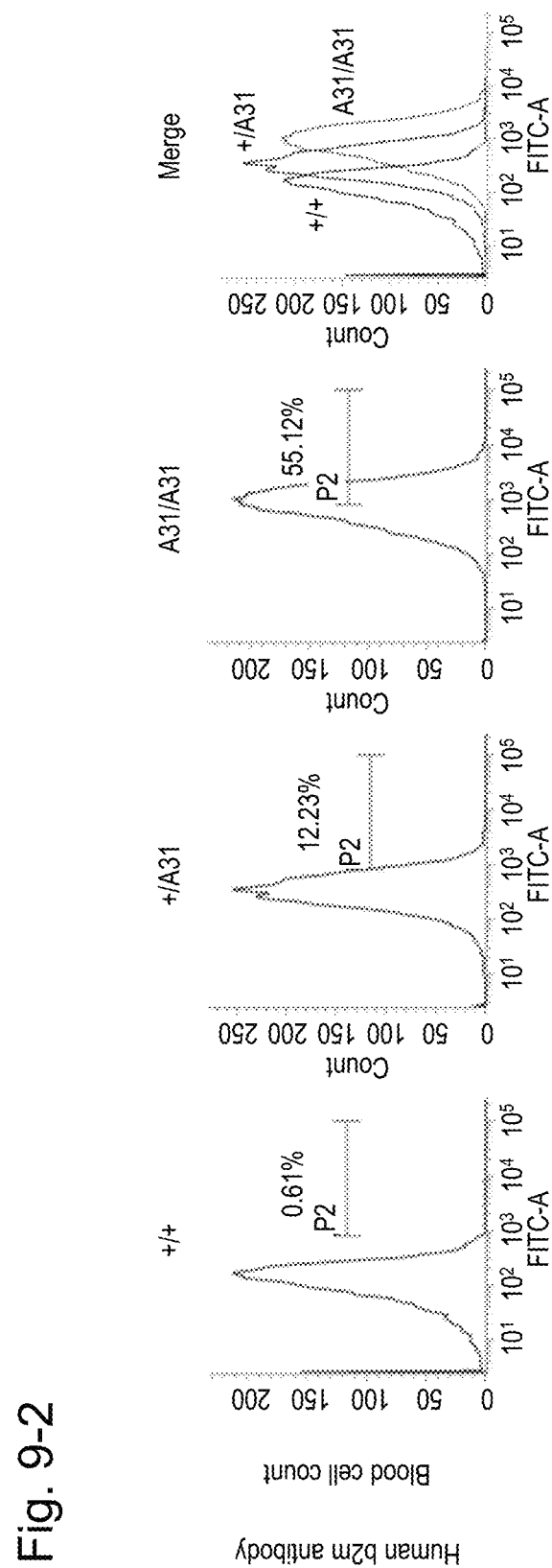

As a result, HLA-A2 and human β2 microglobulin expression was detected in HHD-A0201 homozygous knock-in mice and HHD-A0201 heterozygous knock-in mice (FIG. 9-1), and human β2 microglobulin expression was detected in HHD-A3101 homozygous knock-in mice and HHD-A3101 heterozygous knock-in mice (FIG. 9-2).

Figures 1, 10:
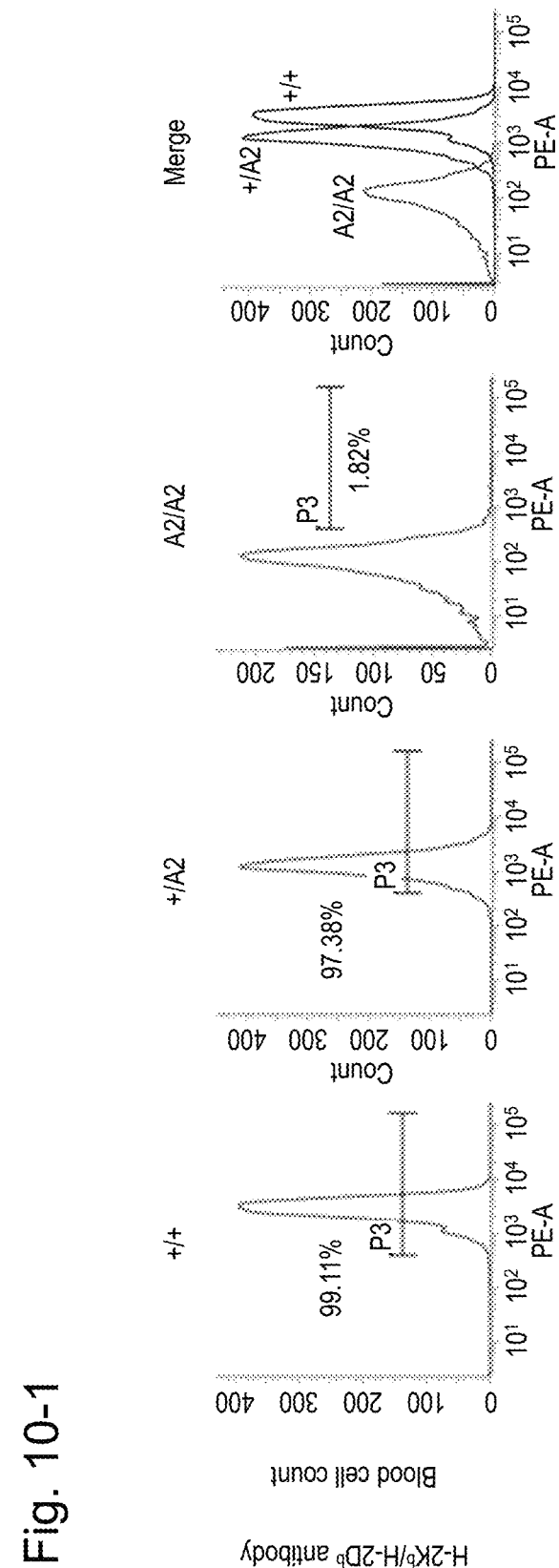
Figures 2, 10:
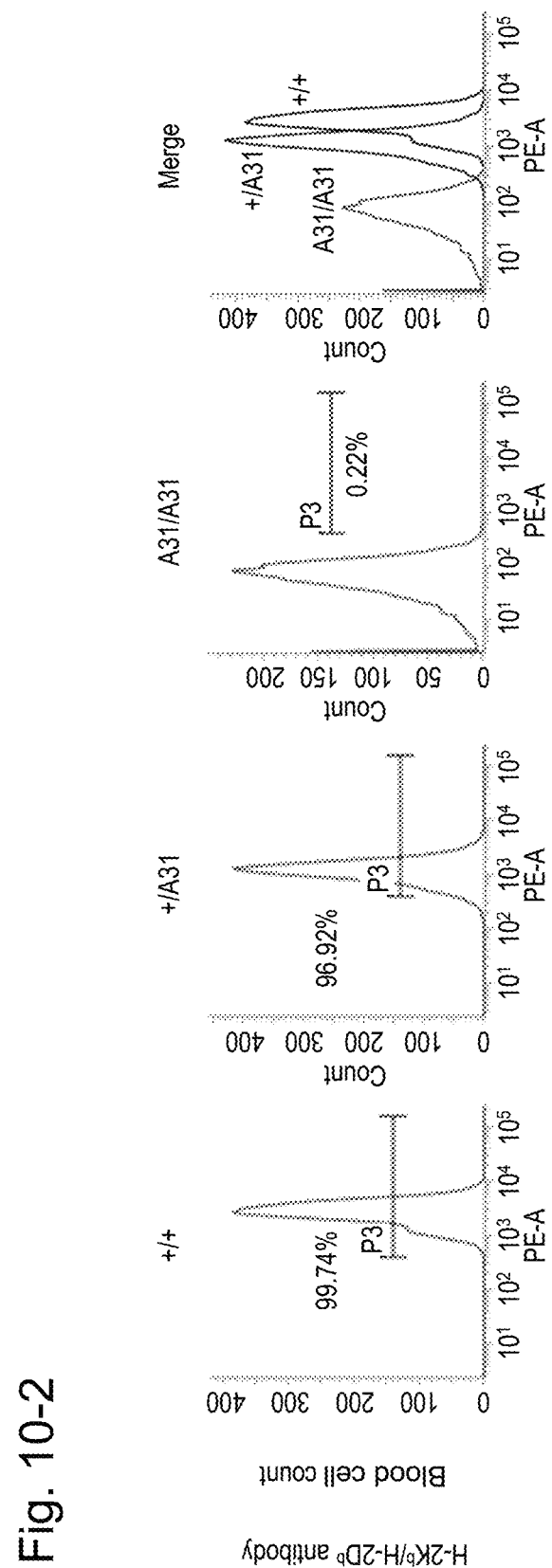

In addition, endogenous mouse MHC class I expression on the blood cell surface was analyzed using the PE-labeled anti-H-2K$^b$/H-2D$^b$ antibody 28-8-6 (Biolegend). As a result, H-2K$^b$ and/or H-2D$^b$ expression was detected in wild-type mice, HHD-A0201 heterozygous knock-in mice, and HHD-A3101 heterozygous knock-in mice; however, H-2K$^b$ and H-2D$^b$ expression was almost completely lost in HHD-A0201 homozygous knock-in mice and HHD-A3101 homozygous knock-in mice (FIG. 10-1 and FIG. 10-2).

Example 14: Confirmation of CTL Induction Capacity in A24 Knock-In Mice

The virus-derived antigen peptides or negative control peptides described below were dissolved at 2 mg/ml in Otsuka distilled water (Otsuka Pharmaceutical Factory, Inc.) and filled into a B Braun Injekt syringe.

A24V6:
(SEQ ID NO: 32)
EYLVSFGVW (A24-restricted HBV-derived antigen)

A24V8:
(SEQ ID NO: 33)
SFHSLHLLF (A24-restricted HTLV-derived antigen)

A24V9:
(SEQ ID NO: 34)
DYCNVLNKEF (A24-restricted EBV-derived antigen)

A24V10:
(SEQ ID NO: 35)
RYLRDQQLL (A24-restricted HIV-derived antigen)

Figure 11:
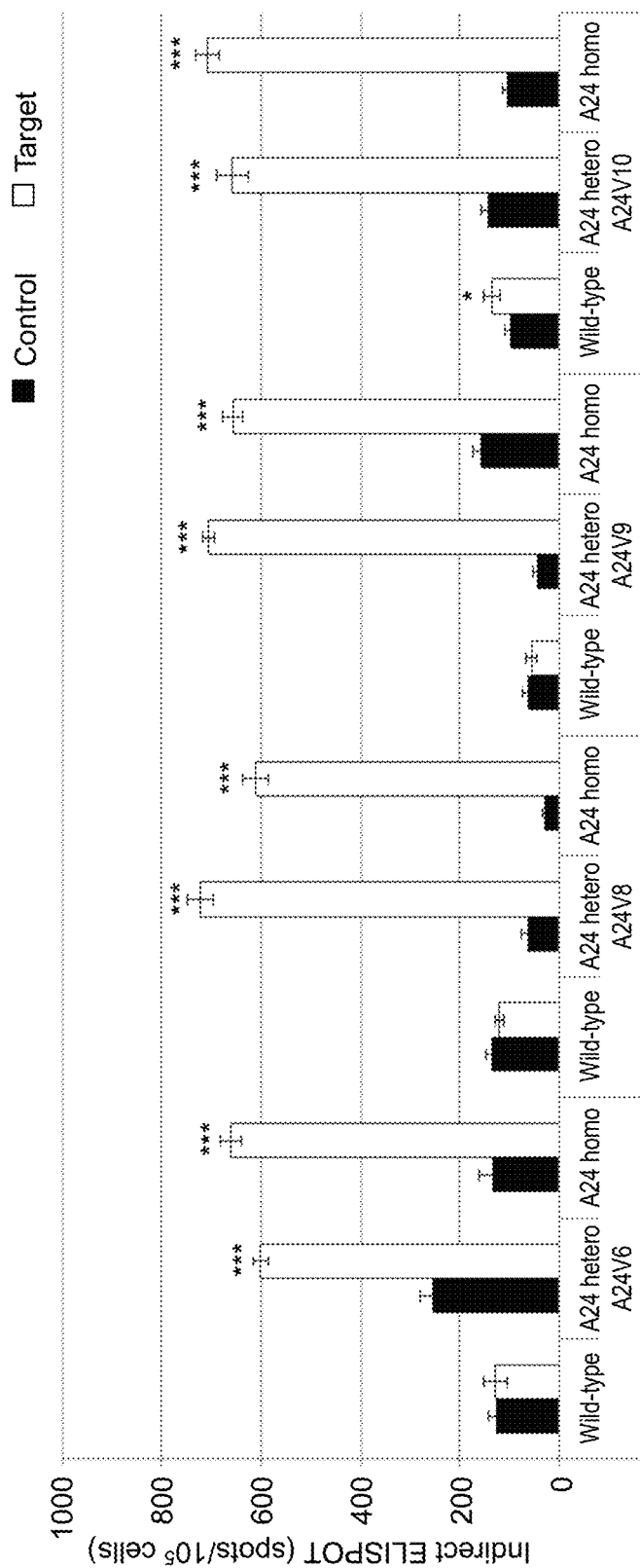
FIG. 11 shows the results of evaluation of the capacity of virus-derived antigen peptides for CTL induction using wild-type mice, heterozygous knock-in mice carrying an artificial chimeric gene (including HLA-A24), and homozygous knock-in mice carrying artificial chimeric genes (including HLA-A24) (*** indicates p<0.001).

After another syringe was filled with an equivalent amount of Incomplete Freund's adjuvant (IFA), these syringes were connected together with the aid of a GP syringe connector, and the solution of virus-derived antigen peptides was thoroughly mixed with IFA to prepare an emulsion. The emulsion was administered subcutaneously to A24 homozygous knock-in mice, A24 heterozygous knock-in mice, and wild-type littermate mice through the tail heads in amounts of 100 μl/mouse once per week, and administration was carried out twice in total. Lymph nodes of groins were recovered from the mice 1 week after the final administration. A suspension of lymph node cells was prepared by adjusting the cell concentration to $5 \times 10^6$ cell/ml with the aid of a complete medium (RPMI-1640, 10% heat-inactivated FBS, 100 U/ml penicillin, 100 μg/ml streptomycin, 50 μM 2-mercaptoethanol), the target CTL epitope peptide (final concentration: 10 μg/ml), the recombinant mouse IL-15 (final concentration: 100 ng/ml), and the recombinant mouse IL-21 (final concentration: 100 ng/ml) were added thereto, the resulting suspension was sowed into a 24-well plate at 1 ml/well, and culture was conducted in an incubator at 37° C. in the presence of 5% $CO_2$ for 8 days. Thereafter, the cells were recovered and sowed onto an anti-IFN-γ antibody-immobilized plate included in the Murine IFN-γ ELISpot Kit (GEN-PROBE) at $1 \times 10^5$ cells/well. Subsequently, the spleen cells obtained from the spleen of the mouse of the same strain and irradiated with X-rays at 30 Gy were sowed onto the same well as the antigen presenting cells at $1 \times 10^5$ cells/well, the target CTL epitope peptides or negative control peptides (final concentration: 10 μg/ml) were added, and culture was conducted in an incubator at 37° C. in the presence of 5% $CO_2$ overnight. The IFN-γ-producing cell spots were allowed to develop color in accordance with the instructions of the kit on the following day. The number of IFN-γ-producing cell spots was determined using the ELISPOT analyzer (Immunospot S6, Cellular Technology Ltd.). As a result, the number of IFN-γ-producing cell spots in the wells to which the virus-derived antigen peptides had been added was found to be significantly larger than that in the wells to which the negative control peptides had been added in both the A24 homozygous knock-in mice and the A24 heterozygous knock-in mice (Student's t-test, $p<0.001$), and the induction of epitope-specific CTL was observed, as shown in FIG. 11.

Example 15: Confirmation of CTL Induction Capacity in A3 Knock-In Mice

The virus-derived antigen peptides described below were dissolved at 2 mg/ml in Otsuka distilled water (Otsuka Pharmaceutical Factory, Inc.) and filled into a B Braun Injekt syringe.

A3V3:
(SEQ ID NO: 36)
RLRPGGKKK (A3-restricted HIV-derived antigen)

A3V4:
(SEQ ID NO: 37)
QVPLRPMTYK (A3-restricted HW-derived antigen)

A3V7:
(SEQ ID NO: 38)
RLRAEAQVK (A3-restricted EBV-derived antigen)

A3V10:
(SEQ ID NO: 39)
SIIPGPLK (A3-restricted influenza virus-derived antigen)

Figure 12:
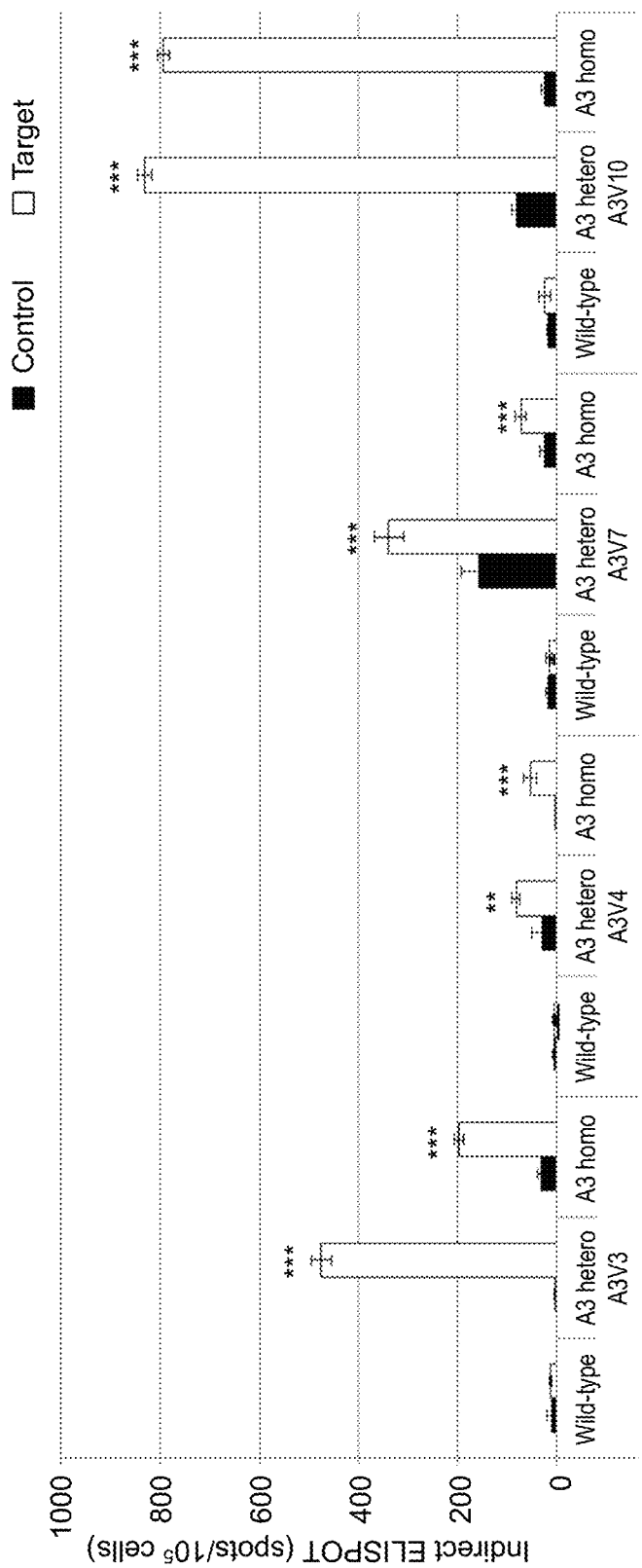
FIG. 12 shows the results of evaluation of the capacity of virus-derived antigen peptides for CTL induction using wild-type mice, heterozygous knock-in mice carrying an artificial chimeric gene (including HLA-A3), and homozygous knock-in mice carrying artificial chimeric genes (including HLA-A3) (* indicates p<0.001;  indicates p<0.01).

After another syringe was filled with an equivalent amount of Incomplete Freund's adjuvant (IFA), these syringes were connected together with the aid of a GP syringe connector, and the solution of virus-derived antigen peptides was thoroughly mixed with IFA to prepare an emulsion. The emulsion was administered subcutaneously to A3 homozygous knock-in mice, A3 heterozygous knock-in mice, and wild-type littermate mice through the tail heads in amounts of 100 μl/mouse once per week, and administration was carried out twice in total. The induction of virus-derived antigen peptide-specific CTL was then evaluated in accordance with the method described in Example 14. As a result, the number of IFN-γ-producing cell spots in the wells to which the virus-derived antigen peptides had been added was found to be significantly larger than that in the wells to which the negative control peptides had been added in both the A3 homozygous knock-in mice and the A3 heterozygous knock-in mice (Student's t-test, $p<0.01$ or $p<0.001$), and the induction of epitope-specific CTL was observed, as shown in FIG. 12.

Figure 13:
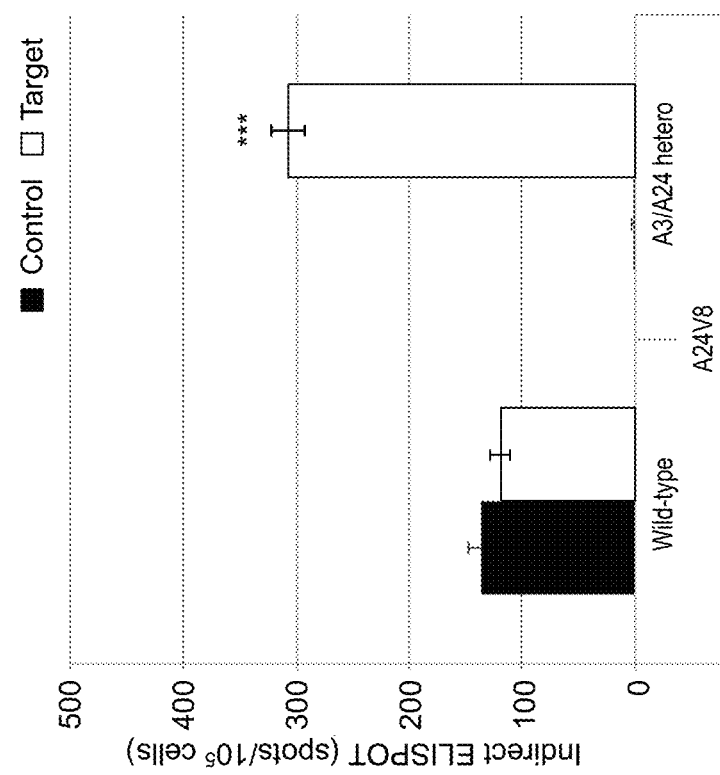
FIG. 13 shows the results of evaluation of the capacity of virus-derived antigen peptides for CTL induction using wild-type mice and double knock-in mice carrying the first artificial chimeric gene (including HLA-A24) and the second artificial chimeric gene (including HLA-A3) (*** indicates p<0.001).
Figure 13:
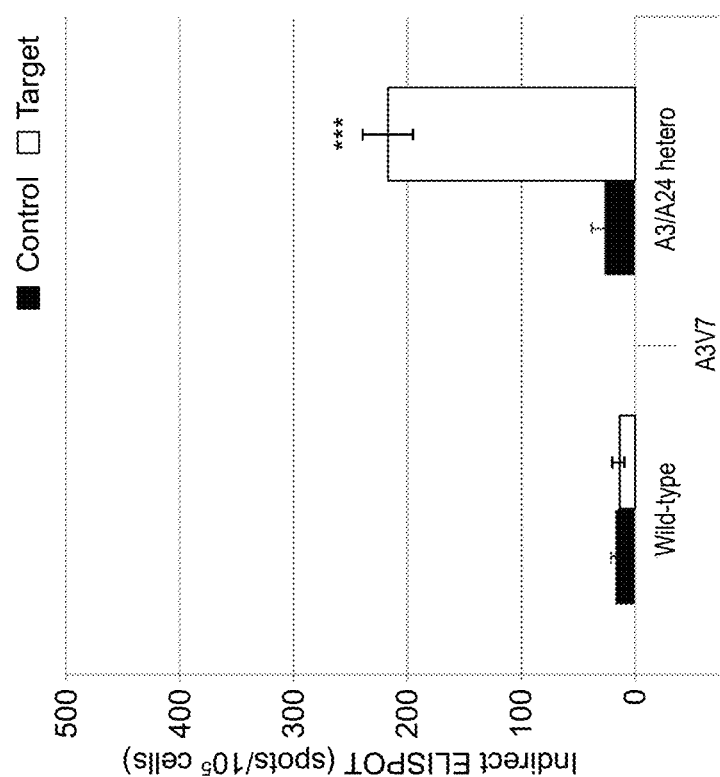

Example 16: Confirmation of CTL Induction Capacity in A24/A3 Double Knock-In Mice The virus-derived antigen peptides (A3V7 and A24V8) were administered to A24/A3 double knock-in mice and wild-type mice in the manner described above, and induction of virus-derived antigen peptide-specific CTL was evaluated in accordance with the method described in Example 14. As a result, the number of IFN-γ-producing cell spots in the wells to which the virus-derived antigen peptides had been added was found to be significantly larger than that in the wells to which the negative control peptides had been added in A24/A3 double knock-in mice (Student's t-test, $p<0.001$), and the induction of epitope-specific CTL was observed, as shown in FIG. 13.

Example 17: Confirmation of CTL Induction Capacity in A2 Knock-In Mice

The virus-derived antigen peptides described below were dissolved at 1 mg/ml in Otsuka distilled water (Otsuka Pharmaceutical Factory, Inc.) and filled into a B Braun Injekt syringe.

A2V1:
(SEQ ID NO: 45)
CLGGLLTMV

A2V2:
(SEQ ID NO: 46)
GLCTLVAML

A2V3:
(SEQ ID NO: 47)
NLVPMVATV

A2V4:
(SEQ ID NO: 48)
VLAELVKQI

A2V7:
(SEQ ID NO: 49)
VLSDFKTWL

A2V8:
(SEQ ID NO: 50)
FLPSDFFPSV

A2V9:
(SEQ ID NO: 51)
FLLTRILTI

A2V10:
(SEQ ID NO: 52)
GLSPTVWLS

Figure 14:
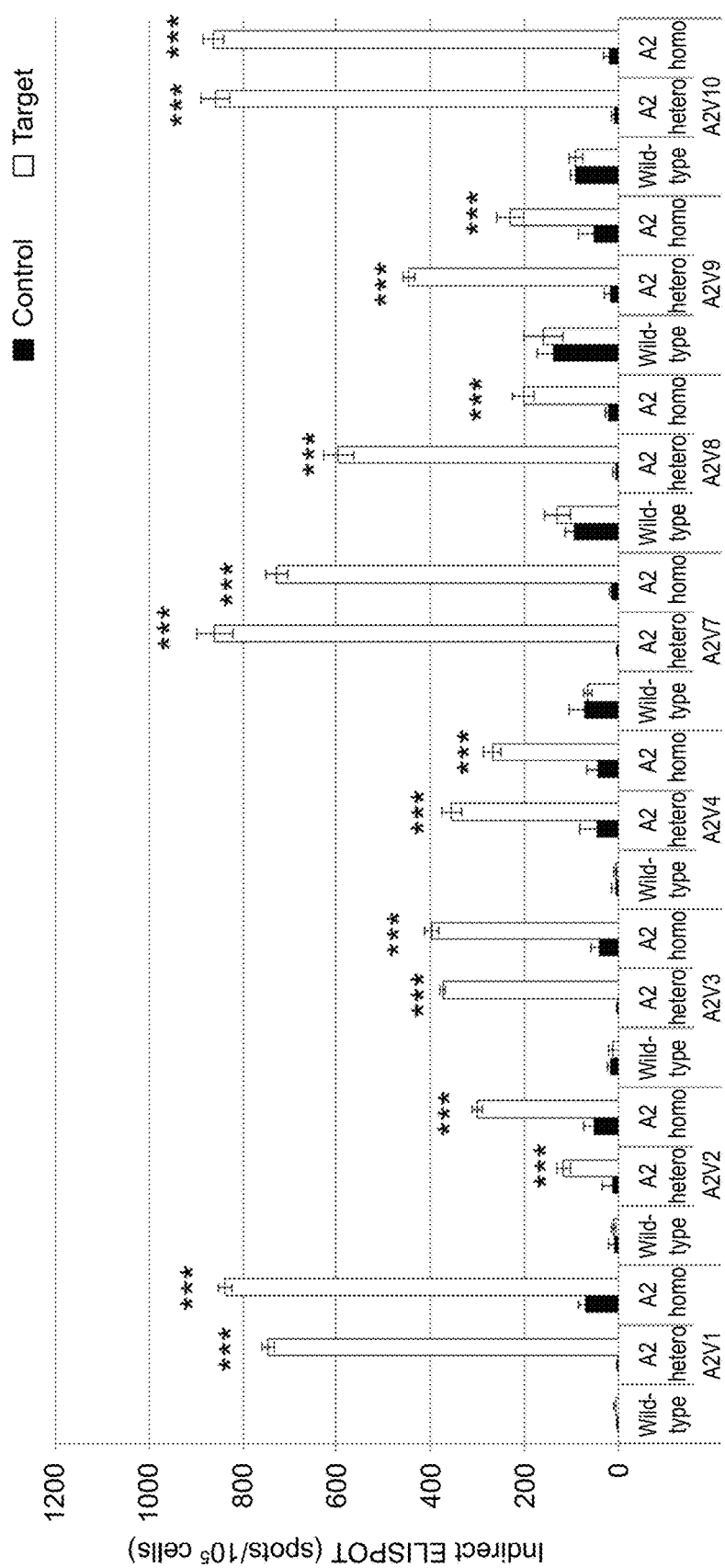
FIG. 14 shows the results of evaluation of the capacity of virus-derived antigen peptides for CTL induction using wild-type mice, heterozygous knock-in mice carrying an artificial chimeric gene (including HLA-A2), and homozygous knock-in mice carrying artificial chimeric genes (including HLA-A2) (*** indicates p<0.001).

After another syringe was filled with an equivalent amount of Incomplete Freund's adjuvant (IFA), these syringes were connected together with the aid of a GP syringe connector, and the solution of virus-derived antigen peptides was thoroughly mixed with IFA to prepare an emulsion. The emulsion was administered subcutaneously to A2 homozygous knock-in mice, A2 heterozygous knock-in mice, and wild-type littermate mice through the tail heads in amounts of 100 μl/mouse once per week, and administration was carried out twice in total. The induction of virus-derived antigen peptide-specific CTL was then evaluated in accordance with the method described in Example 14. As a result, the number of IFN-γ-producing cell spots in the wells to which the virus-derived antigen peptides had been added was found to be significantly larger than that in the wells to which the negative control peptides had been added in both the A2 homozygous knock-in mice and the A2 heterozygous knock-in mice (Student's t-test, $p<0.001$), and the induction of epitope-specific CTL was observed, as shown in FIG. 14.

Example 18: Confirmation of CTL Induction Capacity in A31 Knock-In Mice

The virus-derived antigen peptides described below were dissolved at 1 mg/ml in Otsuka distilled water (Otsuka Pharmaceutical Factory, Inc.) and filled into a B Braun Injekt syringe.

A31V3:
(SEQ ID NO: 53)
ASCMGLIYNR

A31V5:
(SEQ ID NO: 54)
SVQPTFSVQR

A31V6:
(SEQ ID NO: 55)
KFLPDLYDYK

-continued

A31V8:

(SEQ ID NO: 56)

SFSFGGFTFK

A31V10:

(SEQ ID NO: 57)

RVIDPRRCMK

Figure 15:
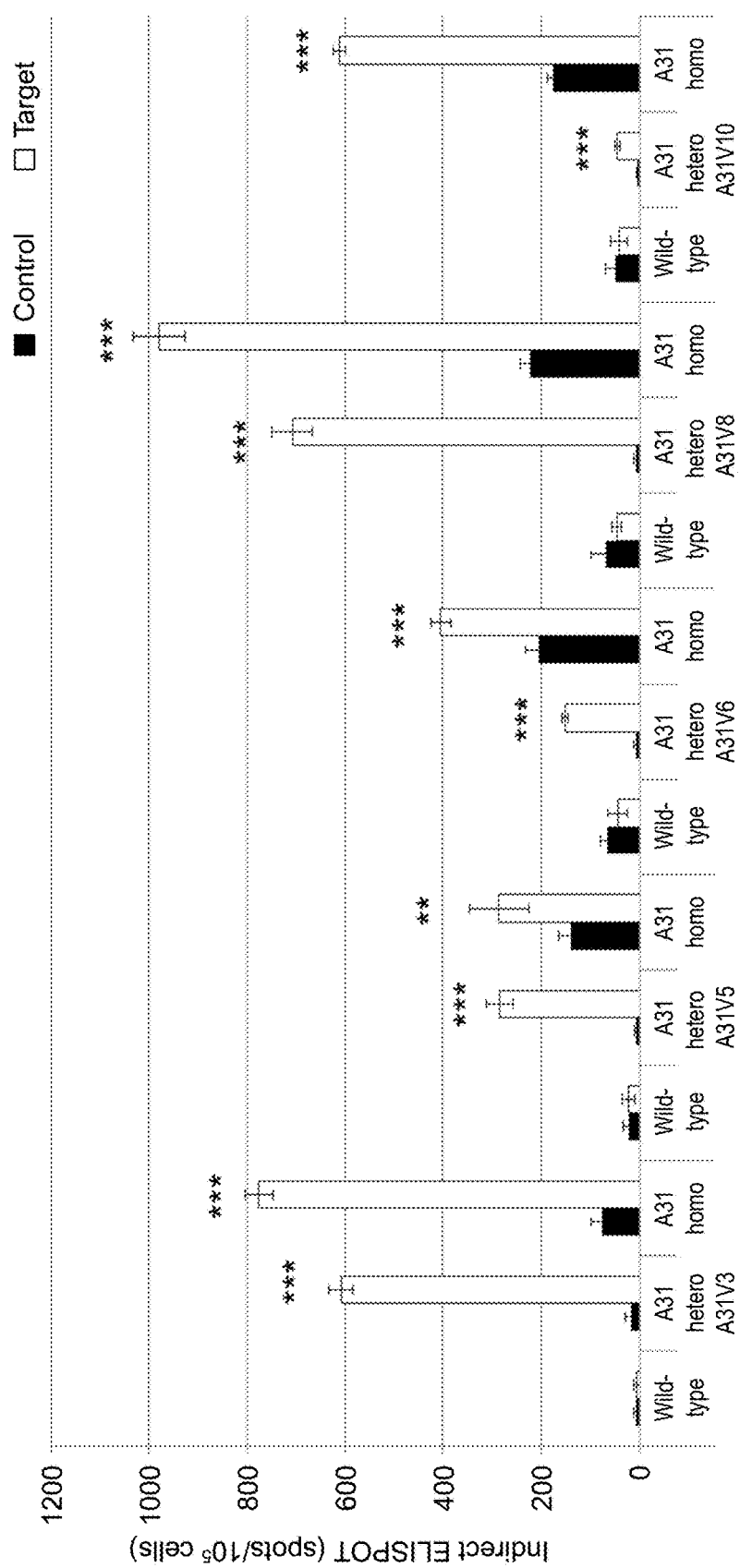
FIG. 15 shows the results of evaluation of the capacity of virus-derived antigen peptides for CTL induction using wild-type mice, heterozygous knock-in mice carrying an artificial chimeric gene (including HLA-A3-1), and homozygous knock-in mice carrying artificial chimeric genes (including HLA-A31) (* indicates p<0.001;  indicates p<0.01).

After another syringe was filled with an equivalent amount of Incomplete Freund's adjuvant (IFA), these syringes were connected together with the aid of a GP syringe connector, and the solution of virus-derived antigen peptides was thoroughly mixed with IFA to prepare an emulsion. The emulsion was administered subcutaneously to A31 homozygously knocked in mice, A31 heterozygous knock-in mice, and wild-type littermate mice through the tail heads in amounts of 100 μl/mouse once per week, and administration was carried out twice in total. The induction of virus-derived antigen peptide-specific CTL was then evaluated in accordance with the method described in Example 14. As a result, the number of IFN-γ-producing cell spots in the wells to which the virus-derived antigen peptides had been added was found to be significantly larger than that in the wells to which the negative control peptides had been added in both the A31 homozygous knock-in mice and the A31 heterozygous knock-in mice (Students t-test, p<0.01 or p<0.001), and the induction of epitope-specific CTL was observed, as shown in FIG. 15.

Example 19: Analysis of CD4$^-$CD8$^+$T Cell Population in Knock-In Mice

HHD-A2402 homozygous knock-in mice, HHD-A0301 homozygous knock-in mice, HHD-A0201 homozygous knock-in mice, HHD-A3101 homozygous knock-in mice, HHD-A2402 heterozygous knock-in mice, HHD-A0301 heterozygous knock-in mice, HHD-A0201 heterozygous knock-in mice, HHD-A3101 heterozygous knock-in mice, wild-type mice as control littermates, and HHD-A2402/HHD-A0301 double knock-in mice were euthanized, and CD4 and CD8 expressions on the blood cell surface were analyzed via flow cytometry. Specifically, 1×10$^6$ blood cells were stained with the monoclonal PE-Cy7-labeled anti-CD4 antibody GK1.5 (eBioscience) and the FITC- or APC-labeled anti-CD8 antibody 53-6.7 (eBioscience).

Figures 1, 16:
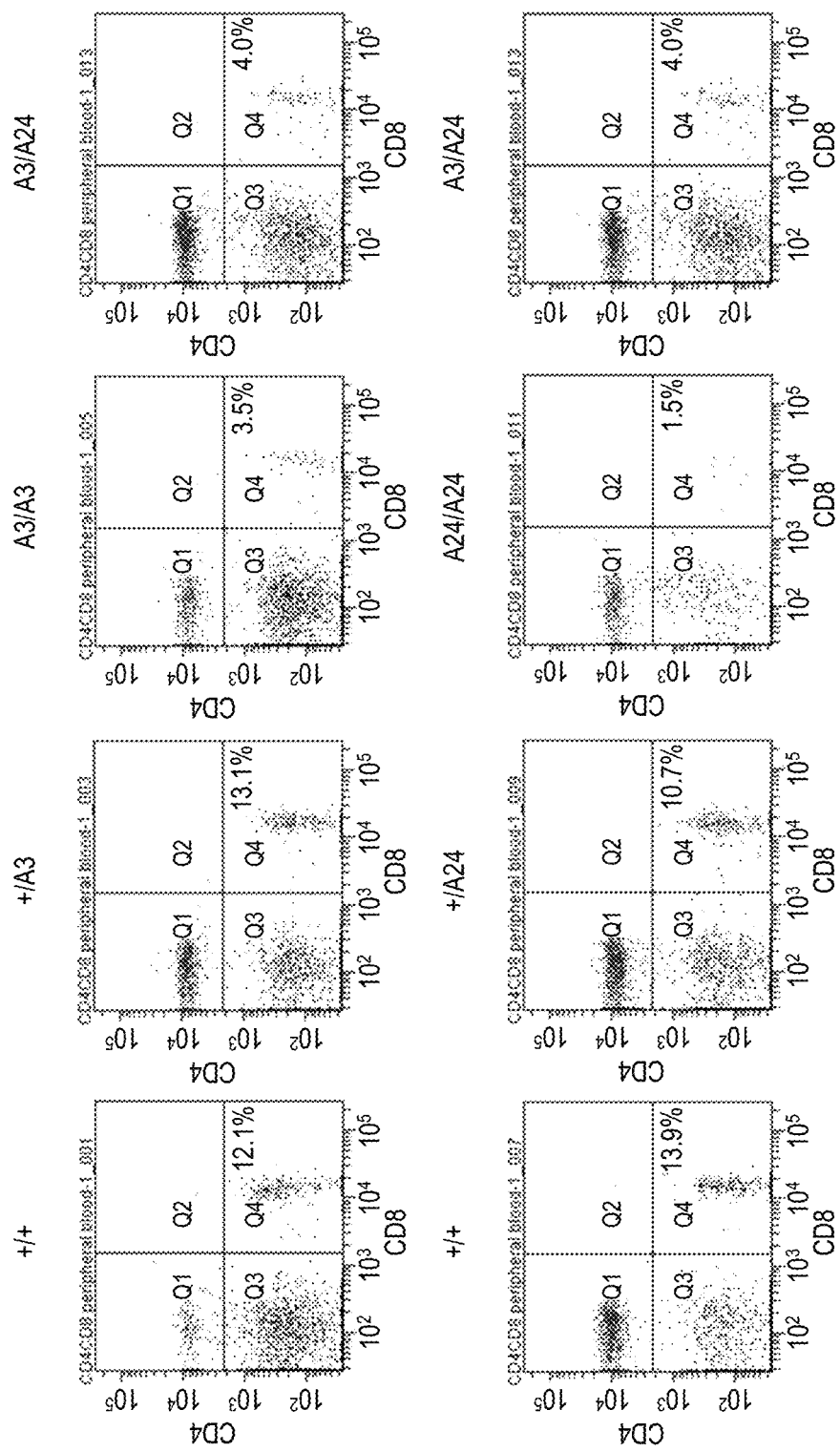
Figures 2, 16:
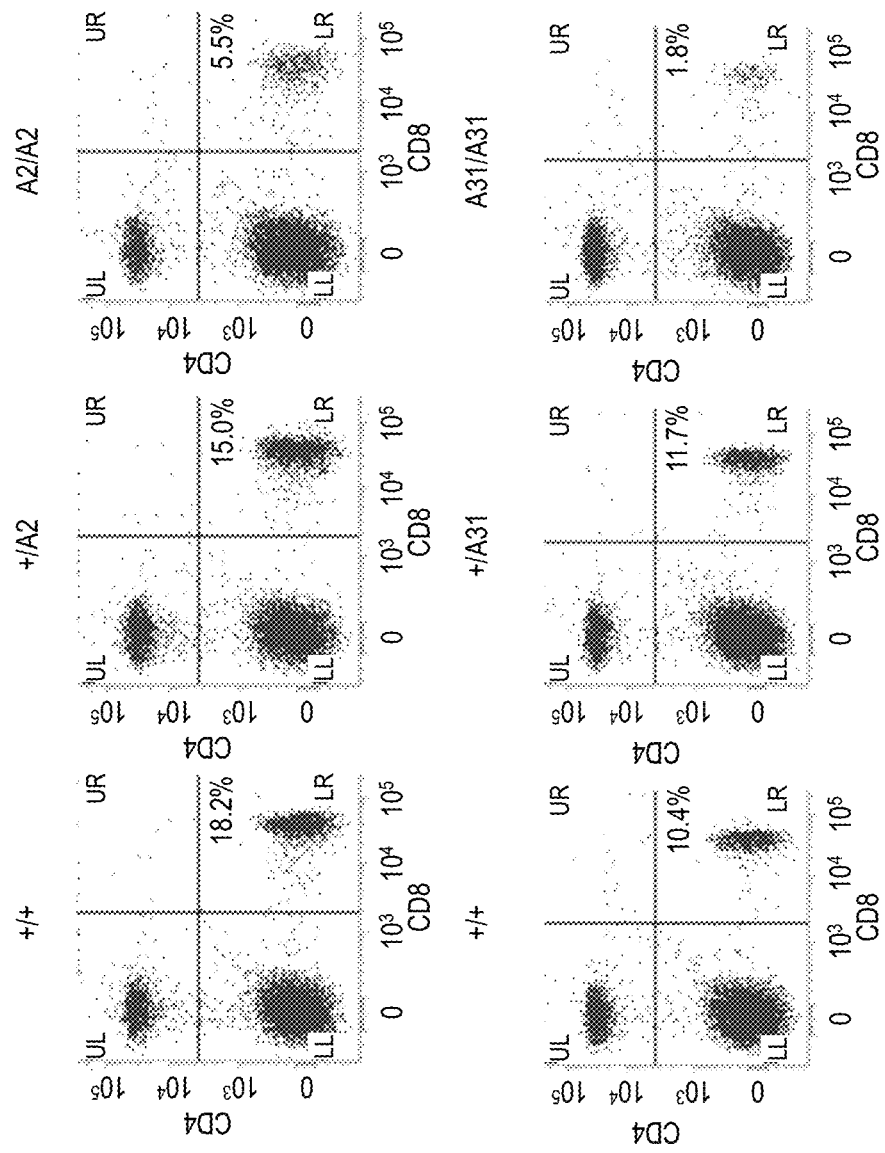

As a result, the proportions of CD4$^-$CD8$^+$T cells in HHD-A2402 heterozygous knock-in mice, HHD-A0301 heterozygous knock-in mice, HHD-A0201 heterozygous knock-in mice, and HHD-A3101 heterozygous knock-in mice were found to be equivalent to those in wild-type mice. In contrast, the proportions of CD4$^-$CD8$^+$T cells in HHD-A2402 homozygous knock-in mice, HHD-A0301 homozygous knock-in mice, HHD-A0201 homozygous knock-in mice, HHD-A3101 homozygous knock-in mice, and HHD-A2402/HHD-A0301 double knock-in mice were found to have significantly decreased in comparison with those in wild-type mice (FIG. 16-1 and FIG. 16-2).

All publications, patents, and patent applications cited herein are incorporated herein by reference in their entirety.

The invention claimed is:

1. An HLA class I gene knock-in rodent comprising an artificial chimeric gene encoding an artificial chimeric protein comprising β2 microglobulin, HLA class I α1 and α2 regions, and a rodent MHC class I α3 region ligated in such order from the N terminus wherein the artificial chimeric gene (a) is knocked into at least one β2 microglobulin locus of the rodent and (b) is operably linked to an endogenous transcription regulatory region of β2 microglobulin gene of the at least one β2 microglobulin locus of the rodent, wherein the rodent is a mouse or a rat.

2. The HLA class I gene knock-in rodent according to claim 1, wherein the artificial chimeric gene is operably linked to the endogenous transcription regulatory region of β2 microglobulin gene in one β2 microglobulin locus.

3. The HLA class I gene knock-in rodent according to claim 1, wherein the HLA class I α1 and α2 regions are derived from HLA-A.

4. The HLA class I gene knock-in rodent according to claim 3, wherein the HLA-A is HLA-A24, HLA-A3, HLA-A2, or HLA-A31.

5. The HLA class I gene knock-in rodent according to claim 3, wherein the HLA-A is HLA-A2402, HLA-A0301, HLA-A0201, or HLA-A3101.

6. The HLA class I gene knock-in rodent according to claim 1, wherein the rodent comprises two chimeric genes, a first artificial chimeric gene encoding a first artificial chimeric protein comprising β2 microglobulin, HLA class I α1 and α2 regions, and a rodent MHC class I α3 region ligated in such order from the N terminus, wherein the first artificial chimeric gene (a) is knocked into a first 2 microglobulin locus of the rodent and (b) is operably linked to the endogenous transcription regulatory region of β2 microglobulin gene in the first β2 microglobulin locus of the rodent;

and a second artificial chimeric gene encoding a second artificial chimeric protein comprising β2 microglobulin, HLA class I α1 and α2 regions, and a rodent MHC class I α3 region ligated in such order from the N terminus, wherein the second artificial chimeric gene (a) is knocked into a second β2 microglobulin locus of the rodent and (b) is operably linked to the endogenous transcription regulatory region of β2 microglobulin gene in the second β2 microglobulin locus of the rodent.

7. The HLA class I gene knock-in rodent according to claim 6, wherein the HLA class I α1 and α2 regions of the first artificial chimeric protein and the HLA class I α1 and α2 regions of the second artificial chimeric protein are derived from HLA of the same genotype.

8. The HLA class I gene knock-in rodent according to claim 6, wherein the HLA class I α1 and α2 regions of the first artificial chimeric protein and the HLA class I α1 and α2 regions of the second artificial chimeric protein are derived from HLA of different genotypes.

9. The HLA class I gene knock-in rodent according to claim 6, wherein the HLA class I α1 and α2 regions of the first artificial chimeric protein and the HLA class I α1 and α2 regions of the second artificial chimeric protein are derived from HLA-A.

10. The HLA class I gene knock-in rodent according to claim 9, wherein the HLA class I α1 and α2 regions of the first artificial chimeric protein and the HLA class I α1 and α2 regions of the second artificial chimeric protein are the same or different, and are derived from HLA-A24, HLA-A3, HLA-A2, or HLA-A31.

11. The HLA class I gene knock-in rodent according to claim 9, wherein the HLA class I α1 and α2 regions of the first artificial chimeric protein and the HLA class I α1 and α2 regions of the second artificial chimeric protein are the same or different, and are derived from HLA-A2402, HLA-A0301, HLA-A0201, or HLA-A3101.

12. The HLA class I gene knock-in rodent according to claim 1, wherein the rodent MHC class I α3 region is derived from H-2 class I.

13. The HLA class I gene knock-in rodent according to claim 12, wherein the rodent MHC class I α3 region is derived from mouse H-2D$^b$.

14. The HLA class I gene knock-in rodent according to claim 1, wherein the β2 microglobulin is human β2 microglobulin.

15. The HLA class I gene knock-in rodent according to claim 1, wherein the rodent is a mouse.

16. The HLA class I gene knock-in rodent according to claim 15, which has a genotype represented as B2 m$^{+/(HLA/H-2/B2M)}$ or B2m$^{(HLA/H-2/B2M)/(HLA/H-2/B2M)}$.

17. A method for preparing an HLA class I gene knock-in rodent, comprising introducing an artificial chimeric gene encoding an artificial chimeric protein comprising β2 microglobulin, HLA class I α1 and α2 regions, and a rodent MHC class I α3 region ligated in such order from the N terminus into a site under the control of an endogenous transcription regulatory region of β2 microglobulin gene of the rodent, wherein the artificial chimeric gene is knocked into at least one β2 microglobulin locus of the rodent and wherein the rodent is a mouse or a rat.

18. The method according to claim 17 further comprising the following steps:
(1) preparing a targeting vector comprising the artificial chimeric gene encoding the artificial chimeric protein comprising of β2 microglobulin, HLA class I α1 and α2 regions, and a rodent MHC class I α3 region ligated in such order from the N terminus; and
(2) allowing the targeting vector to react with a pluripotent stem cell of the rodent, so as to introduce the targeting vector into a site under the control of the endogenous transcription regulatory region of β2 microglobulin gene of the pluripotent stem cell, wherein the artificial chimeric gene is knocked into at least one 12 microglobulin locus of the pluripotent stem cell.

19. The method according to claim 18, wherein the pluripotent stem cell is an ES cell, GS cell, or iPS cell.

20. The method according to claim 18, wherein the artificial chimeric gene is introduced into the site under the control of the endogenous transcription regulatory region of β2 microglobulin gene of the pluripotent stem cell via homologous recombination.

21. The method according to claim 17, wherein the β2 microglobulin is human β2 microglobulin.

22. A rodent cell that expresses an artificial chimeric gene encoding an artificial chimeric protein comprising β2 microglobulin, HLA class I α1 and α2 regions, and a rodent MHC class I α3 region ligated in such order from the N terminus, wherein the artificial chimeric gene is (a) operably linked to an endogenous transcription regulatory region of β2 microglobulin gene of the rodent cell and (b) is knocked into at least one β2 microglobulin locus of the rodent cell, wherein the rodent is a mouse or a rat.

23. The rodent cell according to claim 22, which is an ES cell, GS cell, or iPS cell.

24. An isolated tissue, isolated organ, isolated cell, primary cell culture, or established cell line that is obtained from the HLA class I gene knock-in rodent according to claim 1.

25. A method for screening for test-substance-specific CTL induction comprising
(1) allowing a test substance to react with
the HLA class I gene knock-in rodent according to claim 1,
a rodent cell that expresses an artificial chimeric gene encoding an artificial chimeric protein comprising β2 microglobulin, HLA class I α1 and α2 regions, and a rodent MHC class I α3 region ligated in such order from the N terminus, wherein the artificial chimeric gene is (a) operably linked to an endogenous transcription regulatory region of β2 microglobulin gene of the rodent cell and (b) is knocked into at least one β2 microglobulin locus of the rodent cell, or
an isolated tissue, isolated organ, isolated cell, primary cell culture, or established cell line that is obtained from the HLA class I gene knock-in rodent according to claim 1; and
(2) determining whether test-substance-specific CTL is induced.

26. A method for determining the presence or absence of an HLA class I-restricted antigen, comprising
(1) allowing a test substance to react with
the HLA class I gene knock-in rodent according to claim 1,
a rodent cell that expresses an artificial chimeric gene encoding an artificial chimeric protein comprising β2 microglobulin, HLA class I α1 and α2 regions, and a rodent MHC class I α3 region ligated in such order from the N terminus, wherein the artificial chimeric gene is (a) operably linked to an endogenous transcription regulatory region of β2 microglobulin gene of the rodent cell and (b) is knocked into at least one β2 microglobulin locus of the rodent cell, or
an isolated tissue, isolated organ, isolated cell, primary cell culture, or established cell line that is obtained from the HLA class I gene knock-in rodent according to claim 1; and (2) determining whether test-substance-specific CTL is induced, wherein the presence of test-substance-specific CTL induction indicates that the test substance comprises an HLA class I-restricted antigen.

27. A method for screening a therapeutic or preventive agent of a disease, comprising
(1) reacting a test substance with
the HLA class I gene knock-in rodent according to claim 1,
a rodent cell that expresses an artificial chimeric gene encoding an artificial chimeric protein comprising β2 microglobulin, HLA class I α1 and α2 regions, and a rodent MHC class I α3 region ligated in such order from the N terminus, wherein the artificial chimeric gene is (a) operably linked to an endogenous transcription regulatory region of β2 microglobulin gene of the rodent cell and (b) is knocked into at least one β2 microglobulin locus of the rodent cell, or
an isolated tissue, isolated organ, isolated cell, primary cell culture, or established cell line that is obtained from the HLA class I gene knock-in rodent according to claim 1; and
(2) determining whether test-substance-specific CTL is induced, wherein the presence of test-substance-specific CTL induction indicates that the test substance is a therapeutic or preventive agent of a disease.

28. The method according to claim 27, wherein the disease is a cancer or infection.

29. A method for comparing HLA-restricted specificity of CTL reactions induced by test substances, comprising
(1) administering test substances to a plurality of different strains of the HLA class I gene knock-in rodent according to claim 1 that express different HLA class I genes and assaying the CTL reactions induced in the plurality of different strains of the HLA class I gene knock-in rodent; and
(2) comparing the CTL reactions assayed in the plurality of different strains of the HLA class I gene knock-in rodent and evaluating the HLA-restriction of test substances inducing CTL reactions.

30. A method for evaluating effectiveness of CTL reactions induced by test substances, comprising
(1) administering test substances to a plurality of different strains of the HLA class I gene knock-in rodent according to claim 1 that express different HLA class I genes and assaying the CTL reactions induced in the plurality of different strains of the HLA class I gene knock-in rodent; and
(2) comparing the CTL reactions assayed in the plurality of different strains of the HLA class I gene knock-in rodent and evaluating the HLA-restriction of test substances inducing CTL reactions.

31. A method for evaluating the safety of a test substance, comprising
(1) allowing a test substance to react with the HLA class I gene knock-in rodent according to claim 1; and
(2) analyzing unfavorable reactions occurring in the rodent.

32. The method according to claim 31, wherein the unfavorable reactions are autoimmune reactions.

33. The method according to claim 25, wherein the test substances are one or more of peptides, one or more of polypeptides, one or more of oligonucleotides, one or more of polynucleotides, or one or more of proteins.

* * * * *

UNITED STATES PATENT AND TRADEMARK OFFICE
CERTIFICATE OF CORRECTION

PATENT NO.        : 10,278,373 B2
APPLICATION NO.   : 15/029305
DATED             : May 7, 2019
INVENTOR(S)       : Naomoto Harada and Satoshi Fukaya It is certified that error appears in the above-identified patent and that said Letters Patent is hereby corrected as shown below:

In the Claims

Column 86, Claim 6, Line 55, "knocked into a first 2 micro-" should be -- knocked into a first β2 micro- --.

Signed and Sealed this
Seventeenth Day of September, 2019

Andrei Iancu
*Director of the United States Patent and Trademark Office*